(12) United States Patent
Zhang

(10) Patent No.: US 11,767,295 B2
(45) Date of Patent: Sep. 26, 2023

(54) ISOINDOLE DERIVATIVE

(71) Applicant: TIANJIN HEMAY PHARMACEUTICAL CO., LTD., Tianjin (CN)

(72) Inventor: Hesheng Zhang, Tianjin (CN)

(73) Assignee: TIANJIN HEMAY PHARMACEUTICAL CO., LTD., Tianjin (CN)

( * ) Notice: Subject to any disclaimer, the term of this patent is extended or adjusted under 35 U.S.C. 154(b) by 0 days.

(21) Appl. No.: 17/048,914

(22) PCT Filed: Apr. 16, 2019

(86) PCT No.: PCT/CN2019/082943
§ 371 (c)(1),
(2) Date: Oct. 19, 2020

(87) PCT Pub. No.: WO2019/201255
PCT Pub. Date: Oct. 24, 2019

(65) Prior Publication Data
US 2021/0155590 A1     May 27, 2021

(30) Foreign Application Priority Data

Apr. 17, 2018 (CN) .......................... 201810341153.0

(51) Int. Cl.
*C07D 209/48* (2006.01)
*A61P 17/00* (2006.01)

(52) U.S. Cl.
CPC ............ *C07D 209/48* (2013.01); *A61P 17/00* (2018.01)

(58) Field of Classification Search
CPC ............................... C07D 209/19; A61P 17/00
See application file for complete search history.

(56) References Cited

U.S. PATENT DOCUMENTS

| 5,605,914 A | 2/1997 | Muller |
| 6,214,857 B1 * | 4/2001 | Muller ................ C07D 413/04 |
| | | 514/266.3 |

FOREIGN PATENT DOCUMENTS

| CN | 1423633 A | 6/2003 |
| CN | 101885731 A | 11/2010 |
| PL | 198522 B1 | 6/2008 |
| WO | WO-1995/001348 A2 | 1/1995 |
| WO | WO-1999/006041 A1 | 2/1999 |
| WO | WO-2001/034606 A1 | 5/2001 |
| WO | WO-2001/046183 A1 | 6/2001 |
| WO | WO-2004/060313 A2 | 7/2004 |

OTHER PUBLICATIONS

Niwayama et al., 39(16) J. Med. Chem. 3044-45 (1996) (Year: 1996).*
Muller et al., 39(17) J. Med. Chem. 3238-3240 (1996) (Year: 1996).*
Wu et al., 27(9) Youji Huaxue 1110-1115 (2007) (Year: 2007).*
Xu et al., "Cobalt-Catalyzed Decarboxylative Acetoxylation of Amino Acids and Arylacetic Acids," Organic Letters, 17(18):4476-4478 (2015).
Zhang et al., "Detection of Serum IgE and Analysis of Allergens in Children with Atopic Dermatitis and Chronic Urticaria," Guangdong Medicine, 28(10): 1688-1690 (2007).
Zhao et al., "The Role of IgE in Allergic Asthma and Anti-IgE Treatment," Journal of Clinical Pulmonology, 23(7):1325-1328 (2018).
He et al., "Clinical Features of Asthma-COPD Overlap Syndrome," International Journal of Respiratory Medicine, 37(16):1207-1210 (2017).
Xu et al., "Detection of Total IgE and Specific IgE in Patients with Chronic Urticaria," Journal of Shanghai Second Medical University, 14(suppl):118-120 (1994).
Li et al., "The Expression and Significance of IgE in the Nasal Mucosa of Patients with Allergic Rhinitis," Preventive Medicine Journal of the PLA, 36(10):13-15 (2018).
Holgate, "New Strategies with Anti-IgE in Allergic Diseases," World Allergy Organization Journal, 2014, 7(17):1-6 (2014).
Wang and Sun, "Progress in the Treatment of IgE-Related Allergic Diseases," Journal of Clinical Military Medicine, 8:872-874 (2017).
Yin et al., "Drug-Induced Interstitial Pneumonia," China Pharmaceutical Congress and Chinese Pharmacist Week (2010).
He et al., "A Preliminary Discussion on the Content of IgE in the Serum of Leprosy Patients," Chinese Journal of Leprosy and Skin Diseases, 4:210-211 (1989).
Yin and Li, "Research Progress on the Relationship between IgE and Autoimmune Diseases," Chinese Journal of Laboratory Medicine, 41(3): 242-245 (2018).
Wang et al., "Synthesis, Biological Evaluation and Molecular Modeling of 1H-benzo[d]imidazole Derivatives as Novel Anti-tubulin Polymerization Agents," RSC Advances, 5(91):74425-74437 (2015).

(Continued)

*Primary Examiner* — Timothy R Rozof
(74) *Attorney, Agent, or Firm* — Goodwin Procter LLP

(57) ABSTRACT

Disclosed is a compound of formula (I) and a stereoisomer thereof:

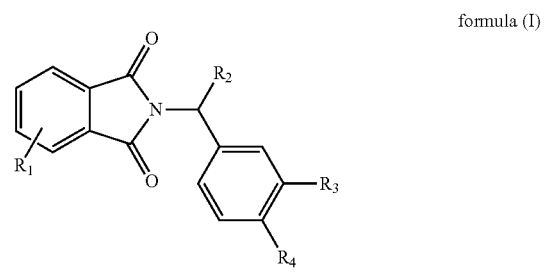

formula (I)

wherein $R_1$, $R_2$, $R_3$ and $R_4$ are as defined in the present disclosure.

29 Claims, 5 Drawing Sheets

(56) References Cited

OTHER PUBLICATIONS

Van Quaquebeke et al., "2,2,2-Trichloro-N-({2-[2-(dimethylamino)ethyl]-1,3-dioxo-2,3-dihydro-1H-benzo[de]isoquinolin-5yl}carbamoyl)acetamide (UNBS3157), a Novel Nonhematotoxic Naphthalimide Derivative with Potent Antitumor Activity," Journal of Medicinal Chemistry, 50(17): 4122-4134 (2007).
International Search Report and Written Opinion for PCT/CN2019/082943, dated Jul. 25, 2019, with English Language Translation.
Muller et al., "Thalidomide analogs and PDE4 inhibition," Bioorganic & Medicinal Chemistry Letters, 8(19):2669-2674 (1998).
Avila et al., "Development of new CoMFA and CoMSIA 3D-QSAR models for anti-inflammatory phthalimide-containing TNFalpha modulators," Bioorganic & Medicinal Chemistry, 14(20):6874-6885 (2016).
Zhang et al., "Enantioselective Allylic Amination of Morita-Baylis-Hillman Carbonates Catalysed by Modified Cinchona Alkaloids," European Journal of Organic Chemistry, 2009(33):5804-5809 (2009).
Wu et al., "Synthesis of 5-amino-1,3-dihydro-1,3-dioxo-isoindole-2-propanoic acid derivatives and determination of their activity as angiogenesis inhibitors," Chinese Journal of Organic Chemistry, 27(9):1110-1115 (2007).
Kora et al., "Synthesis and antimicrobial activity of some new 5,6-dichloro-4,7-diiodo-2-(substituted)-1,3-isoindolindione derivatives," Indian Journal of Heterocyclic Chemistry, 2(1):29-34 (1992).
Kim et al., "Chiral Recognition of N-Phthaloyl, N-Tetrachlorophthaloyl, and N-Naphthaloyl [alpha]-Amino Acids and Their Esters on Polysaccharide-Derived Chiral Stationary Phases," Chirality, 24(12):1037-1046 (2012).
CAS Registry No. 342777-63-3; STN Entry Date Jun. 21, 2001.
CAS Registry No. 342777-65-5; STN Entry Date Jun. 21, 2001.
CAS Registry No. 1042222-42-3; STN Entry Date Aug. 20, 2008.
CAS Registry No. 1042222-43-4; STN Entry Date Aug. 20, 2008.
CAS Registry No. 1042222-44-5; STN Entry Date Aug. 20, 2008.
CAS Registry No. 1042222-45-6; STN Entry Date Aug. 20, 2008.
CAS Registry No. 1051926-63-6; STN Entry Date Sep. 23, 2008.
CAS Registry No. 1705369-90-9; STN Entry Date May 15, 2015.
CAS Registry No. 1705464-42-1; STN Entry Date May 15, 2015.
CAS Registry No. 1705492-81-4; STN Entry Date May 15, 2015.
CAS Registry No. 200483-31-4; STN Entry Date Jan. 29, 1998.
CAS Registry No. 200483-33-6; STN Entry Date Jan. 29, 1998.
CAS Registry No. 200483-32-5; STN Entry Date Jan. 29, 1998.
Dermeche et al., "Qualitative Structure-Activity Relationships and 2D-QSAR Modeling of TNF-? Inhibition by Thalidomide Derivatives," Journal of Bionanoscience, 9(5):395-400 (2015).
Boto, et al. "Genotoxic activity of halogenated phenylglycine derivatives," Bioorganic & Medicinal Chemistry Letters 16 (2006) pp. 6073-6077.
Fernanedez-Martinez et. al. "Immunomodulatory effects of thalidomide analogs on LPS-induced plasma and hepatic cytokines in the rat," Biochemical Phamacology, 68 (2004) pp. 1321-1329.
Kashif et al. "Synthesis molecular docking and biological evaluationof novel phthaloyl dderivatives of 3-amino-3-aryl propionic acids as inhibitors of Trypanosoma cruzi trans-sialidase" European Journal of Medicinal Chemistry, 156 (2018) pp. 252-268.

* cited by examiner

ISOINDOLE DERIVATIVE

CROSS REFERENCE TO RELATED APPLICATIONS

This application is a U.S. national stage application filed under 35 U.S.C. § 371 of International Application No. PCT/CN2019/082943, filed Apr. 16, 2019, which claims priority to and the benefit of Chinese Patent Application No. 201810341153.0, filed Apr. 17, 2018, the contents of each of which are hereby incorporated by reference herein in their entirety.

FIELD

The present disclosure generally relates to organic chemistry and medicinal chemistry fields.

BACKGROUND

Immunoglobulin E (IgE) is a secretory immunoglobulin comprising two light chains and two heavy chains. It is produced by plasma cells in the lamina propria of the nasopharynx, tonsils, bronchi, gastric mucosa, etc. It is the main antibody that causes type I allergy. Although the content of this kind of antibody is the lowest in human serum, it plays an important role in allergic diseases and can cause inflammatory immune responses in different tissues and organs. The clinical manifestations of IgE-related diseases ranges from mild symptoms to life-threatening events. It has raised more and more attention due to its significant effects on the physical and mental health of patients, which leads to a decline in quality of life.

Eczema is a chronic, recurrent and inflammatory skin disease that often occurs in infants and children and can also occur in adults. According to researches, the prevalence of eczema in western countries is as high as 10% and 10.7% in the United States. Epidemiological studies in recent years have shown that the prevalence of this disease in the general population of China is getting close to that in western countries. It is still rising in industrialized countries in the recent 20 years. While China continues to advance the industrialization process, people's living standards have improved significantly. The prevalence of infectious dermatosis in China has gradually decreased, while the prevalence of allergic dermatosis has gradually increased. The pathogenesis is complicated, which is mainly related to genetic background, environmental stimulation, epidermal barrier defects, immune disorders and other factors. The destruction of the epidermal barrier stimulates the inflammatory response. B cells produce IgE in the acute phase, causing degranulation of mast cells and basophils. In the acute phase, the epidermis thickens, nerve fibers proliferate, and expression of chemokines increases. The disease is often accompanied by severe pruritus and repeated attacks from mild to severe circumstances. The course of the disease is prolonged and difficult to heal. It is a clinically chronic, recurrent and inflammatory dermatosis that can last for months, years or even decades. The most obvious symptom is severe pruritus, which can significantly affect patients' study, work and living. It can also affect sleep quality in severe cases. The impact of this type of allergic dermatosis on the quality of life of patients and their families and the increasing economic burden on society urgently require researches on the pathogenic factors and pathogenesis of the disease to establish appropriate responses at a social level to alleviate or eliminate the clinical symptoms, eliminate the inducing and/or aggravating factors, reduce and prevent recurrences, improve the quality of life of patients and resolve or improve the symptoms, so that patients can enjoy a normal life.

More than 80% of patients with atopic dermatitis have significantly higher total IgE in serum than normal people (Zhang Jintao et al., Guangdong Medicine, 2007, 28 (10), 1688-1690). Total IgE concentration in serum is positively correlated with severity of the disease of a patient with atopic dermatitis, which indicates that IgE in serum is an indicator of the activity of atopic dermatitis. In the pathogenesis of atopic dermatitis, IgE plays a very important role. After the external antigen binds to IgE, it promotes the increase of eosinophilia in blood through two ways: (1) Antigen binds to IgE receptors on mast cells and stimulates the mast cells to release eosinophilic chemokines. (2) Antigen is phagocytized by Langerhans cells in epidermis and presented to T cells. T cells are activated to produce a variety of cytokines including eosinophil chemokines. The alkaline protein released by degranulation of a large number of eosinophils causes tissue damage.

Asthma, also known as bronchial asthma, is a chronic tracheal disease with tracheal spasm as the main pathological feature. It is a chronic airway inflammation involving multiple cells and cellular components. Airway inflammation is a common feature of almost all types of asthma and is also a clinical symptom and the basis of high reactivity of airway. IgE plays a very important role in the inflammatory response of asthma (Zhao Xinyu et al., Journal of Clinical Pulmonology, 2018, 23 (7), pages 1325-1328). When the allergen enters the body for the first time, a series of inflammatory cascades are triggered by the presentation of dendritic cells. B cells produce a large amount of IgE, which bind to the high-affinity receptors of IgE (FcεRI) on the surface of mast cells and basophils to form the FcεRI-IgE complex. When the allergen enters the body again, it can quickly bind to the complex, which leads to the release of a large amount of histamine, leukotriene, prostaglandin and other inflammatory mediators and causes mucus secretion, airway smooth muscle contraction and the increase of vascular permeability. Inflammatory cells can cascade to expand the production of IgE under the action of the above inflammatory mediators, cause a delayed allergy and accelerate the progress of asthma. Another study points out that specific IgE molecules can also bind to dendritic cells to enhance their antigen presentation and upregulate the expression of FcεRI receptors on the surface of mast cells and basophils. Some studies show that IgE can lead to airway remodeling by increasing extracellular matrix (ECM) and also involve in the virus-induced acute attack of asthma.

Asthma-chronic obstructive pulmonary disease (COPD) overlapping syndrome (ACOS) is an obstructive airway disease that includes both asthma and COPD (He Zhong et al., International Journal of Respiratory Medicine, 2017, 37 (16), 1207-1210 Page). There are usually the following three common pathophysiological changes, namely: airway inflammation, airway obstruction (AO) and airway hyperresponsiveness (AHR). Spanish expert consensus concludes if COPD patients have a strong positive bronchodilation test, eosinophils in sputum, increased total IgE content, asthma before the age of 40 and personal allergy history, a diagnosis of ACOS can be done.

Urticaria (Xu Yawei et al., Journal of Shanghai Second Medical University, Vol. 14, Suppl. 1994, 118-120), commonly known as "rubella block", is a limited edema reaction occurred due to the expansion of skin and mucosa small blood vessels and increased permeability. The clinical manifestations are wheals of various sizes accompanied by pruritus. The regression usually occurs within 2 to 24 hours, but new rashes usually occur repeatedly. Chronic urticaria refers to that the above wheals accompanied by pruritus occur almost every day and last more than 6 weeks. Although the pathogenesis of urticaria is quite complicated, it is all related to activation of mast cells. The mast cell can be activated either by the immune way or by the non-immune way. As to the former, skin edema wheals occur either in IgE-dependent immune response or in complement system-mediated immune response.

Allergic rhinitis, also called nasal allergy, is a non-infectious inflammatory disease of the nasal mucosa, which relates to the release of IgE-mediated media (mainly histamine) after atopic individuals contact with allergens and involves a variety of immune-active cells and cytokines. Allergic rhinitis is perennial and seasonal and occurs at any age, most commonly seen in adolescents. The symptoms of the patient are sneezing, tearing, clearing the nose, arm pruritus and loss of smell. IgE-mediated type I allergy is the basis of allergic reactions. Li Zhaohui et al. (Li Zhaohui et al., Preventive Medicine Journal of the PLA, 2018, 36 (10), 13-15) found that patients with allergic rhinitis had significantly higher IgE levels than normal people. IgE plays an important role in the pathogenesis of allergic rhinitis. That is, it participates in the immunogenic mechanism of allergic rhinitis. It can be used as an effective monitoring index for allergic rhinitis and has important clinical significance.

Common diseases associated with elevated level of IgE also include: seasonal allergic rhinitis (Holgate S, World Allergy Organization Journal, 2014, 7, 17 and Wang Hanmei, Sun Renshan, Journal of Clinical Military Medicine, 2017 (8), 872-874), drug-induced interstitial lung disease (Yin Wenjie, etc., China Pharmaceutical Congress and Chinese Pharmacist Week, 2010), bronchopulmonary aspergillosis (Holgate S, T, World Allergy Organization Journal, 2014, 7, 17), leprosy (He Haoming, etc., Chinese Journal of Leprosy and Skin Diseases, 1989 (4), 210-211), pemphigoid (Yin Yue, Li Li, Chinese Journal of Laboratory Medicine, 2018, 41 (3), 242-245) and some parasitic infections, etc.

The in-depth understanding of the action mechanism of IgE molecules has promoted the development of drugs that take the IgE inflammatory process as a therapeutic target. Anti-IgE treatment reduces the level of high-affinity IgE receptors (FcεRI) expressed in mast cells, basophils and dendritic cells by reducing the level of free IgE so that the inflammation markers are reduced, thereby exerting therapeutic effects. Omalizumab is the first humanized IgE monoclonal antibody targeting IgE. Omalizumab can be used in the treatment of patients like children, adolescents and adults with severe and persistent allergic asthma to reduce the number of acute attacks of asthma, reduce the use of inhaled hormones, improve asthma-related quality of life and reduce the frequency of hospitalization and emergency treatment for patients. It also has good safety. The most common adverse reaction is a transient injection site reaction. However, as a protein-antibody drug, not only is it difficult and complex to produce, but it is also extremely demanding in terms of storage and transportation. More importantly, it must have potential immunogenicity as therapeutic proteins. Small-molecular IgE inhibitors are a direction of drug development for allergic diseases. Small-molecular compounds have good pharmacological properties, better safety, low price and good patient compliance.

SUMMARY

In one aspect, the present disclosure relates to a compound of formula (I) and a stereoisomer thereof:

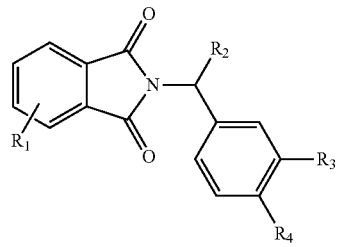

formula (I)

wherein $R_1$ represents one or more substituents selected from the group consisting of hydrogen, halogen, hydroxy, $C_1$-$C_8$hydrocarbyl, amino, $C_1$-$C_8$hydrocarbylcarbonylamino, $C_1$-$C_8$hydrocarbyloxycarbonylamino, amino substituted with one or more $C_1$-$C_4$hydrocarbyl and substituted aminocarbonyl$C_1$-$C_8$hydrocarbyl;

$R_2$ is selected from the group consisting of carboxyl and ester group;

$R_3$ is selected from the group consisting of hydrogen, hydroxy, halogen, $C_1$-$C_8$hydrocarbyloxy, $C_5$-$C_{12}$aryloxy and $C_5$-$C_{12}$cycloaryloxy; and $R_4$ is selected from the group consisting of hydrogen, halogen, hydroxy, $C_1$-$C_8$hydrocarbyloxy and $C_5$-$C_{12}$aryloxy.

In another aspect, the present disclosure relates to a pharmaceutical composition comprising a compound of formula (I), a stereoisomer thereof and a pharmaceutically acceptable carrier:

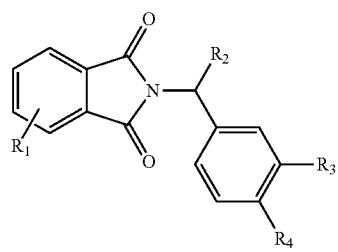

formula (I)

wherein $R_1$ represents one or more substituents selected from the group consisting of hydrogen, halogen, hydroxy, $C_1$-$C_8$hydrocarbyl, amino, $C_1$-$C_8$hydrocarbylcarbonylamino, $C_1$-$C_8$hydrocarbyloxycarbonylamino, amino substituted with one or more $C_1$-$C_4$hydrocarbyl and substituted aminocarbonyl$C_1$-$C_8$hydrocarbyl;

$R_2$ is selected from the group consisting of carboxyl and ester group;

$R_3$ is selected from the group consisting of hydrogen, hydroxy, halogen, $C_1$-$C_8$hydrocarbyloxy, $C_5$-$C_{12}$aryloxy and $C_5$-$C_{12}$cycloaryloxy; and $R_4$ is selected from the group consisting of hydrogen, halogen, hydroxy, $C_1$-$C_8$hydrocarbyloxy and $C_5$-$C_{12}$aryloxy.

In yet another aspect, the present disclosure relates to use of a compound of formula (I) or a stereoisomer thereof, or a pharmaceutical composition comprising a compound of formula (I) or a stereoisomer thereof and a pharmaceutically acceptable carrier in the preparation of a medicament for treating dermatosis, psoriasis, eczema and atopic dermatitis:

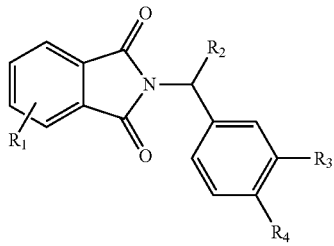

formula (I)

wherein $R_1$ represents one or more substituents selected from the group consisting of hydrogen, halogen, hydroxy, $C_1$-$C_8$hydrocarbyl, amino, $C_1$-$C_8$hydrocarbylcarbonylamino, $C_1$-$C_8$hydrocarbyloxycarbonylamino, amino substituted with one or more $C_1$-$C_4$hydrocarbyl and substituted aminocarbonyl$C_1$-$C_8$hydrocarbyl;

$R_2$ is selected from the group consisting of carboxyl and ester group;

$R_3$ is selected from the group consisting of hydrogen, hydroxy, halogen, $C_1$-$C_8$hydrocarbyloxy, $C_5$-$C_{12}$aryloxy and $C_5$-$C_{12}$cycloaryloxy; and $R_4$ is selected from the group consisting of hydrogen, halogen, hydroxy, $C_1$-$C_8$hydrocarbyloxy and $C_5$-$C_{12}$aryloxy.

In yet still another aspect, the present disclosure relates to a process for preparing a compound of formula (I) or a stereoisomer thereof:

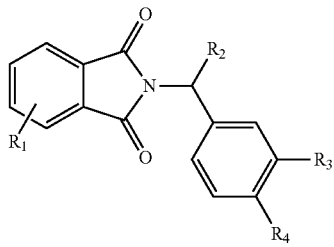

formula (I)

wherein $R_1$ represents one or more substituents selected from the group consisting of hydrogen, halogen, hydroxy, $C_1$-$C_8$hydrocarbyl, amino, $C_1$-$C_8$hydrocarbylcarbonylamino, $C_1$-$C_8$hydrocarbyloxycarbonylamino, amino substituted with one or more $C_1$-$C_4$hydrocarbyl and substituted aminocarbonyl$C_1$-$C_8$hydrocarbyl;

$R_2$ is selected from the group consisting of carboxyl and ester group;

$R_3$ is selected from the group consisting of hydrogen, hydroxy, halogen, $C_1$-$C_8$hydrocarbyloxy, $C_5$-$C_{12}$aryloxy and $C_5$-$C_{12}$cycloaryloxy; and $R_4$ is selected from the group consisting of hydrogen, halogen, hydroxy, $C_1$-$C_8$hydrocarbyloxy and $C_5$-$C_{12}$aryloxy.

wherein the process comprises:

(1) reacting a compound of formula (A-I) with malonic acid and ammonium acetate to obtain a compound of formula (A-II),

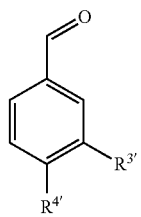

formula (A-I)

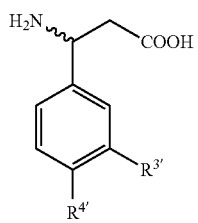

formula (A-II)

wherein groups represented by $R^{3'}$ and $R^{4'}$ in formula (A-I) and formula (A-II) have the same definitions as $R_3$ and $R_4$ in formula (I), (2) esterifying the compound of formula (A-II) with alcohol to obtain a compound of formula (A-III),

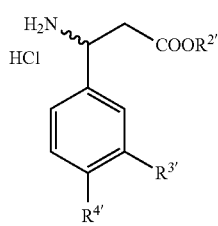

formula (A-III)

wherein groups represented by $R^{3'}$ and $R^{4'}$ in formula (A-II) and formula (A-III) have the same definitions as $R_3$ and $R_4$ in formula (I), and $R^{2'}$ is selected from the group consisting of hydrogen and $C_1$-$C_4$alkyl; and (3) reacting a compound of formula (A-IV) with the compound of formula (A-III) to obtain the compound of formula (I),

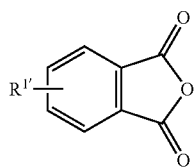

formula (A-IV)

wherein groups represented by $R^{1'}$, $R^{3'}$ and $R^{4'}$ in formula (A-III) and formula (A-IV) have the same definitions as $R_1$, $R_3$ and $R_4$ in formula (I), and $R^{2'}$ is selected from the group consisting of hydrogen and $C_1$-$C_4$alkyl.

In another aspect, the present disclosure relates to a compound of formula (II), a stereoisomer thereof, or a pharmaceutically acceptable salt thereof:

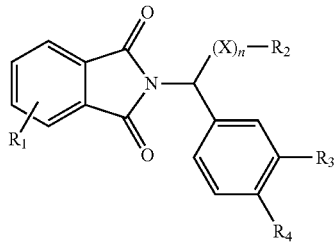

formula (II)

wherein

R$_1$ represents one or more identical or different substituents selected from the group consisting of halogen, hydroxy, optionally substituted hydrocarbyl, optionally substituted amino, optionally substituted hydrocarbylcarbonylamino, optionally substituted hydrocarbylcarbonyloxy, optionally substituted hydrocarbyloxycarbonylamino and optionally substituted hydrocarbylcarbonylamino;

R$_2$ is selected from the group consisting of optionally substituted hydrocarbyloxycarbonyl and carboxyl;

R$_3$ is selected from the group consisting of hydrogen, halogen, hydroxy, optionally substituted hydrocarbyloxy, optionally substituted arylhydrocarbyloxy and optionally substituted cyclohydrocarbyloxy;

R$_4$ is selected from the group consisting of hydrogen, halogen, hydroxy, optionally substituted hydrocarbyloxy, optionally substituted arylhydrocarbyloxy and optionally substituted cyclohydrocarbyloxy; and X is —CR$_5$R$_6$—, wherein if R$_5$ is selected from the group consisting of hydrogen, halogen, optionally substituted hydrocarbyl, optionally substituted cyclohydrocarbyl, optionally substituted aryl and optionally substituted heteroaryl; and R$_6$ is selected from the group consisting of hydrogen, halogen, optionally substituted hydrocarbyl, optionally substituted cyclohydrocarbyl, optionally substituted aryl and optionally substituted heteroaryl, n is 0, 1, 2, 3 or 4; and if R$_5$ and R$_6$ together with a carbon atom to which they are attached form an optionally substituted cyclohydrocarbyl, n is 1.

In yet another aspect, the present disclosure relates to a compound, a stereoisomer thereof, or a pharmaceutically acceptable salt thereof selected from the group consisting of:
methyl 3-(4-acetamido-1,3-dioxoisoindolin-2-yl)-3-(3-ethoxy-4-methoxyphenyl)propionate;
methyl 3-(4-amino-1,3-dioxoisoindolin-2-yl)-3-(3-ethoxy-4-methoxyphenyl)propionate;
methyl 3-(4-acetamido-1,3-dioxoisoindolin-2-yl)-3-(3,4-dimethoxyphenyl)propionate;
methyl 3-(4-acetamido-1,3-dioxoisoindolin-2-yl)-3-(3,4-diethoxyphenyl)propionate;
3-(4-acetamido-1,3-dioxoisoindolin-2-yl)-3-(3-ethoxy-4-methoxyphenyl) propanoic acid;
ethyl 3-(4-acetamido-1,3-dioxoisoindolin-2-yl)-3-(3-ethoxy-4-methoxyphenyl)propionate;
methyl (R)-3-(4-amino-1,3-dioxoisoindolin-2-yl)-3-(3-ethoxy-4-methoxyphenyl)propionate;
methyl (S)-3-(4-amino-1,3-dioxoisoindolin-2-yl)-3-(3-ethoxy-4-methoxyphenyl)propionate;
methyl (R)-3-(4-acetamido-1,3-dioxoisoindolin-2-yl)-3-(3-ethoxy-4-methoxyphenyl)propionate;
methyl (S)-3-(4-acetamido-1,3-dioxoisoindolin-2-yl)-3-(3-ethoxy-4-methoxyphenyl)propionate;
propyl 3-(4-acetamido-1,3-dioxoisoindolin-2-yl)-3-(3-ethoxy-4-methoxyphenyl)propionate;
isopropyl 3-(4-acetamido-1,3-dioxoisoindolin-2-yl)-3-(3-ethoxy-4-methoxyphenyl)propionate;
butyl 3-(4-acetamido-1,3-dioxoisoindolin-2-yl)-3-(3-ethoxy-4-methoxyphenyl)propionate;
methyl 3-(4-(2-chloroacetamido)-1,3-dioxoisoindolin-2-yl)-3-(3-ethoxy-4-methoxyphenyl)propionate;
methyl 3-(4-(2-(dimethylamino)acetamido)-1,3-dioxoisoindolin-2-yl)-3-(3-ethoxy-4-methoxy phenyl)propionate;
methyl 3-(4-(dimethylamino)-1,3-dioxoisoindolin-2-yl)-3-(3-ethoxy-4-methoxyphenyl)propionate;
methyl 3-(4-(2-hydroxyacetamido)-1,3-dioxoisoindolin-2-yl)-3-(3-ethoxy-4-methoxyphenyl)propionate;
methyl 3-(4-acetamido-1,3-dioxoisoindolin-2-yl)-3-(3-ethoxy-4-isopropoxyphenyl)propionate;
methyl 3-(4-fluoro-1,3-dioxoisoindolin-2-yl)-3-(3-ethoxy-4-methoxyphenyl)propionate;
methyl 3-(4-acetamido-1,3-dioxoisoindolin-2-yl)-3-(3-ethoxy-4-cyclopentyloxyphenyl)propionate;
methyl 3-(4-methyl-1,3-dioxoisoindolin-2-yl)-3-(3-ethoxy-4-methoxyphenyl)propionate;
methyl 3-(5-fluoro-1,3-dioxoisoindolin-2-yl)-3-(3-ethoxy-4-methoxyphenyl)propionate;
methyl 3-(4,7-dichloro-1,3-dioxoisoindolin-2-yl)-3-(3-ethoxy-4-methoxyphenyl)propionate;
methyl 3-(4-(N-methylacetamido)-1,3-dioxoisoindolin-2-yl)-3-(3-ethoxy-4-methoxyphenyl)propionate;
methyl 3-(5-acetamido-1,3-dioxoisoindolin-2-yl)-3-(3-ethoxy-4-methoxyphenyl)propionate;
methyl 3-(4-acetamido-1,3-dioxoisoindolin-2-yl)-3-(3-(benzyloxy)-4-methoxyphenyl)propionate;
methyl 3-(4-(N-methyl-tert-butoxycarbonylamino)-1,3-dioxoisoindolin-2-yl)-3-(3-ethoxy-4-methoxyphenyl)propionate;
methyl 3-(4-(methylamino)-1,3-dioxoisoindolin-2-yl)-3-(3-ethoxy-4-methoxyphenyl)propionate;
methyl 3-(4-acetamido-1,3-dioxoisoindolin-2-yl)-3-(3-propoxy-4-methoxyphenyl)propionate;
methyl 3-(4-acetamido-1,3-dioxoisoindolin-2-yl)-3-(3-cyclopentyloxy-4-methoxyphenyl)propionate;
methyl 3-(4-acetamido-1,3-dioxoisoindolin-2-yl)-3-(3-ethoxy-4-propoxyphenyl)propionate;
methyl 3-(4-hydroxy-1,3-dioxoisoindolin-2-yl)-3-(3-ethoxy-4-methoxyphenyl)propionate;
methyl 3-(4-acetoxy-1,3-dioxoisoindolin-2-yl)-3-(3-ethoxy-4-methoxyphenyl)propionate;
methyl 3-(4-amino-7-hydroxy-1,3-dioxoisoindolin-2-yl)-3-(3-ethoxy-4-methoxyphenyl)propionate;
methyl 3-(4-amino-5-hydroxy-1,3-dioxoisoindolin-2-yl)-3-(3-ethoxy-4-methoxyphenyl)propionate;
methyl 3-(4-acetamido-1,3-dioxoisoindolin-2-yl)-3-(3-hydroxy-4-methoxyphenyl)propionate;
methyl 3-(4-acetamido-1,3-dioxoisoindolin-2-yl)-3-(3-ethoxy-4-(benzyloxy)phenyl)propionate;
methyl 3-(4-acetamido-1,3-dioxoisoindolin-2-yl)-3-(3-ethoxy-4-hydroxyphenyl)propionate;
methyl 3-(4-acetamido-1,3-dioxoisoindolin-2-yl)-3-(3-methoxy-4-(benzyloxy)phenyl)propionate;
methyl 3-(4-acetamido-1,3-dioxoisoindolin-2-yl)-3-(3-methoxy-4-hydroxyphenyl)propionate;
methyl 3-(4-acetamido-1,3-dioxoisoindolin-2-yl)-3-phenylpropionate;
methyl 3-(4-Acetamido-1,3-dioxoisoindolin-2-yl)-3-(3-chlorophenyl)propionate;

methyl 3-(4-acetamido-1,3-dioxoisoindolin-2-yl)-3-(4-ethoxypheny)propionate;
methyl 3-(4-Acetamido-1,3-dioxoisoindolin-2-yl)-3-(4-chlorophenyl)propionate;
methyl 3-(4-(tert-butyloxycarbonylamino)-1,3-dioxoisoindolin-2-yl)-3-(3-ethoxy-4-methoxy phenyl)propionate;
methyl 3-(4-acetamido-1,3-dioxoisoindolin-2-yl)-3-(3-isopropoxy-4-methoxyphenyl)propionate;
methyl 3-(4-acetamido-1,3-dioxoisoindolin-2-yl)-3-(4-(difluoromethoxy)-3-ethoxyphenyl)propionate;
methyl 3-(4-acetamido-1,3-dioxoisoindolin-2-yl)-3-(3-ethoxy-4-(trifluoromethoxy)phenyl)propionate;
methyl 3-(4-acetamido-1,3-dioxoisoindolin-2-yl)-3-(3-(difluoromethoxy)-4-methoxyphenyl)) propionate;
methyl 3-(4-acetamido-1,3-dioxoisoindolin-2-yl)-3-(4-methoxy-3-(trifluoromethoxy)phenyl)propionate;
ethyl (R)-3-(4-acetamido-1,3-dioxoisoindolin-2-yl)-3-(3-ethoxy-4-methoxyphenyl)propionate;
ethyl (S)-3-(4-acetamido-1,3-dioxoisoindolin-2-yl)-3-(3-ethoxy-4-methoxyphenyl)propionate;
methyl (R)-3-(4-acetamido-1,3-dioxoisoindolin-2-yl)-3-(3-isopropoxy-4-methoxyphenyl)propionate;
methyl (S)-3-(4-acetamido-1,3-dioxoisoindolin-2-yl)-3-(3-isopropoxy-4-methoxyphenyl)propionate;
methyl 3-(4-acetamido-1,3-dioxoisoindolin-2-yl)-3-(benzo[d][1,3]dioxol-5-yl)propionate; and
methyl 3-(4-acetamido-1,3-dioxoisoindolin-2-yl)-3-(2,3-dihydrobenzo[b][1,4]dioxin-6-yl)propionate.

In yet another aspect, the present disclosure is related to a pharmaceutical composition comprising a compound of formula (II), a stereoisomer thereof, or a pharmaceutically acceptable salt thereof and a pharmaceutically acceptable carrier, diluent or excipient:

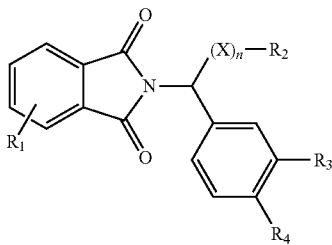

formula (II)

wherein
$R_1$ represents one or more identical or different substituents selected from the group consisting of halogen, hydroxy, optionally substituted hydrocarbyl, optionally substituted amino, optionally substituted hydrocarbylcarbonylamino, optionally substituted hydrocarbylcarbonyloxy, optionally substituted hydrocarbyloxycarbonylamino and optionally substituted hydrocarbylcarbonylamino;
$R_2$ is selected from the group consisting of optionally substituted hydrocarbyloxycarbonyl and carboxyl;
$R_3$ is selected from the group consisting of hydrogen, halogen, hydroxy, optionally substituted hydrocarbyloxy, optionally substituted arylhydrocarbyloxy and optionally substituted cyclohydrocarbyloxy;
$R_4$ is selected from the group consisting of hydrogen, halogen, hydroxy, optionally substituted hydrocarbyloxy, optionally substituted arylhydrocarbyloxy and optionally substituted cyclohydrocarbyloxy; and
X is —$CR_5R_6$—, wherein if $R_5$ is selected from the group consisting of hydrogen, halogen, optionally substituted hydrocarbyl, optionally substituted cyclohydrocarbyl, optionally substituted aryl and optionally substituted heteroaryl; and $R_6$ is selected from the group consisting of hydrogen, halogen, optionally substituted hydrocarbyl, optionally substituted cyclohydrocarbyl, optionally substituted aryl and optionally substituted heteroaryl, n is 0, 1, 2, 3 or 4; and if $R_5$ and $R_6$ together with a carbon atom to which they are attached form an optionally substituted cyclohydrocarbyl, n is 1.

In another aspect, the present disclosure relates to a method for treating or preventing a disease associated with immunoglobulin E (IgE), preferably mediated by immunoglobulin E (IgE), comprising administering a therapeutically effective amount of a compound of formula (II), a stereoisomer thereof, or a pharmaceutically acceptable salt thereof, or a therapeutically effective amount of a pharmaceutical composition comprising a compound of formula (II), a stereoisomer thereof, or a pharmaceutically acceptable salt thereof and a pharmaceutically acceptable carrier, diluent or excipient to a subject in need thereof:

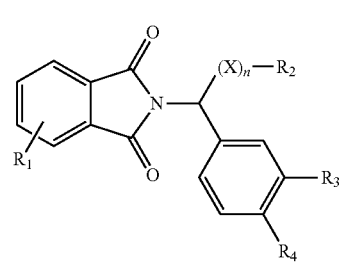

formula (II)

wherein
$R_1$ represents one or more identical or different substituents selected from the group consisting of halogen, hydroxy, optionally substituted hydrocarbyl, optionally substituted amino, optionally substituted hydrocarbylcarbonylamino, optionally substituted hydrocarbylcarbonyloxy, optionally substituted hydrocarbyloxycarbonylamino and optionally substituted hydrocarbylcarbonylamino;
$R_2$ is selected from the group consisting of optionally substituted hydrocarbyloxycarbonyl and carboxyl;
$R_3$ is selected from the group consisting of hydrogen, halogen, hydroxy, optionally substituted hydrocarbyloxy, optionally substituted arylhydrocarbyloxy and optionally substituted cyclohydrocarbyloxy;
$R_4$ is selected from the group consisting of hydrogen, halogen, hydroxy, optionally substituted hydrocarbyloxy, optionally substituted arylhydrocarbyloxy and optionally substituted cyclohydrocarbyloxy; and
X is —$CR_5R_6$—, wherein if $R_5$ is selected from the group consisting of hydrogen, halogen, optionally substituted hydrocarbyl, optionally substituted cyclohydrocarbyl, optionally substituted aryl and optionally substituted heteroaryl; and $R_6$ is selected from the group consisting of hydrogen, halogen, optionally substituted hydrocarbyl, optionally substituted cyclohydrocarbyl, optionally substituted aryl and optionally substituted heteroaryl, n is 0, 1, 2, 3 or 4; and if $R_5$ and $R_6$ together with a carbon atom to which they are attached form an optionally substituted cyclohydrocarbyl, n is 1.

In yet another aspect, the present disclosure relates to a compound of formula (II), a stereoisomer thereof, or a pharmaceutically acceptable salt thereof for treating or preventing a disease associated with immunoglobulin E (IgE), preferably mediated by immunoglobulin E (IgE):

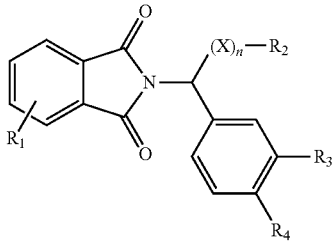

formula (II)

wherein

R₁ represents one or more identical or different substituents selected from the group consisting of halogen, hydroxy, optionally substituted hydrocarbyl, optionally substituted amino, optionally substituted hydrocarbylcarbonylamino, optionally substituted hydrocarbylcarbonyloxy, optionally substituted hydrocarbyloxycarbonylamino and optionally substituted hydrocarbylcarbonylamino;

R₂ is selected from the group consisting of optionally substituted hydrocarbyloxycarbonyl and carboxyl;

R₃ is selected from the group consisting of hydrogen, halogen, hydroxy, optionally substituted hydrocarbyloxy, optionally substituted arylhydrocarbyloxy and optionally substituted cyclohydrocarbyloxy;

R₄ is selected from the group consisting of hydrogen, halogen, hydroxy, optionally substituted hydrocarbyloxy, optionally substituted arylhydrocarbyloxy and optionally substituted cyclohydrocarbyloxy; and X is —CR₅R₆—, wherein if R₅ is selected from the group consisting of hydrogen, halogen, optionally substituted hydrocarbyl, optionally substituted cyclohydrocarbyl, optionally substituted aryl and optionally substituted heteroaryl; and R₆ is selected from the group consisting of hydrogen, halogen, optionally substituted hydrocarbyl, optionally substituted cyclohydrocarbyl, optionally substituted aryl and optionally substituted heteroaryl, n is 0, 1, 2, 3 or 4; and if R₅ and R₆ together with a carbon atom to which they are attached form an optionally substituted cyclohydrocarbyl, n is 1.

In still yet another aspect, the present disclosure relates to a pharmaceutical composition for treating or preventing a disease associated with immunoglobulin E (IgE), preferably mediated by immunoglobulin E (IgE) comprising a therapeutically effective amount of a compound of formula (II), a stereoisomer thereof, or a pharmaceutically acceptable salt thereof and a pharmaceutically acceptable carrier, diluent or excipient:

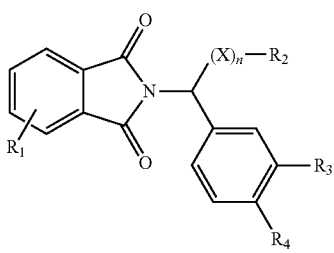

formula (II)

wherein

R₁ represents one or more identical or different substituents selected from the group consisting of halogen, hydroxy, optionally substituted hydrocarbyl, optionally substituted amino, optionally substituted hydrocarbylcarbonylamino, optionally substituted hydrocarbylcarbonyloxy, optionally substituted hydrocarbyloxycarbonylamino and optionally substituted hydrocarbylcarbonylamino;

R₂ is selected from the group consisting of optionally substituted hydrocarbyloxycarbonyl and carboxyl;

R₃ is selected from the group consisting of hydrogen, halogen, hydroxy, optionally substituted hydrocarbyloxy, optionally substituted arylhydrocarbyloxy and optionally substituted cyclohydrocarbyloxy;

R₄ is selected from the group consisting of hydrogen, halogen, hydroxy, optionally substituted hydrocarbyloxy, optionally substituted arylhydrocarbyloxy and optionally substituted cyclohydrocarbyloxy; and X is —CR₅R₆—, wherein if R₅ is selected from the group consisting of hydrogen, halogen, optionally substituted hydrocarbyl, optionally substituted cyclohydrocarbyl, optionally substituted aryl and optionally substituted heteroaryl; and R₆ is selected from the group consisting of hydrogen, halogen, optionally substituted hydrocarbyl, optionally substituted cyclohydrocarbyl, optionally substituted aryl and optionally substituted heteroaryl, n is 0, 1, 2, 3 or 4; and if R₅ and R₆ together with a carbon atom to which they are attached form an optionally substituted cyclohydrocarbyl, n is 1.

In another aspect, the present disclosure relates to a compound of formula (II), a stereoisomer thereof, or a pharmaceutically acceptable salt thereof for treating or preventing dermatosis, psoriasis, eczema, atopic dermatitis, urticaria, asthma, asthma-chronic obstructive pulmonary disease (COPD) overlap syndrome (ACOS), allergic rhinitis, seasonal allergic rhinitis, drug-induced interstitial lung disease, bronchopulmonary aspergillosis, leprosy, pemphigoid and parasitic infections:

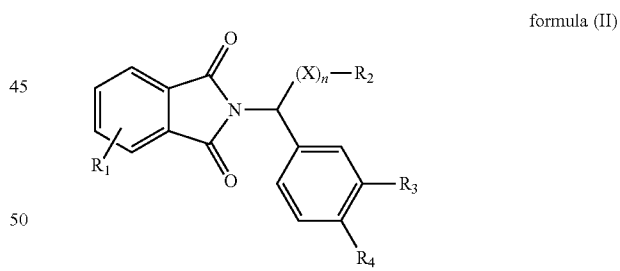

formula (II)

wherein

R₁ represents one or more identical or different substituents selected from the group consisting of halogen, hydroxy, optionally substituted hydrocarbyl, optionally substituted amino, optionally substituted hydrocarbylcarbonylamino, optionally substituted hydrocarbylcarbonyloxy, optionally substituted hydrocarbyloxycarbonylamino and optionally substituted hydrocarbylcarbonylamino;

R₂ is selected from the group consisting of optionally substituted hydrocarbyloxycarbonyl and carboxyl;

R₃ is selected from the group consisting of hydrogen, halogen, hydroxy, optionally substituted hydrocarbyloxy, optionally substituted arylhydrocarbyloxy and optionally substituted cyclohydrocarbyloxy;

R4 is selected from the group consisting of hydrogen, halogen, hydroxy, optionally substituted hydrocarbyloxy, optionally substituted arylhydrocarbyloxy and optionally substituted cyclohydrocarbyloxy; and X is —CR5R6—, wherein if R5 is selected from the group consisting of hydrogen, halogen, optionally substituted hydrocarbyl, optionally substituted cyclohydrocarbyl, optionally substituted aryl and optionally substituted heteroaryl; and R6 is selected from the group consisting of hydrogen, halogen, optionally substituted hydrocarbyl, optionally substituted cyclohydrocarbyl, optionally substituted aryl and optionally substituted heteroaryl, n is 0, 1, 2, 3 or 4; and if R5 and R6 together with a carbon atom to which they are attached form an optionally substituted cyclohydrocarbyl, n is 1.

In yet another aspect, the present disclosure relates to a compound of formula (II), a stereoisomer thereof or a pharmaceutically acceptable salt thereof for treating or preventing dermatosis, psoriasis, eczema, atopic dermatitis, urticaria, asthma, asthma-chronic obstructive pulmonary disease (COPD) overlap syndrome (ACOS), allergic rhinitis, seasonal allergic rhinitis, drug-induced interstitial lung disease, bronchopulmonary aspergillosis, leprosy, pemphigoid, and parasitic infection associated with immunoglobulin E (IgE), preferably mediated by immunoglobulin E (IgE):

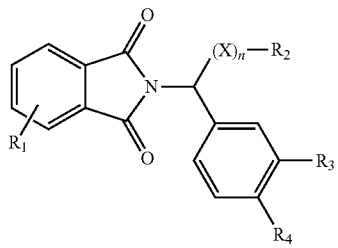

formula (II)

wherein

R1 represents one or more identical or different substituents selected from the group consisting of halogen, hydroxy, optionally substituted hydrocarbyl, optionally substituted amino, optionally substituted hydrocarbylcarbonylamino, optionally substituted hydrocarbylcarbonyloxy, optionally substituted hydrocarbyloxycarbonylamino and optionally substituted hydrocarbylcarbonylamino;

R2 is selected from the group consisting of optionally substituted hydrocarbyloxycarbonyl and carboxyl;

R3 is selected from the group consisting of hydrogen, halogen, hydroxy, optionally substituted hydrocarbyloxy, optionally substituted arylhydrocarbyloxy and optionally substituted cyclohydrocarbyloxy;

R4 is selected from the group consisting of hydrogen, halogen, hydroxy, optionally substituted hydrocarbyloxy, optionally substituted arylhydrocarbyloxy and optionally substituted cyclohydrocarbyloxy; and X is —CR5R6—, wherein if R5 is selected from the group consisting of hydrogen, halogen, optionally substituted hydrocarbyl, optionally substituted cyclohydrocarbyl, optionally substituted aryl and optionally substituted heteroaryl; and R6 is selected from the group consisting of hydrogen, halogen, optionally substituted hydrocarbyl, optionally substituted cyclohydrocarbyl, optionally substituted aryl and optionally substituted heteroaryl, n is 0, 1, 2, 3 or 4; and if R5 and R6 together with a carbon atom to which they are attached form an optionally substituted cyclohydrocarbyl, n is 1.

In still yet another aspect, the present disclosure relates to a process for preparing a compound of formula (II), a stereoisomer thereof or a pharmaceutically acceptable salt thereof, comprising:

(1) reacting a compound of formula (B-I) with malonic acid and ammonium acetate to obtain a compound of formula (B-II),

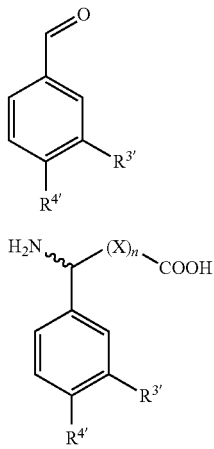

formula (B-I)

formula (B-II)

wherein groups represented by R3' and R4' in formula (B-I) and formula (B-II) have the same definitions as R3 and R4 in formula (II), (2) esterifying the compound of formula (B-II) with alcohol to obtain a compound of formula (B-III),

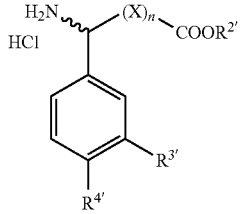

formula (B-III)

wherein groups represented by R3' and R4' in formula (B-II) and formula (B-III) have the same definitions as R3 and R4 in formula (II), and R2' is selected from the group consisting of hydrogen and hydrocarbyl; and (3) reacting a compound of formula (B-IV) with the compound of formula (B-III) to obtain the compound of formula (II)

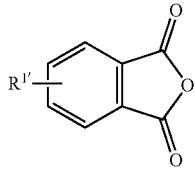

formula (B-IV)

wherein groups represented by R1', R3' and R4' in formula (B-III) and formula (B-IV) have the same definitions as R1, R3 and R4 in formula (II), and R2' is selected from the group consisting of hydrogen and hydrocarbyl;

wherein X is —$CR_5R_6$—, wherein $R_5$ is hydrogen, $R_6$ is hydrogen and n is 1.

DETAILED DESCRIPTION

Figure 1:
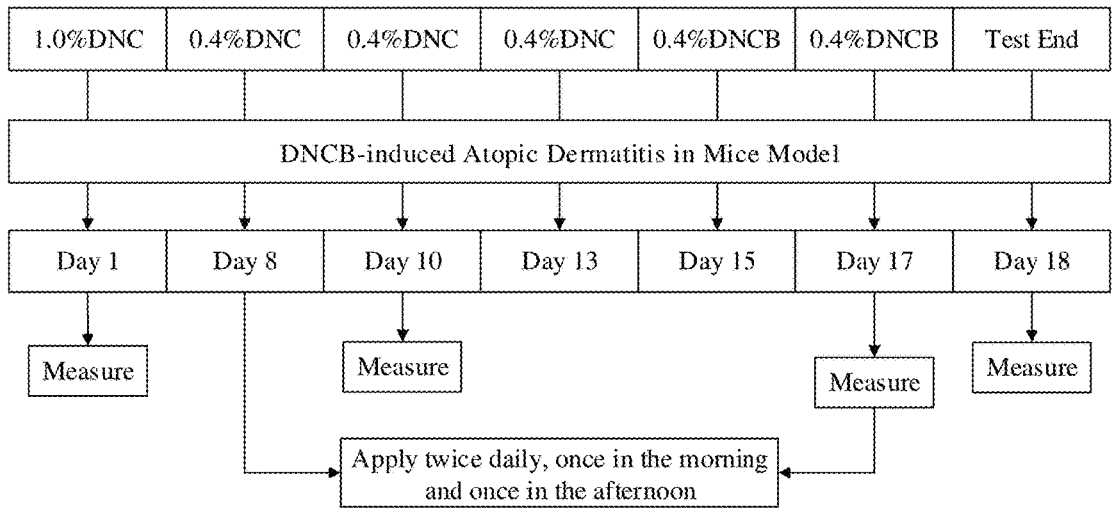
FIG. 1 shows a method of induction on and administration to model animals in Biological Example 1 of the present disclosure.

In the following description, certain specific details are shown to provide a thorough understanding for various disclosed embodiments. One skilled in the relevant art, however will recognize that the embodiments can be practiced without one or more these specific details, or with other methods, components materials, etc.

Unless the context required otherwise, throughout the specification and claims which follows. the term "comprise" and variations thereof, such as "comprises" and "comprising" are to be construed in an open, inclusive sense which is as "include, but not limited to".

Reference throughout this specification to "one embodiment" or "an embodiment" or "in another embodiment", or "in some embodiments" means that a particular referent feature structure or characteristic described in connection with the embodiments is included in at least one embodiment. Therefore, the appearance of the phrases "in one embodiment", "in the embodiment", "in another embodiment", or "in some embodiments" in various places throughout this specification are not necessarily all referring to the same embodiment. Moreover, the particular features structures or characteristics can be combined in any suitable manner in one or more embodiments.

It should be noted that, as used in this specification and the appended claims, the singular forms "a", "an" and "the" comprise plural referents unless the context clearly stated otherwise. Therefore, for example, a pharmaceutical composition comprising "a compound of formula (II), a stereoisomer thereof, or a pharmaceutically acceptable salt thereof" comprises one compound of formula (II), a stereoisomer thereof or a pharmaceutically acceptable salt thereof, or two or more compounds of formula (II), stereoisomers thereof, or pharmaceutically acceptable salts thereof.

Definition

Accordingly, as used in the specification and appended claims, unless specified to the contrary, the following terms have the meaning indicated:

Certain chemical groups named herein are preceded by a shorthand notation indicating the total number of carbon atoms that are to be found in the indicated chemical group. For example, $C_1$-$C_4$alkyl describes an alkyl group, as defined below, having a total of 1 to 4 carbon atoms, and $C_3$-$C_{10}$cycloalkyl describes a cycloalkyl group having a total of 3 to 10 carbon atoms as defined below. The total number of carbon atoms in the shorthand notation does not include the carbons that can exist in the substituents of the groups described.

As used herein, the term "halogen" refers to fluorine, chlorine, bromine or iodine.

As used herein, the term "hydroxy" refers to —OH group.

As used herein, the term "amino" refers to —$NH_2$ group.

As used herein, the term "carboxyl" refers to —COOH group.

As used herein, the term "hydrocarbyl" refers to the aliphatic hydrocarbyl group. The hydrocarbyl moiety can be a "saturated hydrocarbyl" group, meaning that it does not contain any alkene or alkyne moieties. The hydrocarbyl moiety can also be an "unsaturated hydrocarbyl" moiety, meaning that it contains at least one alkene or alkyne moiety. An "alkene" moiety refers to a group consisting of two to eight carbon atoms and at least one carbon-carbon double bond, which is attached to the rest of the molecule by a single bond, e.g., ethenyl, prop-1-enyl, but-1-enyl, pent-1-enyl, penta-1,4-dienyl, and the like. An "alkyne" moiety refers to a straight or branched hydrocarbon chain group consisting of two to eight carbon atoms and at least one carbon-carbon triple bond, which is attached to the rest of the molecule by a single bond. The hydrocarbyl group, whether saturated or unsaturated, may be branched or linear.

The hydrocarbyl group may have one to eight carbon atoms (whenever it appears herein, a numerical range such as "one to eight" refers to each integer in the given number range; e.g. "1 to 8" means that the hydrocarbyl group may consist of one carbon atom, two carbon atoms, three carbon atoms, four carbon atoms, etc., up to and including eight carbon atoms, although the present definition also covers the occurrence of term "hydrocarbyl" where no numerical range is designated).

The hydrocarbyl group may be optionally substituted, i.e. substituted or unsubstituted. When substituted, the substituted group(s) is(are) individually and independently selected from the group consisting of cyclohydrocarbyl, aryl, heteroaryl, heteroalicyclyl, hydroxy, hydrocarbyloxy, aryloxy, mercapto, allkylthio, arylthio, cyano, halo, carbonyl, thiocarbonyl, O-carbamyl, N-carbamyl, O-thiocarbamyl, N-thiocarbamyl, C-amido, N-amido, S-sulfinamido, N-sulfinamido, C-carboxyl, O-carboxyl, isocyanato, thiocyano, isothiocyanato, nitro, silyl, trihalomethanesulfonyl, —NR'R"(R' and R" are hydrocarbyl group defined herein) or amino comprising mono- and bi-substituted amino group, and the protected derivatives thereof. Typical hydrocarbyl groups comprise, but are not limited to, methyl, ethyl, propyl, isopropyl, butyl, isobutyl, t-butyl, pentyl, hexyl, ethenyl, propenyl, butenyl, ethynyl, propynyl and butynyl. Whenever a substituent is described as being "optionally substituted", that substituent may be substituted with one of the above substituents.

In some embodiments, "$C_1$-$C_4$hydrocarbyl" refers to an hydrocarbyl group as defined above containing one to four carbon atoms. $C_1$-$C_4$hydrocarbyl group may be optionally substituted as defined for hydrocarbyl group.

In some embodiments, "$C_1$-$C_6$hydrocarbyl" refers to an hydrocarbyl group as defined above containing one to six carbon atoms. $C_1$-$C_6$hydrocarbyl group may be optionally substituted as defined for hydrocarbyl group.

In some embodiments, "$C_1$-$C_{12}$hydrocarbyl" refers to an hydrocarbyl group as defined above containing one to twelve carbon atoms. $C_1$-$C_{12}$hydrocarbyl group may be optionally substituted as defined for hydrocarbyl group.

In some embodiments, "$C_2$-$C_6$hydrocarbyl" refers to an hydrocarbyl group as defined above containing two to six carbon atoms. $C_2$-$C_6$hydrocarbyl group may be optionally substituted as defined for hydrocarbyl group.

In some embodiments, "$C_3$-$C_6$hydrocarbyl" refers to an hydrocarbyl as defined above containing three to six carbon atoms. $C_3$-$C_6$hydrocarbyl group may be optionally substituted as defined for hydrocarbyl group.

In some embodiments, "$C_3$-$C_{12}$hydrocarbyl" refers to an hydrocarbyl as defined above containing three to twelve carbon atoms. $C_3$-$C_{12}$hydrocarbyl group may be optionally substituted as defined for hydrocarbyl group.

In some embodiments, "$C_6$-$C_{12}$hydrocarbyl" refers to an hydrocarbyl as defined above containing six to twelve carbon atoms. $C_6$-$C_{12}$hydrocarbyl group may be optionally substituted as defined for hydrocarbyl group.

In some embodiments, "$C_7$-$C_{12}$hydrocarbyl" refers to an hydrocarbyl as defined above containing seven to twelve carbon atoms. $C_7$-$C_{12}$hydrocarbyl group may be optionally substituted as defined for hydrocarbyl group.

As used herein, the term "hydrocarbyloxy" refers to the formula —O-hydrocarbyl, wherein hydrocarbyl group is defined as herein. Exemplary examples of hydrocarbyloxy include, but are not limited to, methoxy, ethoxy, n-propoxy, 1-methylethoxy(isopropoxy), n-butoxy, isobutoxy, sec-butoxy, t-butoxy, amoxy and t-amoxy.

As used herein, the term "aryl" refers to a carbocycle (full carbon) or two or more fused rings (rings sharing with two adjacent carbon atoms), having completely delocalized Pi electron system. Examples of aryl group include, but are not limited to, fluorenyl, phenyl and naphthyl. The aryl group may have, for example, five to twelve carbon atoms. The aryl group of the present disclosure may be substituted or unsubstituted. Where substituted, hydrogen atom(s) is(are) substituted with one or more substituents independently selected from the group consisting of hydrocarbyl, cyclohydrocarbyl, aryl, heteroaryl, heteroalicyclyl, hydroxy, protected hydroxy, hydrocarbyloxy, aryloxy, mercapto, hydrocarbylthio, arylthio, cyano, halo, carbonyl, thiocarbonyl, O-carbamyl, N-carbamyl, O-thiocarbamyl, N-thiocarbamyl, C-amido, N-amido, S-sulfinamido, N-sulfinamido, C-carboxyl, protected C-carboxyl, O-carboxyl, isocyanato, thiocyano, isothiocyanato, nitro, silyl, trihalomethanesulfonyl, —NR'R" (R' and R" are hydrocarbyl groups defined herein) and protected amino. Whenever a substituent is described as being "optionally substituted", that substituent may be substituted with one of the above substituents.

As used herein, the term "arylhydrocarbyloxy" refers to a group of the formula —O-hydrocarbylaryl, where the aryl and the hydrocarbyl are as defined herein. Examples of arylhydrocarbylyoxy include, but are not limited to, benzyloxy, phenethyloxy and phenylpropyloxy.

In some embodiments, "$C_6$-$C_{16}$arylhydrocarbyloxy" refers to an arylhydrocarbyloxy as defined above containing six to sixteen carbon atoms. $C_6$-$C_{16}$arylhydrocarbyloxy group may be optionally substituted as defined above for aryl group and hydrocarbyl group.

In some embodiments, "$C_6$-$C_{18}$arylhydrocarbyloxy" refers to an arylhydrocarbyloxy as defined above containing six to eighteen carbon atoms. $C_6$-$C_{18}$arylhydrocarbyloxy group may be optionally substituted as defined above for aryl group and hydrocarbyl group.

In some embodiments, "$C_7$-$C_{18}$arylhydrocarbyloxy" refers to an arylhydrocarbyloxy as defined above containing seven to eighteen carbon atoms. $C_7$-$C_{18}$arylhydrocarbyloxy group may be optionally substituted as defined above for aryl group and hydrocarbyl group.

In some embodiments, "$C_8$-$C_{18}$arylhydrocarbyloxy" refers to an arylhydrocarbyloxy as defined above containing eight to eighteen carbon atoms. $C_8$-$C_{18}$arylhydrocarbyloxy group may be optionally substituted as defined above for aryl group and hydrocarbyl group.

In some embodiments, "$C_8$-$C_{24}$arylhydrocarbyloxy" refers to an arylhydrocarbyloxy as defined above containing eight to twenty-four carbon atoms. $C_8$-$C_{24}$arylhydrocarbyloxy group may be optionally substituted as defined above for aryl group and hydrocarbyl group.

In some embodiments, "$C_{11}$-$C_{24}$arylhydrocarbyloxy" refers to an arylhydrocarbyloxy as defined above containing eleven to twenty-four carbon atoms. $C_{11}$-$C_{24}$arylhydrocarbyloxy group may be optionally substituted as defined above for aryl group and hydrocarbyl group.

In some embodiments, "$C_{12}$-$C_{24}$arylhydrocarbyloxy" refers to an arylhydrocarbyloxy as defined above containing twelve to twenty-four carbon atoms. $C_{12}$-$C_{24}$arylhydrocarbyloxy group may be optionally substituted as defined above for aryl group and hydrocarbyl group.

In some embodiments, "$C_6$-$C_{24}$arylhydrocarbyloxy" refers to an arylhydrocarbyloxy as defined above containing six to twenty-four carbon atoms. $C_6$-$C_{24}$arylhydrocarbyloxy group may be optionally substituted as defined above for aryl group and hydrocarbyl group.

As used herein, the term "heteroaryl" refers to a five- to eighteen-membered aromatic ring group, containing one to seventeen carbon atoms and one to ten heteroatoms selected from the group consisting of nitrogen, oxygen and sulphur. In some embodiments, the heteroaryl may be monocyclic, bicyclic, tricyclic or tetracyclic ring system, which may comprise fused or bridged ring system. Moreover, nitrogen, carbon or sulphur atom in the heteroaryl group may be optionally oxidized, and the nitrogen atom may be optionally quaternized. Exemplary examples of heteroaryl include, but are not limited to, azepinyl, acridinyl, benzimidazolyl, benzothiazolyl, benzoindolyl, benzodioxolanyl, benzofuranyl, benzoxazolyl, benzothiazolyl, benzothiadiazolyl, benzo[b][1,4]dioxepanyl, 1,4-benzodioxanyl, benzonaphthofuranyl, benzodioxolanyl, benzodioxadienyl, benzopyranyl, benzopyronyl, benzofuranyl, benzofuranonyl, benzothienyl, benzotriazolyl, benzo[4,6]imidazo[1,2-a]pyridyl, carbazolyl, cinnolinyl, dibenzofuranyl, dibenzothienyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyl, naphthyridinyl, oxadiazolyl, 2-oxoazepinyl, oxazolyl, oxiranyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, pyrrolyl, quinazolinyl, quinoxalinyl, quinolyl, quinuclidinyl, isoquinolyl, tetrahydroquinolyl, thiazolyl, thiadiazolyl, triazolyl, tetrazolyl, triazinyl and thiophenyl. The aryl group of the present disclosure may be substituted or unsubstituted. Where substituted, hydrogen atom(s) is(are) substituted with one or more substituents independently selected from the group consisting of hydrocarbyl, cyclohydrocarbyl, aryl, heteroaryl, heteroalicyclyl, hydroxy, protected hydroxy, hydrocarbyloxy, aryloxy, mercapto, hydrocarbylthio, arylthio, cyano, halo, carbonyl, thiocarbonyl, O-carbamyl, N-carbamyl, O-thiocarbamyl, N-thiocarbamyl, C-amido, N-amido, S-sulfinamido, N-sulfinamido, C-carboxyl, protected C-carboxyl, O-carboxyl, isocyanato, thiocyano, isothiocyanato, nitro, silyl, trihalomethanesulfonyl, —NR'R" (R' and R" are hydrocarbyl groups defined herein) and protected amino. Whenever a substituent is described as being "optionally substituted", that substituent may be substituted with one of the above substituents.

As used herein, the term "cyclohydrocarbyl" refers to stable non-aromatic monocyclic or bicyclohydrocarbyls composed of only carbon and hydrogen atoms, having three to fifteen carbon atoms, and in some embodiments having three to twelve carbon atoms, which are saturated or unsaturated and connected to the rest of the molecule through a single bond, such as cyclopropyl, cyclobutyl, cyclopentyl, cyclohexyl, cyclodecyl, etc. Unless stated otherwise specifically in the specification, the term "cyclohydrocarbyl" is meant to include the cyclohydrocarbyl groups as defined above, which may be optionally substituted with one or more substituents selected from the group consisting of cyclohydrocarbyl, aryl, heteroaryl, heteroalicyclyl, hydroxy, hydrocarbyloxy, aryloxy, mercapto, hydrocarbylthio, arylthio, cyano, halo, carbonyl, thiocarbonyl, O-carbamyl, N-carbamyl, O-thiocarbamyl, N-thiocarbamyl, C-amido, N-amido, S-sulfinamido, N-sulfinamido, C-carboxyl, O-carboxyl, isocyanato, thiocyano, isothiocyanato, nitro, silyl, trihalomethanesulfonyl, —NR'R" (R' and R" are hydrocarbyl groups defined in the present disclosure) or amino comprising mono- and di-substituted amino group, and the protected derivatives thereof.

In some embodiments, "$C_3$-$C_6$cyclohydrocarbyl" refers to a cyclohydrocarbyl as defined above containing three to six carbon atoms. $C_3$-$C_6$cyclohydrocarbyl group may be optionally substituted as defined above for cyclohydrocarbyl group.

In some embodiments, "$C_3$-$C_{10}$cyclohydrocarbyl" refers to a cyclohydrocarbyl as defined above containing three to ten carbon atoms. $C_3$-$C_{10}$cyclohydrocarbyl group may be optionally substituted as defined above for cyclohydrocarbyl group.

In some embodiments, "$C_3$-$C_{12}$cyclohydrocarbyl" refers to a cyclohydrocarbyl as defined above containing three to twelve carbon atoms. $C_3$-$C_{12}$cyclohydrocarbyl group may be optionally substituted as defined above for cyclohydrocarbyl group.

As used herein, the term "cyclohydrocarbyloxy" refers to the formula —O-cyclohydrocarbyl, wherein cyclohydrocarbyl group is defined as herein. Exemplary examples of cyclohydrocarbyloxyl include, but are not limited to, cyclopropyloxy, cyclobutyloxy, cyclopentyloxy, cyclohexyloxy and cyclodecyloxy.

As used herein, the term "hydrocarbylcarbonylamino" refers to the formula —NHC(=O)-hydrocarbyl, wherein hydrocarbyl group is defined as herein. Exemplary examples of hydrocarbylcarbonylamino include, but are not limited to, acetylamino, propionylamino, butyrylamino and valerylamino As used herein, the term "hydrocarbylcarbonyloxy" refers to the formula —OC(=O)-hydrocarbyl, wherein hydrocarbyl group is defined as herein. Exemplary examples of hydrocarbylcarbonyloxy include, but are not limited to, acetoxy, propionyloxy, butyryloxy and valeryloxy.

As used herein, the term "hydrocarbyloxycarbonylamino" refers to the formula —NHC(=O)-hydrocarbyl, wherein hydrocarbyl group is defined as herein. Exemplary examples of hydrocarbyloxycarbonylamino include, but are not limited to, methoxycarbonylamino, ethoxycarbonylamino, propoxycarbonylamino and tert-butoxycarbonylamino.

As used herein, the term "hydrocarbyloxycarbonyl" refers to the formula —OC(=O)-hydrocarbyl, wherein hydrocarbyl group is defined as herein. Exemplary examples of hydrocarbyloxycarbonyl include, but are not limited to, methoxycarbonyl, ethoxycarbonyl, propoxycarbonyl, isopropoxycarbonyl and butoxycarbonyl.

As used herein, the term "a compound of the present disclosure, a stereoisomer thereof or a pharmaceutically acceptable salt thereof" refers to a compound of the formula (I) of the present disclosure, a stereoisomer thereof and a pharmaceutically acceptable salt thereof, a compound of formula (II), a stereoisomer thereof and a pharmaceutically acceptable salt thereof, and any specific compounds falling within formula (I) and formula (II), stereoisomers thereof and pharmaceutically acceptable salts thereof.

As used herein, the term "mammal" means animals including, for example, dogs, cats, cows, sheep, horses, and humans. In some embodiments, mammals include humans.

As used herein, the term "patient" means an animal, such as a human, a companion animal, such as a dog, cat and horse, and livestock, such as cattle, swine and sheep. In some embodiments, patients are mammals, including both males and females. In some embodiments, patients are humans.

As used herein, the term "pharmaceutically acceptable" means the carrier, vehicle, diluent, excipient and/or salt must be compatible with the other ingredients of the formulation, and not deleterious to the recipient thereof.

As used herein, the term "optional" or "optionally" means that the subsequently described event of circumstances may or may not occur, and that the description includes instances where said event or circumstance occurs and instances in which it does not.

As used herein, the term "pharmaceutically acceptable carrier, diluent or excipient" comprises without limitation any adjuvant, carrier, excipient, glidant, sweetening agent, diluent, preservative, dye/colorant, flavor enhancer, surfactant, wetting agent, dispersing agent, suspending agent, stabilizer, isosmotic agent, solvent, or emulsifier, etc, which has been approved by the United States Food and Drug Administration as being acceptable for use in humans or animals and have no side effects on preparing a pharmaceutical composition.

As used herein, the term "carrier" is defined as one that facilitates the introduction of a compound into a cell or tissue. For example, dimethyl sulfoxide (DMSO) is commonly used as a carrier because it is easy to introduce certain organic compounds into cells or tissues of an organism.

As used herein, the term "pharmaceutically acceptable salts" include both "pharmaceutically acceptable acid addition salts" and "pharmaceutically acceptable base addition salts".

As used herein, the term "pharmaceutically acceptable acid addition salt" refers to those salts which retain the biological effectiveness and properties of the free bases, which are not biologically or otherwise undesirable, and which are formed with inorganic acids such as, but not limited to hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphanic acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleinic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid and the like.

As used herein, the term "pharmaceutically acceptable base addition salt" refers to those salts which retain the biological effectiveness and properties of the free acids, which are not biologically or otherwise undesirable. These salts are prepared from addition of an inorganic or an organic base to the free acid. Salts derived from inorganic bases include, but are not limited, to sodium, potassium, lithium, ammonium, calcium, magnesium, iron, zinc, copper, manganese, aluminum salts and the like. In some embodiments, inorganic salts are the ammonium, sodium, potassium, calcium, and magnesium salts. Salts derived from organic bases include, but are not limited to, salts of primary, secondary and tertiary amines, substituted amines including naturally occurring substituted amines, cyclic amines and s basic ion exchange resins, such as ammonia, isopropylamine, trimethylamine, diethylamine, triethylamine, tripropylamine, diethanolamine, ethanolamine, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucosamine, theobromine, triethanolamine, trometamol, purine, piperazine, piperidine, N-ethyl piperidine, polyamine resins and the like. In some embodiments, organic bases are isopropylamine, diethylamine, ethanolamine, trimethylamine, dicyclohexylamine, choline and caffeine.

As used herein, the term "a solvent or a solvent mixture" refers to any and all solvents. In some embodiments, a solvent or a solvent mixture is organic solvents and water, which include, but are not limited to, water, methanol, ethanol, 2-propanol, n-butanol, iso-butanol, acetone, methylethylketone, ethylacetate, 1,4-dioxane, diethylether, methyl tert-butyl ether, tetrahydrofuran, acetonitrile, dichloromethane, chloroform, N,N-dimethylformamide, cyclohexane, cyclopentane, n-hexane, n-heptane, n-pentane, toluene, o-xylene, p-xylene, dimethyl sulfoxide (DMSO), pyridine, acetic acid, anisole, butylacetate, cumene, ethylformate, formic acid, iso-butylacetate, iso-propylacetate, methylacetate, 3-methyl-1-butanol, methylisobutylketone, 2-methyl-1-propanol, 1-pentanol, propylacetate, ethylenglycole, and 1-methyl-2-pyrrolidone, as well as any and all mixtures of two or more such solvents. In some embodiments, a solvent or a solvent mixture is a single solvent and a binary mixture. In some embodiments, a solvent or a solvent mixture is water and single solvent of organic solvent and a binary mixture of water and organic solvent.

As used herein, the term "pharmaceutical composition" refers to a formulation of a compound of the present disclosure and a medium generally acceptable in the art for the delivery of the biologically active compound to mammals, e.g., humans. Such a medium includes all pharmaceutically acceptable carriers, diluents or excipients therefor.

As used herein, the term "therapeutically effective amount" refers to an amount of a compound or combination of compounds that ameliorates, attenuates or eliminates a particular disease or condition or a symptom of a particular disease or condition, or prevents or delays the onset of a particular disease or condition or a symptom of a particular disease or condition. The amount of a compound of the present disclosure which constitutes a "therapeutically effective amount" will vary depending on the compound, the condition and its severity, and the age of the mammal to be treated, but can be determined routinely by one of ordinary skill in the art having regard to his own knowledge and to this disclosure.

"Treating" or "treatment", as used herein, covers the treatment of the disease or condition of interest in a mammal, such as a human, having the disease or disorder of interest, and comprises:

(i) preventing the disease or condition from occurring in a mammal, in particular, when such mammal is predisposed to the condition but has not yet been diagnosed as having it;

(ii) inhibiting the disease or condition, i.e., arresting its development; or (iii) relieving the disease or condition, i.e., causing regression of the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

As used herein, the term "physiologically acceptable" refers to a carrier or diluent that does not eliminate the biological activity and properties of the compound.

The compounds of the present disclosure or their pharmaceutically acceptable salts may contain one or more asymmetric centers and may thus give rise to enantiomers, diastereoisomers, and other stereoismeric forms that may be defined, in terms of absolute stereochemistry, as (R)- or (S)-, or (D)- or (L)-for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, the term "stereoisomer" refers to a compound made up of the same atoms bonded by the same bonds but having different three-dimensional structures, which are not interchangeable. The present disclosure contemplates various stereoisomers and mixtures thereof.

Specific Embodiments

In one aspect, the present disclosure relates to a compound of formula (I) and a stereoisomer thereof:

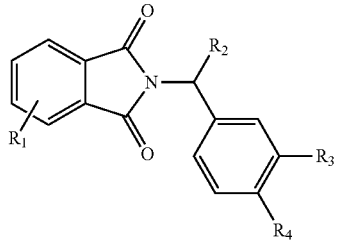

formula (I)

wherein $R_1$ represents one or more substituents selected from the group consisting of hydrogen, halogen, hydroxy, $C_1$-$C_8$hydrocarbyl, amino, $C_1$-$C_8$hydrocarbylcarbonylamino, $C_1$-$C_8$hydrocarbyloxycarbonylamino, amino substituted with one or more $C_1$-$C_4$hydrocarbyl and substituted aminocarbonyl$C_1$-$C_8$hydrocarbyl;

$R_2$ is selected from the group consisting of carboxyl and ester group;

$R_3$ is selected from the group consisting of hydrogen, hydroxy, halogen, $C_1$-$C_8$hydrocarbyloxy, $C_5$-$C_{12}$aryloxy and $C_5$-$C_{12}$cycloaryloxy; and $R_4$ is selected from the group consisting of hydrogen, halogen, hydroxy, $C_1$-$C_8$hydrocarbyloxy and $C_5$-$C_{12}$aryloxy.

In some embodiments, $R_1$ represents one or more substituents selected from the group consisting of hydrogen, halogen, hydroxy, $C_1$-$C_8$alkyl, amino, $C_1$-$C_8$alkylcarbonylamino, $C_1$-$C_8$alkyloxycarbonylamino, amino substituted with one or more $C_1$-$C_4$alkyl and substituted aminocarbonyl$C_1$-$C_8$alkyl;

In some embodiments, $R_3$ is selected from the group consisting of hydrogen, hydroxy, halogen, $C_1$-$C_8$alkyloxy, $C_5$-$C_{12}$aryloxy and $C_5$-$C_{12}$cycloaryloxy.

In some embodiments, $R_4$ is selected from the group consisting of hydrogen, hydroxy, halogen, $C_1$-$C_8$alkyloxy, $C_5$-$C_{12}$aryloxy and $C_5$-$C_{12}$cycloaryloxy.

In some embodiments, $R_1$ is selected from the group consisting of hydrogen, —OH, —F, —Cl, —CH$_3$, —CH$_2$CH$_3$, —CH$_2$CH$_2$CH$_3$, —NH$_2$, —NHCH$_3$, —N(CH$_3$)$_2$, —NHCOCH$_3$, —NHCOOCH$_3$, —NHCOCH$_2$OH, —NHCOCH$_2$Cl, —NHCOCH$_2$F and —NCH$_3$COCH$_3$.

In some embodiments, $R_2$ is selected from the group consisting of —COOH, —COOCH$_3$, —COOCH$_2$CH$_3$, —COOCH$_2$CH$_2$CH$_3$ and —COOCH(CH$_3$)$_2$.

In some embodiments, $R_3$ is selected from the group consisting of hydrogen, hydroxy, halogen, benzyloxy, $C_1$-$C_4$alkyloxy, $C_5$-$C_{12}$aryloxy and $C_5$-$C_{12}$cycloaryloxy.

In some embodiments, $R_3$ is selected from the group consisting of —H, —OH, —Cl, —F, —OCH$_3$, —OCH$_2$CH$_3$, —OCH$_2$CH$_2$CH$_3$, —OCH(CH$_3$)$_2$ and benzyloxy.

In some embodiments, $R_4$ is selected from the group consisting of hydrogen, halogen, hydroxy, $C_1$-$C_4$hydrocarbyloxy, benzyloxy and $C_5$-$C_{12}$aryloxy.

In some embodiments, $R_4$ is selected from the group consisting of —H, —Cl, —F, —OH, —OCH$_3$, —OCH$_2$CH$_3$, —OCH$_2$CH$_2$CH$_3$, —OCH(CH$_3$)$_2$ and benzyloxy.

In another aspect, the present disclosure relates to a pharmaceutical composition comprising a compound of formula (I) or a stereoisomer thereof and a pharmaceutically acceptable carrier:

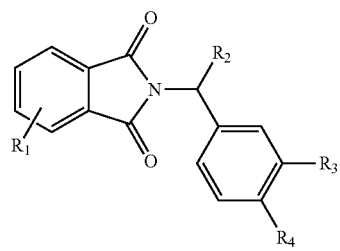

formula (I)

wherein $R_1$ represents one or more substituents selected from the group consisting of hydrogen, halogen, hydroxy, $C_1$-$C_8$hydrocarbyl, amino, $C_1$-$C_8$hydrocarbylcarbonylamino, $C_1$-$C_8$hydrocarbyloxycarbonylamino, amino substituted with one or more $C_1$-$C_4$hydrocarbyl and substituted aminocarbonyl$C_1$-$C_8$hydrocarbyl;

$R_2$ is selected from the group consisting of —COOH, —COOCH$_3$, —COOCH$_2$CH$_3$, —COOCH$_2$CH$_2$CH$_3$ and —COOCH(CH$_3$)$_2$;

$R_3$ is selected from the group consisting of hydrogen, hydroxy, halogen, benzyloxy, $C_1$-$C_4$alkyloxy, $C_5$-$C_{12}$aryloxy and $C_5$-$C_{12}$cycloaryloxy; and $R_4$ is selected from the group consisting of hydrogen, halogen, hydroxy, $C_1$-$C_4$hydrocarbyloxy, benzyloxy and $C_5$-$C_{12}$aryloxy.

In yet another aspect, the present disclosure relates to use of a compound of formula (I) or a stereoisomer thereof, or a pharmaceutical composition comprising a compound of formula (I) or a stereoisomer thereof and a pharmaceutically acceptable carrier thereof in the preparation of a medicament for treating dermatosis psoriasis, eczema and atopic dermatitis:

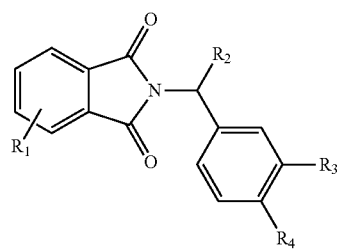

formula (I)

wherein $R_1$ represents one or more substituents selected from the group consisting of hydrogen, halogen, hydroxy, $C_1$-$C_8$hydrocarbyl, amino, $C_1$-$C_8$hydrocarbylcarbonylamino, $C_1$-$C_8$hydrocarbyloxycarbonylamino, amino substituted with one or more $C_1$-$C_4$hydrocarbyl and substituted aminocarbonyl$C_1$-$C_8$hydrocarbyl;

$R_2$ is selected from the group consisting of —COOH, —COOCH$_3$, —COOCH$_2$CH$_3$, —COOCH$_2$CH$_2$CH$_3$ and —COOCH(CH$_3$)$_2$;

$R_3$ is selected from the group consisting of hydrogen, hydroxy, halogen, benzyloxy, $C_1$-$C_4$hydrocarbyloxy, $C_5$-$C_{12}$aryloxy and $C_5$-$C_{12}$cycloaryloxy; and $R_4$ is selected from the group consisting of hydrogen, halogen, hydroxy, $C_1$-$C_4$hydrocarbyloxy, benzyloxy and $C_5$-$C_{12}$aryloxy.

In yet still another aspect, the present disclosure relates to a process for preparing a compound of formula (I) or a stereoisomer thereof:

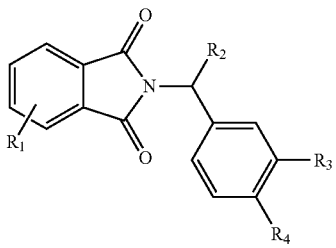

formula (I)

wherein $R_1$ represents one or more substituents selected from the group consisting of hydrogen, halogen, hydroxy, $C_1$-$C_8$hydrocarbyl, amino, $C_1$-$C_8$hydrocarbylcarbonylamino, $C_1$-$C_8$hydrocarbyloxycarbonylamino, amino substituted with one or more $C_1$-$C_4$hydrocarbyl and substituted aminocarbonyl$C_1$-$C_8$hydrocarbyl;

$R_2$ is selected from the group consisting of —COOH, —COOCH$_3$, —COOCH$_2$CH$_3$, —COOCH$_2$CH$_2$CH$_3$ and —COOCH(CH$_3$)$_2$;

$R_3$ is selected from the group consisting of hydrogen, hydroxy, halogen, benzyloxy, $C_1$-$C_4$alkyloxy, $C_5$-$C_{12}$aryloxy and $C_5$-$C_{12}$cycloaryloxy; and $R_4$ is selected from the group consisting of hydrogen, halogen, hydroxy, $C_1$-$C_4$hydrocarbyloxy, benzyloxy and $C_5$-$C_{12}$aryloxy;

wherein the process comprises:

(1) reacting a compound of formula (A-I) with malonic acid and ammonium acetate to obtain a compound of formula (A-II),

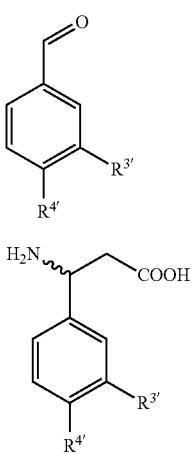

formula (A-I)

formula (A-II)

wherein groups represented by $R^{3'}$ and $R^{4'}$ in formula (A-I) and formula (A-II) have the same definitions as $R_3$ and $R_4$ in the formula (I), (2) esterifying the compound of formula (A-II) with alcohol to obtain a compound of formula (A-III),

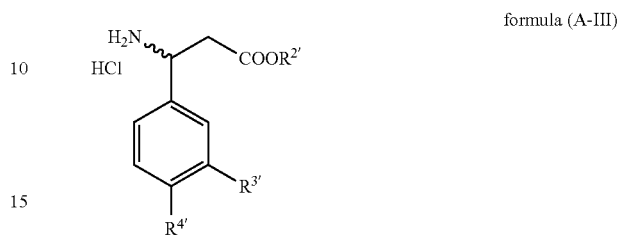

formula (A-III)

wherein groups represented by $R^{3'}$ and $R^{4'}$ in formula (A-II) and formula (A-III) have the same definitions as $R_3$ and $R_4$ in formula (I), and $R^{2'}$ is selected from the group consisting of hydrogen and $C_1$-$C_4$alkyl; and (3) reacting a compound of formula (A-IV) with the compound of formula (A-III) to obtain the compound of formula (I)

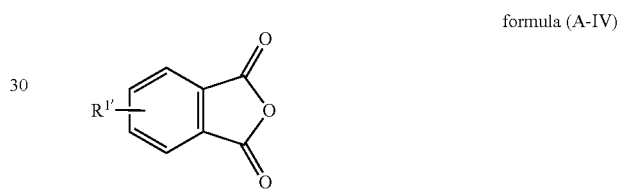

formula (A-IV)

wherein groups represented by $R^{1'}$, $R^{3'}$ and $R^{4'}$ in formula (A-III) and formula (A-IV) have the same definitions as $R_1$, $R_3$ and $R_4$ in formula (I), and $R^{2'}$ is selected from the group consisting of hydrogen and $C_1$-$C_4$alkyl.

In some embodiments, reacting a compound of formula (A-I) with malonic acid and ammonium acetate to obtain a compound of formula (A-II) is carried out in an organic solvent.

In some embodiments, exemplary examples of suitable organic solvents that can be used in the present disclosure to react a compound of formula (A-I) with malonic acid and ammonium acetate to obtain a compound of formula (A-II) include, but are not limited to methanol, ethanol, isopropanol and water.

In some embodiments, a compound of formula (A-I) is reacted with malonic acid and ammonium acetate at about 50° C. to about 130° C. to obtain a compound of formula (A-II).

In some embodiments, exemplary examples of suitable esterifying agents that can be used to prepare a compound of formula (A-III) with a compound of formula (A-II) include, but are not limited to, thionyl chloride, oxalyl chloride, HCl gas and acetyl chloride.

In some embodiments, reacting a compound of formula (A-II) with an alcohol compound to obtain a compound of formula (A-III) is carried out in an organic solvent.

In some embodiments, exemplary examples of suitable organic solvents that can be used in the present disclosure to react a compound of formula (A-II) with an alcohol compound to obtain a compound of formula (A-III) include, but are not limited to, alcohols, tetrahydrofuran, dichloromethane, ethyl acetate and methyl tert-butyl ether.

In some embodiments, exemplary examples of suitable alcohols that can be used in the present disclosure to react a compound of formula (A-II) with an alcohol compound to obtain a compound of formula (A-III) include, but are not limited to methanol, ethanol and isopropanol.

In some embodiments, a compound of formula (A-II) is reacted with an alcohol compound at about −20° C. to about 30° C. to obtain a compound of formula (A-III).

In some embodiments, a catalyst is added in the process for preparing a compound of formula (I) by reacting a compound of formula (A-IV) with a compound of formula (A-III).

In some embodiments, exemplary examples of suitable catalysts that can be used in the present disclosure to react a compound of formula (A-IV) with compound of formula (A-III) to obtain a compound of formula (I) include, but are not limited to, sodium acetate, potassium acetate, sodium carbonate and potassium carbonate.

In some embodiments, reacting a compound of formula (A-IV) with a compound of formula (A-III) to obtain a compound of formula (I) is carried out in an organic solvent.

In some embodiments, exemplary examples of suitable organic solvents that can be used in the present disclosure to react a compound of formula (A-IV) with a compound of formula (A-III) to obtain a compound of formula (I) include, but are not limited to, acetic acid, formic acid, dimethylformamide and dimethylacetamide.

In some embodiments, a compound of formula (A-IV) is reacted with the compound of formula (A-III) at about 50° C. to about 180° C. to obtain a compound of formula (I).

In another aspect, the present disclosure relates to a compound of formula (II), a stereoisomer thereof, or a pharmaceutically acceptable salt thereof:

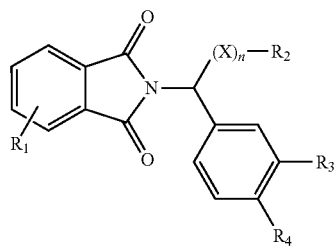

formula (II)

wherein $R_1$ represents one or more identical or different substituents selected from the group consisting of halogen, hydroxy, optionally substituted hydrocarbyl, optionally substituted amino, optionally substituted hydrocarbylcarbonylamino, optionally substituted hydrocarbylcarbonyloxy, optionally substituted hydrocarbyloxycarbonylamino and optionally substituted hydrocarbylcarbonylamino;

$R_2$ is selected from the group consisting of optionally substituted hydrocarbyloxycarbonyl and carboxyl;

$R_3$ is selected from the group consisting of hydrogen, halogen, hydroxy, optionally substituted hydrocarbyloxy, optionally substituted arylhydrocarbyloxy and optionally substituted cyclohydrocarbyloxy;

$R_4$ is selected from the group consisting of hydrogen, halogen, hydroxy, optionally substituted hydrocarbyloxy, optionally substituted arylhydrocarbyloxy and optionally substituted cyclohydrocarbyloxy; and X is —$CR_5R_6$—, wherein if $R_5$ is selected from the group consisting of hydrogen, halogen, optionally substituted hydrocarbyl, optionally substituted cyclohydrocarbyl, optionally substituted aryl and optionally substituted heteroaryl; and $R_6$ is selected from the group consisting of hydrogen, halogen, optionally substituted hydrocarbyl, optionally substituted cyclohydrocarbyl, optionally substituted aryl and optionally substituted heteroaryl, n is 0, 1, 2, 3 or 4; and if $R_5$ and $R_6$ together with a carbon atom to which they are attached form an optionally substituted cyclohydrocarbyl, n is 1.

In some embodiments, $R_1$ represents one or more identical or different substituents selected from the group consisting of halogen, hydroxy, optionally substituted $C_1$-$C_6$hydrocarbyl, optionally substituted amino, optionally substituted $C_1$-$C_6$hydrocarbylcarbonylamino, optionally substituted $C_1$-$C_6$hydrocarbylcarbonyloxy, optionally substituted $C_1$-$C_6$hydrocarbyloxycarbonylamino and optionally substituted $C_1$-$C_6$hydrocarbylcarbonylamino.

In some embodiments, $R_1$ represents one or more identical or different substituents selected from the group consisting of halogen, hydroxy, optionally substituted alkyl, optionally substituted amino, optionally substituted alkylcarbonylamino, optionally substituted alkylcarbonyloxy, optionally substituted alkyloxycarbonylamino and optionally substituted alkylcarbonylamino.

In some embodiments, $R_1$ represents one or more identical or different substituents selected from the group consisting of halogen, hydroxy, optionally substituted $C_1$-$C_6$alkyl, optionally substituted amino, optionally substituted $C_1$-$C_6$alkylcarbonylamino, optionally substituted $C_1$-$C_6$alkylcarbonyloxy, optionally substituted $C_1$-$C_6$alkyloxycarbonylamino and optionally substituted $C_1$-$C_6$alkylcarbonylamino.

In some embodiments, $R_1$ represents one or more identical or different substituents selected from the group consisting of halogen, hydroxy, optionally substituted methyl, optionally substituted amino, optionally substituted acetamido, optionally substituted acetyloxy and optionally substituted tert-butoxycarbonylamino.

In some embodiments, $R_1$ represents one or more identical or different substituents selected from the group consisting of fluoro, chloro, hydroxy, methyl, amino, amino substituted with $C_1$-$C_6$alkyl, acetamido, haloacetamido, acetamido substituted with $C_1$-$C_6$alkyl, acetamido substituted with hydroxy, acetamido substituted with amino substituted with $C_1$-$C_6$alkyl, acetylamino substituted with N—$C_1$-$C_6$alkyl, acetoxy, tert-butoxycarbonylamino and tert-butoxycarbonylamino substituted with $C_1$-$C_6$alkyl.

In some embodiments, $R_1$ represents one or more identical or different substituents selected from the group consisting of fluoro, chloro, hydroxy, methyl, amino, methylamino, dimethylamino, acetamido, 2-chloroacetamido, 2-hydroxyacetamido, N-methylacetamido, 2-(dimethylamino)acetamido, acetoxy, tert-butoxycarbonylamino and N-methyl-tert-butoxycarbonylamino.

In some embodiments, $R_1$ is acetamido

In some embodiments, $R_2$ is selected from the group consisting of optionally substituted $C_1$-$C_6$hydrocarbyloxycarbonyl and carboxyl.

In some embodiments, $R_2$ is selected from the group consisting of optionally substituted alkyloxycarbonyl and carboxyl.

In some embodiments, $R_2$ is selected from the group consisting of optionally substituted $C_1$-$C_6$alkyloxycarbonyl and carboxyl.

In some embodiments, $R_2$ is selected from the group consisting of optionally substituted methoxycarbonyl, optionally substituted ethoxycarbonyl, optionally substituted propoxycarbonyl, optionally substituted butoxycarbonyl, optionally substituted isopropoxycarbonyl and carboxyl.

In some embodiments, $R_2$ is selected from the group consisting of methoxycarbonyl, ethoxycarbonyl, propoxycarbonyl, butoxycarbonyl, isopropoxycarbonyl and carboxyl.

In some embodiments, $R_2$ is selected from the group consisting of methoxycarbonyl, ethoxycarbonyl and propoxycarbonyl.

In some embodiments, $R_3$ is selected from the group consisting of hydrogen, halogen, hydroxy, optionally substituted alkyloxy, optionally substituted arylalkyloxy and optionally substituted cycloalkyloxy.

In some embodiments, $R_3$ is selected from the group consisting of hydrogen, halogen, hydroxy, optionally substituted $C_1$-$C_6$hydrocarbyloxy, optionally substituted $C_6$-$C_{18}$arylhydrocarbyloxy and optionally substituted $C_3$-$C_{10}$cyclohydrocarbyloxyl.

In some embodiments, $R_3$ is selected from the group consisting of hydrogen, halogen, hydroxy, optionally substituted alkyloxy, optionally substituted arylalkyloxy and optionally substituted cycloalkyloxy.

In some embodiments, $R_3$ is selected from the group consisting of hydrogen, halogen, hydroxy, optionally substituted $C_1$-$C_6$alkyloxy, optionally substituted $C_6$-$C_{18}$arylalkyloxy and optionally substituted $C_3$-$C_{10}$cycloalkyloxy.

In some embodiments, $R_3$ is selected from the group consisting of hydrogen, halogen, hydroxy, optionally substituted methoxy, optionally substituted ethoxy, optionally substituted propoxy, optionally substituted isopropoxy, optionally substituted benzyloxy and optionally substituted cyclopentyloxy.

In some embodiments, $R_3$ is selected from the group consisting of hydrogen, chloro, hydroxy, methoxy, difluoromethoxy, trifluoromethoxy, ethoxy, propoxy, isopropoxy, benzyloxy and cyclopentyloxy.

In some embodiments, $R_3$ is selected from the group consisting of methoxy and ethoxy.

In some embodiments, $R_4$ is selected from the group consisting of hydrogen, halogen, hydroxy, optionally substituted alkyloxy, optionally substituted arylalkyloxy and optionally substituted cycloalkyloxy.

In some embodiments, $R_4$ is selected from the group consisting of hydrogen, halogen, hydroxy, optionally substituted $C_1$-$C_6$hydrocarbyloxy, optionally substituted $C_6$-$C_{18}$arylhydrocarbyloxy and optionally substituted $C_3$-$C_{10}$cyclohydrocarbyloxyl.

In some embodiments, $R_4$ is selected from the group consisting of hydrogen, halogen, hydroxy, optionally substituted alkyloxy, optionally substituted arylalkyloxy and optionally substituted cycloalkyloxy.

In some embodiments, $R_4$ is selected from the group consisting of hydrogen, halogen, hydroxy, optionally substituted $C_1$-$C_6$alkyloxy, optionally substituted $C_6$-$C_{18}$arylalkyloxy and optionally substituted $C_3$-$C_{10}$cycloalkyloxy.

In some embodiments, $R_4$ is selected from the group consisting of hydrogen, halogen, hydroxy, optionally substituted methoxy, optionally substituted ethoxy, optionally substituted propoxy, optionally substituted isopropoxy, optionally substituted benzyloxy and optionally substituted cyclopentyloxy.

In some embodiments, $R_4$ is selected from the group consisting of hydrogen, chlorine, hydroxy, methoxy, difluoromethoxy, trifluoromethoxy, ethoxy, propoxy, isopropoxy, benzyloxy and cyclopentyloxy.

In some embodiments, $R_4$ is selected from the group consisting of methoxy and ethoxy.

In some embodiments, $R_5$ is selected from the group consisting of hydrogen, halogen, optionally substituted hydrocarbyl, optionally substituted cyclohydrocarbyl, optionally substituted aryl and optionally substituted heteroaryl.

In some embodiments, $R_5$ is selected from the group consisting of hydrogen, halogen, optionally substituted $C_1$-$C_6$hydrocarbyl, optionally substituted $C_3$-$C_{10}$cyclohydrocarbyl, optionally substituted $C_5$-$C_{12}$aryl and optionally substituted heteroaryl.

In some embodiments, $R_5$ is selected from the group consisting of hydrogen, halogen, optionally substituted alkyl, optionally substituted cycloalkyl, optionally substituted $C_5$-$C_{12}$aryl and optionally substituted heteroaryl.

In some embodiments, $R_5$ is selected from the group consisting of hydrogen, halogen, optionally substituted $C_1$-$C_6$alkyl, optionally substituted $C_3$-$C_{10}$cycloalkyl, optionally substituted $C_5$-$C_{12}$aryl and optionally substituted heteroaryl.

In some embodiments, $R_6$ is selected from the group consisting of hydrogen, halogen, optionally substituted hydrocarbyl, optionally substituted cyclohydrocarbyl, optionally substituted aryl and optionally substituted heteroaryl.

In some embodiments, $R_6$ is selected from the group consisting of hydrogen, halogen, optionally substituted $C_1$-$C_6$hydrocarbyl, optionally substituted $C_3$-$C_{10}$cyclohydrocarbyl, optionally substituted $C_5$-$C_{12}$aryl and optionally substituted heteroaryl.

In some embodiments, $R_6$ is selected from the group consisting of hydrogen, halogen, optionally substituted alkyl, optionally substituted cycloalkyl, optionally substituted $C_5$-$C_{12}$aryl and optionally substituted heteroaryl.

In some embodiments, $R_6$ is selected from the group consisting of hydrogen, halogen, optionally substituted $C_1$-$C_6$alkyl, optionally substituted $C_3$-$C_{10}$cycloalkyl, optionally substituted $C_5$-$C_{12}$aryl and optionally substituted heteroaryl.

In some embodiments, n is 0, 1, 2, 3, or 4.

In some embodiments, $R_5$ and $R_6$ together with a carbon atom to which they are attached form an optionally substituted cyclohydrocarbyl group, and n is 1.

In some embodiments, $R_5$ and $R_6$ together with a carbon atom to which they are attached form an optionally substituted $C_3$-$C_{12}$cyclohydrocarbyl group, and n is 1.

In some embodiments, $R_5$ and $R_6$ together with a carbon atom to which they are attached form an optionally substituted cycloalkyl group, and n is 1.

In some embodiments, $R_5$ and $R_6$ together with a carbon atom to which they are attached form an optionally substituted $C_3$-$C_{12}$cycloalkyl group, and n is 1.

In some embodiments, $R_5$ and $R_6$ together with a carbon atom to which they are attached form an $C_3$-$C_{12}$cycloalkyl group, and n is 1.

In some embodiments, $R_5$ is selected from the group consisting of hydrogen, halogen and $C_1$-$C_4$hydrocarbyl.

In some embodiments, $R_6$ is selected from the group consisting of hydrogen, halogen and $C_1$-$C_4$hydrocarbyl.

In some embodiments, n is 1 or 2.

In some embodiments, $R_5$ is selected from the group consisting of hydrogen, halogen and $C_1$-$C_4$hydrocarbyl; $R_6$ is selected from the group consisting of hydrogen, halogen, and $C_1$-$C_4$hydrocarbyl, and n is 1 or 2.

In some embodiments, $R_5$ is hydrogen.
In some embodiments, $R_6$ is hydrogen.
In some embodiments, n is 1.
In some embodiments, $R_5$ is hydrogen, $R_6$ is hydrogen and n is 1.

In some embodiments, the compound of the present disclosure has immunoglobulin E (IgE) inhibitory activity.

In some embodiments, the compound of the present disclosure has low toxicity.

In some embodiments, the compound of the present disclosure has good safety.

In some embodiments, the compound of the present disclosure has good tolerance.

In yet another aspect, the present disclosure relates to a compound, a stereoisomer thereof, or a pharmaceutically acceptable salt thereof selected from the group consisting of:

methyl 3-(4-acetamido-1,3-dioxoisoindolin-2-yl)-3-(3-ethoxy-4-methoxyphenyl)propionate;
methyl 3-(4-amino-1,3-dioxoisoindolin-2-yl)-3-(3-ethoxy-4-methoxyphenyl)propionate;
methyl 3-(4-acetamido-1,3-dioxoisoindolin-2-yl)-3-(3,4-dimethoxyphenyl)propionate;
methyl 3-(4-acetamido-1,3-dioxoisoindolin-2-yl)-3-(3,4-diethoxyphenyl)propionate;
3-(4-acetamido-1,3-dioxoisoindolin-2-yl)-3-(3-ethoxy-4-methoxyphenyl) propanoic acid;
ethyl 3-(4-acetamido-1,3-dioxoisoindolin-2-yl)-3-(3-ethoxy-4-methoxyphenyl)propionate;
methyl (R)-3-(4-amino-1,3-dioxoisoindolin-2-yl)-3-(3-ethoxy-4-methoxyphenyl)propionate;
methyl (S)-3-(4-amino-1,3-dioxoisoindolin-2-yl)-3-(3-ethoxy-4-methoxyphenyl)propionate;
methyl (R)-3-(4-acetamido-1,3-dioxoisoindolin-2-yl)-3-(3-ethoxy-4-methoxyphenyl)propionate;
methyl (S)-3-(4-acetamido-1,3-dioxoisoindolin-2-yl)-3-(3-ethoxy-4-methoxyphenyl)propionate;
propyl 3-(4-acetamido-1,3-dioxoisoindolin-2-yl)-3-(3-ethoxy-4-methoxyphenyl)propionate;
isopropyl 3-(4-acetamido-1,3-dioxoisoindolin-2-yl)-3-(3-ethoxy-4-methoxyphenyl)propionate;
butyl 3-(4-acetamido-1,3-dioxoisoindolin-2-yl)-3-(3-ethoxy-4-methoxyphenyl)propionate;
methyl 3-(4-(2-chloroacetamino)-1,3-dioxoisoindolin-2-yl)-3-(3-ethoxy-4-methoxyphenyl)propionate;
methyl 3-(4-(2-(dimethylamino)acetamido)-1,3-dioxoisoindolin-2-yl)-3-(3-ethoxy-4-methoxyphenyl)propionate;
3-(4-(dimethylamino)-1,3-dioxoisoindolin-2-yl)-3-(3-ethoxy-4-methoxyphenyl)propionate;
methyl 3-(4-(2-hydroxyacetamido)-1,3-dioxoisoindolin-2-yl)-3-(3-ethoxy-4-methoxyphenyl)propionate;
methyl 3-(4-acetamido-1,3-dioxoisoindolin-2-yl)-3-(3-ethoxy-4-isopropoxyphenyl)propionate;
methyl 3-(4-fluoro-1,3-dioxoisoindolin-2-yl)-3-(3-ethoxy-4-methoxyphenyl)propionate
methyl 3-(4-fluoro-1,3-dioxoisoindolin-2-yl)-3-(3-ethoxy-4-methoxyphenyl)propionate;
methyl 3-(4-acetamido-1,3-dioxoisoindolin-2-yl)-3-(3-ethoxy-4-cyclopentyloxyphenyl)propionate;
methyl 3-(4-methyl-1,3-dioxoisoindolin-2-yl)-3-(3-ethoxy-4-methoxyphenyl)propionate;
methyl 3-(5-fluoro-1,3-dioxoisoindolin-2-yl)-3-(3-ethoxy-4-methoxyphenyl)propionate;
methyl 3-(4,7-dichloro-1,3-dioxoisoindolin-2-yl)-3-(3-ethoxy-4-methoxyphenyl)propionate;
methyl 3-(4-(N-methylacetamido)-1,3-dioxoisoindolin-2-yl)-3-(3-ethoxy-4-methoxyphenyl)propionate;
methyl 3-(5-acetamido-1,3-dioxoisoindolin-2-yl)-3-(3-ethoxy-4-methoxyphenyl)propionate;
methyl 3-(4-acetamido-1,3-dioxoisoindolin-2-yl)-3-(3-(benzyloxy)-4-methoxyphenyl)propionate;
methyl 3-(4-(N-methyl-tert-butoxycarbonylamino)-1,3-dioxoisoindolin-2-yl)-3-(3-ethoxy-4-methoxyphenyl)propionate;
methyl 3-(4-(methylamino)-1,3-dioxoisoindolin-2-yl)-3-(3-ethoxy-4-methoxyphenyl)propionate;
methyl 3-(4-acetamido-1,3-dioxoisoindolin-2-yl)-3-(3-propoxy-4-methoxyphenyl)propionate;
methyl 3-(4-acetamido-1,3-dioxoisoindolin-2-yl)-3-(3-cyclopentyloxy-4-methoxyphenyl)propionate;
methyl 3-(4-acetamido-1,3-dioxoisoindolin-2-yl)-3-(3-ethoxy-4-propoxyphenyl)propionate;
methyl 3-(4-hydroxy-1,3-dioxoisoindolin-2-yl)-3-(3-ethoxy-4-methoxyphenyl)propionate;
methyl 3-(4-acetoxy-1,3-dioxoisoindolin-2-yl)-3-(3-ethoxy-4-methoxyphenyl)propionate;
methyl 3-(4-amino-7-hydroxy-1,3-dioxoisoindolin-2-yl)-3-(3-ethoxy-4-methoxyphenyl)propionate;
methyl 3-(4-amino-5-hydroxy-1,3-dioxoisoindolin-2-yl)-3-(3-ethoxy-4-methoxyphenyl)propionate;
methyl 3-(4-acetamido-1,3-dioxoisoindolin-2-yl)-3-(3-hydroxy-4-methoxyphenyl)propionate;
methyl 3-(4-acetamido-1,3-dioxoisoindolin-2-yl)-3-(3-ethoxy-4-(benzyloxy)phenyl)propionate;
methyl 3-(4-acetamido-1,3-dioxoisoindolin-2-yl)-3-(3-ethoxy-4-hydroxyphenyl)propionate;
methyl 3-(4-acetamido-1,3-dioxoisoindolin-2-yl)-3-(3-methoxy-4-(benzyloxy)phenyl)propionate;
methyl 3-(4-acetamido-1,3-dioxoisoindolin-2-yl)-3-(3-methoxy-4-hydroxyphenyl)propionate;
methyl 3-(4-acetamido-1,3-dioxoisoindolin-2-yl)-3-phenyl-propionate;
methyl 3-(4-Acetamido-1,3-dioxoisoindolin-2-yl)-3-(3-chlorophenyl)propionate;
methyl 3-(4-acetamido-1,3-dioxoisoindolin-2-yl)-3-(4-ethoxypheny)propionate;
methyl 3-(4-Acetamido-1,3-dioxoisoindolin-2-yl)-3-(4-chlorophenyl)propionate;
methyl 3-(4-(tert-butyloxycarbonylamino)-1,3-dioxoisoindolin-2-yl)-3-(3-ethoxy-4-methoxy phenyl)propionate;
methyl 3-(4-acetamido-1,3-dioxoisoindolin-2-yl)-3-(3-isopropoxy-4-methoxyphenyl)propionate;
methyl 3-(4-acetamido-1,3-dioxoisoindolin-2-yl)-3-(4-(difluoromethoxy)-3-ethoxyphenyl)propionate;
methyl 3-(4-acetamido-1,3-dioxoisoindolin-2-yl)-3-(3-ethoxy-4-(trifluoromethoxy)phenyl)propionate;
methyl 3-(4-acetamido-1,3-dioxoisoindolin-2-yl)-3-(3-(difluoromethoxy)-4-methoxyphenyl))propionate;
methyl 3-(4-acetamido-1,3-dioxoisoindolin-2-yl)-3-(4-methoxy-3-(trifluoromethoxy)phenyl)propionate;
methyl (R)-3-(4-acetamido-1,3-dioxoisoindolin-2-yl)-3-(3-ethoxy-4-methoxyphenyl)propionate;
ethyl (S)-3-(4-acetamido-1,3-dioxoisoindolin-2-yl)-3-(3-ethoxy-4-methoxyphenyl)propionate;
methyl (R)-3-(4-acetamido-1,3-dioxoisoindolin-2-yl)-3-(3-isopropoxy-4-methoxyphenyl)propionate; and
methyl (S)-3-(4-acetamido-1,3-dioxoisoindolin-2-yl)-3-(3-isopropoxy-4-methoxyphenyl)propionate;
methyl 3-(4-acetamido-1,3-dioxoisoindolin-2-yl)-3-(benzo[d][1,3]dioxol-5-yl)propionate; and
methyl 3-(4-acetamido-1,3-dioxoisoindolin-2-yl)-3-(2,3-dihydrobenzo[b][1,4]dioxin-6-yl)propionate.

In yet another aspect, the present disclosure relates to a pharmaceutical composition comprising a compound of formula (II), a stereoisomer thereof, or a pharmaceutically acceptable salt thereof and a pharmaceutically acceptable carrier, diluent or excipient:

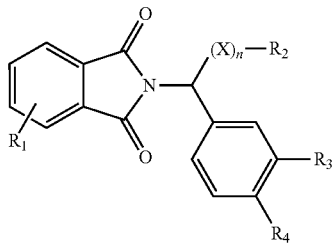

formula (II)

wherein

R₁ represents one or more identical or different substituents selected from the group consisting of halogen, hydroxy, optionally substituted hydrocarbyl, optionally substituted amino, optionally substituted hydrocarbylcarbonylamino, optionally substituted hydrocarbylcarbonyloxy, optionally substituted hydrocarbyloxycarbonylamino and optionally substituted hydrocarbylcarbonylamino;

R₂ is selected from the group consisting of optionally substituted hydrocarbyloxycarbonyl and carboxyl;

R₃ is selected from the group consisting of hydrogen, halogen, hydroxy, optionally substituted hydrocarbyloxy, optionally substituted arylhydrocarbyloxy and optionally substituted cyclohydrocarbyloxy;

R₄ is selected from the group consisting of hydrogen, halogen, hydroxy, optionally substituted hydrocarbyloxy, optionally substituted arylhydrocarbyloxy and optionally substituted cyclohydrocarbyloxy; and X is —CR₅R₆—, wherein if R₅ is selected from the group consisting of hydrogen, halogen, optionally substituted hydrocarbyl, optionally substituted cyclohydrocarbyl, optionally substituted aryl and optionally substituted heteroaryl; and R₆ is selected from the group consisting of hydrogen, halogen, optionally substituted hydrocarbyl, optionally substituted cyclohydrocarbyl, optionally substituted aryl and optionally substituted heteroaryl, n is 0, 1, 2, 3 or 4; and if R₅ and R₆ together with a carbon atom to which they are attached form an optionally substituted cyclohydrocarbyl, n is 1.

In still another aspect, the present disclosure relates to a method for treating or preventing a disease associated with immunoglobulin E (IgE), preferably mediated by immunoglobulin E (IgE) comprising administering a therapeutically effective amount of a compound of formula (II), a stereoisomer thereof, or a pharmaceutically acceptable salt thereof, or a therapeutically effective amount of a pharmaceutical composition comprising a compound of formula (II), a stereoisomer thereof, or a pharmaceutically acceptable salt thereof and a pharmaceutically acceptable carrier, diluent or excipient to a subject in need thereof:

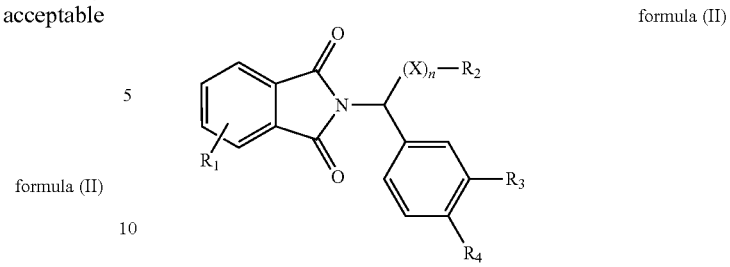

formula (II)

wherein

R₁ represents one or more identical or different substituents selected from the group consisting of halogen, hydroxy, optionally substituted hydrocarbyl, optionally substituted amino, optionally substituted hydrocarbylcarbonylamino, optionally substituted hydrocarbylcarbonyloxy, optionally substituted hydrocarbyloxycarbonylamino and optionally substituted hydrocarbylcarbonylamino;

R₂ is selected from the group consisting of optionally substituted hydrocarbyloxycarbonyl and carboxyl;

R₃ is selected from the group consisting of hydrogen, halogen, hydroxy, optionally substituted hydrocarbyloxy, optionally substituted arylhydrocarbyloxy and optionally substituted cyclohydrocarbyloxy;

R₄ is selected from the group consisting of hydrogen, halogen, hydroxy, optionally substituted hydrocarbyloxy, optionally substituted arylhydrocarbyloxy and optionally substituted cyclohydrocarbyloxy; and X is —CR₅R₆—, wherein if R₅ is selected from the group consisting of hydrogen, halogen, optionally substituted hydrocarbyl, optionally substituted cyclohydrocarbyl, optionally substituted aryl and optionally substituted heteroaryl; and R₆ is selected from the group consisting of hydrogen, halogen, optionally substituted hydrocarbyl, optionally substituted cyclohydrocarbyl, optionally substituted aryl and optionally substituted heteroaryl, n is 0, 1, 2, 3 or 4; and if R₅ and R₆ together with a carbon atom to which they are attached form an optionally substituted cyclohydrocarbyl, n is 1.

In some embodiments, the method for treating or preventing a disease associated with immunoglobulin E (IgE), preferably mediated by immunoglobulin E (IgE) comprises administering 1 mg to 10 g of a compound, a stereoisomer thereof, or a pharmaceutically acceptable salt thereof of the present disclosure to a subject in need thereof.

In some embodiments, the method for treating or preventing a disease associated with immunoglobulin E (IgE), preferably mediated by immunoglobulin E (IgE) comprises administering 10 mg to 3000 mg of a compound, a stereoisomer thereof, or a pharmaceutically acceptable salt thereof of the present disclosure to a subject in need thereof.

In some embodiments, the method for treating or preventing a disease associated with immunoglobulin E (IgE), preferably mediated by immunoglobulin E (IgE) comprises administering 100 mg to 1000 mg of a compound, a stereoisomer thereof, or a pharmaceutically acceptable salt thereof of the present disclosure to a subject in need thereof.

In some embodiments, the method for treating or preventing a disease associated with immunoglobulin E (IgE), preferably mediated by immunoglobulin E (IgE) comprises administering 100 mg, 200 mg, 250 mg, 300 mg, 350 mg, 400 mg, 450 mg, 500 mg, 550 mg, 650 mg, 700 mg, 750 mg, 800 mg, 850 mg, 900 mg or 1000 mg of a compound, a stereoisomer thereof, or a pharmaceutically acceptable salt thereof of the present disclosure to a subject in need thereof.

In yet another aspect, the present disclosure relates to a compound of formula (II), a stereoisomer thereof, or a pharmaceutically acceptable salt thereof for treating or preventing a disease associated with immunoglobulin E (IgE), preferably mediated by immunoglobulin E (IgE):

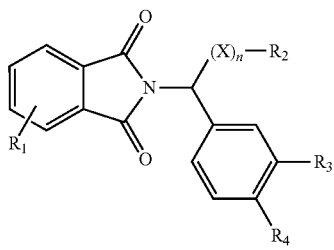

formula (II)

wherein $R_1$ represents one or more identical or different substituents selected from the group consisting of halogen, hydroxy, optionally substituted hydrocarbyl, optionally substituted amino, optionally substituted hydrocarbylcarbonylamino, optionally substituted hydrocarbylcarbonyloxy, optionally substituted hydrocarbyloxycarbonylamino and optionally substituted hydrocarbylcarbonylamino;

$R_2$ is selected from the group consisting of optionally substituted hydrocarbyloxycarbonyl and carboxyl;

$R_3$ is selected from the group consisting of hydrogen, halogen, hydroxy, optionally substituted hydrocarbyloxy, optionally substituted arylhydrocarbyloxy and optionally substituted cyclohydrocarbyloxy;

$R_4$ is selected from the group consisting of hydrogen, halogen, hydroxy, optionally substituted hydrocarbyloxy, optionally substituted arylhydrocarbyloxy and optionally substituted cyclohydrocarbyloxy; and X is —$CR_5R_6$—, wherein if $R_5$ is selected from the group consisting of hydrogen, halogen, optionally substituted hydrocarbyl, optionally substituted cyclohydrocarbyl, optionally substituted aryl and optionally substituted heteroaryl; and $R_6$ is selected from the group consisting of hydrogen, halogen, optionally substituted hydrocarbyl, optionally substituted cyclohydrocarbyl, optionally substituted aryl and optionally substituted heteroaryl, n is 0, 1, 2, 3 or 4; and if $R_5$ and $R_6$ together with a carbon atom to which they are attached form an optionally substituted cyclohydrocarbyl, n is 1.

In yet another aspect, the present disclosure relates to a pharmaceutical composition for treating or preventing a disease associated with immunoglobulin E (IgE), preferably mediated by immunoglobulin E (IgE) comprising a therapeutically effective amount of a compound of formula (II), a stereoisomer thereof, or a pharmaceutically acceptable salt thereof and a pharmaceutically acceptable carrier, diluent or excipient:

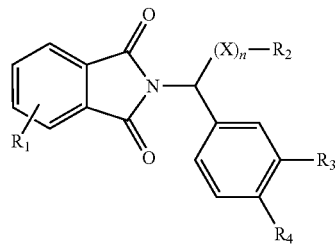

formula (II)

wherein $R_1$ represents one or more identical or different substituents selected from the group consisting of halogen, hydroxy, optionally substituted hydrocarbyl, optionally substituted amino, optionally substituted hydrocarbylcarbonylamino, optionally substituted hydrocarbylcarbonyloxy, optionally substituted hydrocarbyloxycarbonylamino and optionally substituted hydrocarbylcarbonylamino;

$R_2$ is selected from the group consisting of optionally substituted hydrocarbyloxycarbonyl and carboxyl;

$R_3$ is selected from the group consisting of hydrogen, halogen, hydroxy, optionally substituted hydrocarbyloxy, optionally substituted arylhydrocarbyloxy and optionally substituted cyclohydrocarbyloxy;

$R_4$ is selected from the group consisting of hydrogen, halogen, hydroxy, optionally substituted hydrocarbyloxy, optionally substituted arylhydrocarbyloxy and optionally substituted cyclohydrocarbyloxy; and X is —$CR_5R_6$—, wherein if $R_5$ is selected from the group consisting of hydrogen, halogen, optionally substituted hydrocarbyl, optionally substituted cyclohydrocarbyl, optionally substituted aryl and optionally substituted heteroaryl; and $R_6$ is selected from the group consisting of hydrogen, halogen, optionally substituted hydrocarbyl, optionally substituted cyclohydrocarbyl, optionally substituted aryl and optionally substituted heteroaryl, n is 0, 1, 2, 3 or 4; and if $R_5$ and $R_6$ together with a carbon atom to which they are attached form an optionally substituted cyclohydrocarbyl, n is 1.

In another aspect, the present disclosure relates to a compound of formula (II), a stereoisomer thereof, or a pharmaceutically acceptable salt thereof for treating or preventing dermatosis, psoriasis, eczema, atopic dermatitis, urticaria, asthma, asthma-chronic obstructive pulmonary disease (COPD) overlap syndrome (ACOS), allergic rhinitis, seasonal allergic rhinitis, drug-induced interstitial lung disease, bronchopulmonary aspergillosis, leprosy, pemphigoid and parasitic infections:

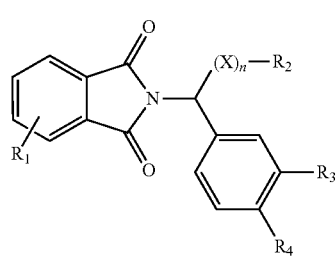

formula (II)

wherein $R_1$ represents one or more identical or different substituents selected from the group consisting of halogen, hydroxy, optionally substituted hydrocarbyl, optionally substituted amino, optionally substituted hydrocarbylcarbonylamino, optionally substituted hydrocarbylcarbonyloxy, optionally substituted hydrocarbyloxycarbonylamino and optionally substituted hydrocarbylcarbonylamino;

$R_2$ is selected from the group consisting of optionally substituted hydrocarbyloxycarbonyl and carboxyl;

$R_3$ is selected from the group consisting of hydrogen, halogen, hydroxy, optionally substituted hydrocarbyloxy, optionally substituted arylhydrocarbyloxy and optionally substituted cyclohydrocarbyloxy;

$R_4$ is selected from the group consisting of hydrogen, halogen, hydroxy, optionally substituted hydrocarbyloxy, optionally substituted arylhydrocarbyloxy and optionally substituted cyclohydrocarbyloxy; and X is —$CR_5R_6$—, wherein if $R_5$ is selected from the group consisting of hydrogen, halogen, optionally substituted hydrocarbyl, optionally substituted cyclohydrocarbyl, optionally substituted aryl and optionally substituted heteroaryl; and $R_6$ is selected from the group consisting of hydrogen, halogen, optionally substituted hydrocarbyl, optionally substituted cyclohydrocarbyl, optionally substituted aryl and optionally substituted heteroaryl, n is 0, 1, 2, 3 or 4; and if $R_5$ and $R_6$ together with a carbon atom to which they are attached form an optionally substituted cyclohydrocarbyl, n is 1.

In yet another aspect, the present disclosure relates to compounds of formula (II), a stereoisomer of formula (II) or a pharmaceutically acceptable salt thereof for treating or preventing dermatosis, psoriasis, eczema, atopic dermatitis, urticaria, asthma, asthma-chronic obstructive pulmonary disease (COPD) overlap syndrome (ACOS), allergic rhinitis, seasonal allergic rhinitis, drug-induced interstitial lung disease, bronchopulmonary aspergillosis, leprosy, pemphigoid and parasitic infection associated with immunoglobulin E (IgE), preferably mediated by immunoglobulin E (IgE):

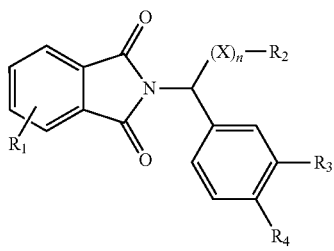

formula (II)

wherein $R_1$ represents one or more identical or different substituents selected from the group consisting of halogen, hydroxy, optionally substituted hydrocarbyl, optionally substituted amino, optionally substituted hydrocarbylcarbonylamino, optionally substituted hydrocarbylcarbonyloxy, optionally substituted hydrocarbyloxycarbonylamino and optionally substituted hydrocarbylcarbonylamino;

$R_2$ is selected from the group consisting of optionally substituted hydrocarbyloxycarbonyl and carboxyl;

$R_3$ is selected from the group consisting of hydrogen, halogen, hydroxy, optionally substituted hydrocarbyloxy, optionally substituted arylhydrocarbyloxy and optionally substituted cyclohydrocarbyloxy;

$R_4$ is selected from the group consisting of hydrogen, halogen, hydroxy, optionally substituted hydrocarbyloxy, optionally substituted arylhydrocarbyloxy and optionally substituted cyclohydrocarbyloxy; and X is —$CR_5R_6$—, wherein if $R_5$ is selected from the group consisting of hydrogen, halogen, optionally substituted hydrocarbyl, optionally substituted cyclohydrocarbyl, optionally substituted aryl and optionally substituted heteroaryl; and $R_6$ is selected from the group consisting of hydrogen, halogen, optionally substituted hydrocarbyl, optionally substituted cyclohydrocarbyl, optionally substituted aryl and optionally substituted heteroaryl, n is 0, 1, 2, 3 or 4; and if $R_5$ and $R_6$ together with a carbon atom to which they are attached form an optionally substituted cyclohydrocarbyl, n is 1.

Pharmaceutical Composition

In some embodiments, the pharmaceutical composition comprises a compound, a stereoisomer thereof, or a pharmaceutically acceptable salt thereof of the present disclosure and a pharmaceutically acceptable carrier, diluent or excipient.

In some embodiments, the route of administration of a compound, a stereoisomer thereof, or a pharmaceutically acceptable salt thereof of the present disclosure for treating or preventing a disease associated with immunoglobulin E (IgE), preferably mediated by immunoglobulin E (IgE) to a mammal can be non-parenteral route or parenteral route.

In some embodiments, the route of administration of a compound, a stereoisomer thereof, or a pharmaceutically acceptable salt thereof of the present disclosure for treating or preventing a disease associated with immunoglobulin E (IgE), preferably mediated by immunoglobulin E (IgE) to a mammal can be oral route.

In some embodiments, the route of administration of a compound, a stereoisomer thereof, or a pharmaceutically acceptable salt thereof of the present disclosure for treating or preventing a disease associated with immunoglobulin E (IgE), preferably mediated by immunoglobulin E (IgE) to a mammal can be intrarectal route.

The compound described herein may be obtained in any suitable form such as tablet, capsule, powder, oral solution, suspension, rectal gel, rectal foam, rectal enema or rectal suppository, and the like. Exemplary examples of the tablets include, but are not limited to, plain tablets, sugar-coated tablets and film-coated tablets.

Examples of a pharmaceutically acceptable carrier that can be used in the pharmaceutical composition of the present disclosure include, but are not limited to, any adjuvant, carrier, excipient, glidant, sweetening agent, diluent, preservative, dye/colorant, flavor enhancer, surfactant, wetting agent, dispersing agent, suspending agent, stabilizer, isosmotic agent, solvent, or emulsifier, etc, which has been approved by the United States Food and Drug Administration as being acceptable for use in humans or animals and have no side effects on preparing a pharmaceutical composition. Acceptable carriers or diluents for therapeutic use are well-known in the pharmaceutical field and are available, taking Remington's Pharmaceuticals, 18th Ed., Mack Publishing Co., Easton, Pa. (1990) as an example. The present disclosure takes its entire content as a reference.

The pharmaceutical composition in the present disclosure may be administered by any means that achieve their intended purpose. For example, administration may be by oral, parenteral, topical, enteral, intravenous, intramuscular, inhalation, nasal, intra-articular, intraspine, transtracheal, ocular, subcutaneous, intraperitoneal, transdermal, or buccal routes. The route of administration can be parenteral route, oral route, or intrarectal route. The dose administered will be dependent upon the age, health and weight of the recipient, kind of concurrent treatment if any, frequency of treatment, and the nature of the effect desired.

Suitable dosage forms include, but are not limited to capsule, tablet, pellet, dragee, semi-solid preparation, powder, granule, suppository, ointment, cream, lotion, inhalant, injection, cataplasma, gel, tape, eye drop, solution, syrup, aerosol, suspension and emulsion, which can be produced according to methods known in the art.

Particularly suitable for oral use are ordinary tablets (plain tablets), sugar-coated tablets, film-coated tablets, pills, capsule, powders, granules, syrups, juices and drops; suitable for rectal use are suppositories; suitable for parenteral use are solutions, or oil-based or aqueous solutions, furthermore suspensions, emulsions and implants; suitable for topical use are ointments, creams and powders. The product of the present disclosure may also be lyophilized, and the resultant lyophilisates used, for example, for the preparation of injection preparations. The preparations indicated may be sterilized and/or comprise assistants such as wetting agents, preservatives, stabilizers and/or wetting agents, emulsifiers, salts for modifying the osmotic pressure, buffer substances, dyes, flavoring agents and/or a plurality of further active ingredients, for example one or more vitamins.

In some embodiments, the pharmaceutical composition of the present disclosure is formulated as tablet, solution, granule, patch, ointment, capsule, aerosol or suppository via parenteral, transdermal, mucosal, nasal, buccal, sublingual or oral route.

Preservatives, stabilizers, dyes, sweeteners, fragrances, spices, and the like may be provided in the pharmaceutical composition. For example, sodium benzoate, ascorbic acid, and ester of p-hydroxybenzoic acid may be added as preservatives. Furthermore, antioxidants and suspending agents may be used.

In various embodiments, alcohols, esters, sulfated aliphatic alcohols and the like may be used as surfactants; sucrose, glucose, lactose, starch, crystalline cellulose, mannitol, light anhydrous silicate, magnesium aluminate, magnesium aluminum silicate, synthetic aluminum silicate, calcium carbonate, calcium bicarbonate, calcium hydrogen phosphate, calcium hydroxymethyl cellulose and the like may be used as excipients; magnesium stearate, talc, hardened oil and the like may be used as smoothing agents; coconut oil, olive oil, sesame oil, peanut oil and soybean may be used as suspending agents or lubricants; acetate cellulose as a derivative of sugar like cellulose or sugar, or methyl acetate-methacrylate copolymer as a derivative of polyethylen may be used as suspending agents; and plasticizers like phthalate ester may be used as suspending agents.

Suitable administration routes may, for example, include oral, rectal, transmucosal, topical or intestinal administration; parenteral delivery, including intramuscular, subcutaneous, intravenous, intramedullary injections, as well as intrathecal, direct intraventricular, intraperitoneal, intranasal or intraocular injections. The compound can be administered in sustained or controlled release dosage forms including depot injections, osmotic pumps, pills and transdermal (comprising electromigration) patches, and the like for prolonged and/or timed, pulsed administration at a predetermined rate.

Pharmaceutical compositions of the present disclosure may be manufactured in manner that is itself known, for example, by means of conventional mixing, dissolving, granulating, dragee-making, levigating, emulsifying, encapsulating, entrapping, or tableting processes.

Therefore, according to the present disclosure, the pharmaceutical composition used can be formulated in a conventional manner using one or more physiologically acceptable carriers containing excipients and adjuvants. The excipients and adjuvants facilitate the processing of the active compound into pharmaceutically usable preparations. The appropriate preparation depends on the chosen route of administration. Any well-known techniques, carriers and excipients can be used as is suitable and understood in the art.

The injection can be prepared in the following conventional forms: as a solution, a suspension, or a solid dosage form suitable for solution or suspension before injection, or as an emulsion. Suitable excipient comprises water, saline, glucose, mannitol, lactose, lecithin, albumin, sodium glutamate, cysteine hydrochloride and the like. In addition, if necessary, the injectable pharmaceutical composition can contain a small amount of non-toxic auxiliary substances, such as wetting agents, pH buffering agents, and the like. Physiologically suitable buffer comprises but is not limited to a Hank's solution, a Ringer's solution, or a physiological saline buffer. If necessary, absorption enhancing preparations (e.g., liposomes) can be used.

For oral administration, a compound can be easily formulated by combining the active compound with a pharmaceutically acceptable carrier known in the art. For oral ingestion by patients to be treated, such a carrier enables a compound of the present disclosure to be formulated as a tablet, a pill, a lozenge, a capsule, a liquid, a gel, a syrup, an ointment, a suspension, a solution, a powder, and the like. The pharmaceutical preparation for oral administration can be obtained by mixing an active compound with a solid excipient, grinding the resulting mixture arbitrarily, and processing the mixture of granules. If necessary, after adding a suitable adjuvant and then processing it to obtain tablets or lozenge core. Suitable excipients are in particular fillers such as sugars, comprising a lactose, a sucrose, a mannitol and a sorbitol; cellulose preparation comprises a corn starch, a wheat starch, a rice starch, a potato starch, a gelatin, a tragacanth, an alpha cellulose, a hydroxypropylmethyl cellulose, a sodium carboxymethyl cellulose and/or polyvinylpyrrolidone (PVP). If needed, a disintegrating agent can be added, such as a cross-linked polyvinylpyrrolidone, an agar or an alginic acid, or an alginate such as a sodium alginate. The tablet core is coated appropriately. For this purpose, concentrated sugar solution can be used, which can optionally contain a gum arabic, a talc, a polyvinylpyrrolidone, a carbopol gel, a polyethylene glycol and/or a titanium dioxide, a shellac paint solution and a suitable organic solvent or a solvent mixture. To identify or characterize different combinations of an active compound doses, dyes or pigments can be added to a tablet or a dragee coating. For this purpose, concentrated sugar solution can be used, which can optionally contain a gum arabic, a talc, a polyvinylpyrrolidone, a carbopol gel, a polyethylene glycol, and/or a titanium dioxide, a shellac lacquer solution, and a suitable organic solvent or a solvent mixture.

Pharmaceutical preparation that can be used for oral administration comprise push-fit capsules made of gelatin, and soft, sealed capsules made of gelatin such as glycerin or sorbitol and plasticizers. A push-fit capsule can contain an active ingredient mixed with a filler like lactose, a binder like starch, and/or a lubricant like talc or a magnesium stearate, and an optional stabilizer. In a soft capsule, an active ingredient can be dissolved or suspended in a suitable liquid, such as a fatty oil, a liquid paraffin, or a liquid polyethylene glycol. In addition, a stabilizer can be added. All preparations for oral administration should reach a dosage suitable for such administration.

In some embodiments, the pharmaceutical composition of the present disclosure may contain 0.1%-95% of a compound, a stereoisomer thereof, or a pharmaceutically acceptable salt thereof of the present disclosure.

In some embodiments, the pharmaceutical composition of the present disclosure may contain 1%-70% of a compound, a stereoisomer thereof, or a pharmaceutically acceptable salt thereof of the present disclosure.

In any case, the composition or the formulation to be administered comprises an amount of a compound, a stereoisomer thereof, or a pharmaceutically acceptable salt thereof of the present disclosure to effectively treat the disease/condition of a subject to be treated.

Methods of Administration

At least one of the compound, the stereoisomer thereof or the pharmaceutically acceptable salt thereof of the present disclosure or the pharmaceutical compositions comprising at least one of the compound, the stereoisomer thereof or the pharmaceutically acceptable salt thereof of the present disclosure may be administered to the patient by any suitable means and/or by any means that topically delivers the compound, the stereoisomer thereof or the pharmaceutically acceptable salt thereof of the present disclosure. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the compound of the present disclosure into contact with living tissue.

The most suitable route depends on the nature and severity of the condition to be treated. A person having ordinary skill in the art also knows determination of methods of administration (buccal, intravenous, inhalation subcutaneous, rectal and the like), dosage form, suitable pharmaceutical excipients and other events regarding delivering the compound, the stereoisomer thereof or the pharmaceutically acceptable salt thereof to a subject in need thereof.

Pharmaceutical compositions suitable for administration include compositions where the active ingredients are contained in an amount effective to achieve its intended purpose. The therapeutically effective amount of the pharmaceutical composition disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of the compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired affects and the therapeutic indication. Typically, dosages may be between about 10 µg/kg and 1000 mg/kg body weight, in some embodiments, between about 100 µg/kg and 300 mg/kg body weight. Alternatively, dosages may be based and calculated upon the surface area of the patient, as understood by those of skill in the art.

The exact formulation, route of administration and dosage for the pharmaceutical compositions of the present disclosure can be chosen by the individual physician in view of the patient's condition. Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, the present disclosure will use those same dosages, or dosages that are between about 0.1% and 500%, in some embodiments, between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, in some embodiments, between 1 mg and 2000 mg, e.g. 5 to 1500 mg. In other embodiments, an intravenous, subcutaneous, or intramuscular dose of each active ingredient of between 0.01 mg and 1000 mg, in some embodiments, between 0.1 mg and 1000 mg, e.g. 1 to 800 mg is used. In cases of administration of a pharmaceutically acceptable salt, dosages may be calculated as the free base. In some embodiments, the composition is administered 1 to 4 times per day. Alternatively, the compositions of the disclosure may be administered by continuous intravenous infusion, in some embodiments, at a dose of each active ingredient up to 2000 mg per day. As will be understood by those of skill in the art, in certain situations it may be necessary to administer the compounds disclosed herein in amounts that exceed, or even far exceed, the above-stated dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, in some embodiments, between 30-90% and in some embodiments, between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and in some embodiments, human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the State Food and Drug Administration or the U.S. Food and Drug Administration for prescription drugs, or the approved product insert. Compositions comprising a compound of the disclosure, a stereoisomer thereof or a pharmaceutically acceptable salt thereof formulated in a compatible pharmaceutical carrier may also be prepared, placed in an appropriate container, and labeled for treatment of an indicated condition.

In yet another aspect, the present disclosure relates to a process for preparing a compound of formula (II), a stereoisomer thereof or a pharmaceutically acceptable salt thereof, comprising:

(1) reacting a compound of formula (B-I) with malonic acid and ammonium acetate to obtain a compound of formula (B-II),

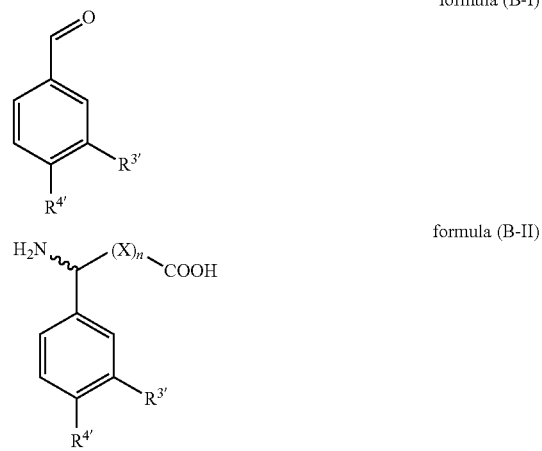

wherein groups represented by $R_3''$ and $R_4''$ in formula (B-I) and formula (B-II) have the same definitions as $R_3$ and $R_4$ in formula (II), (2) esterifying the compound of formula (B-II) with alcohol to obtain a compound of formula (B-III),

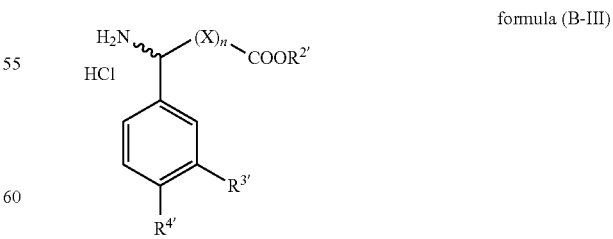

wherein groups represented by $R^{3''}$ and $R^{4''}$ in formula (B-II) and formula (B-III) have the same definitions as $R_3$ and $R_4$ in formula (II), and $R^{2'}$ is selected from the group consisting of hydrogen and hydrocarbyl; and (3) reacting a compound of formula (B-IV) with the compound of formula (B-III) to obtain the compound of formula (II)

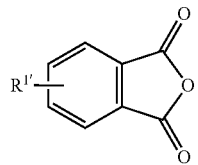

formula (B-IV)

wherein groups represented by R$^{1''}$, R$^{3''}$ and R$^{4''}$ in formula (B-III) and formula (B-IV) have the same definitions as R$_1$, R$_3$ and R$_4$ in formula (II), and R$^{2'}$ is selected from the group consisting of hydrogen and hydrocarbyl;

wherein X is —CR$_5$R$_6$—, wherein R$_5$ is hydrogen, R$_6$ is hydrogen and n is 1.

In some embodiments, reacting a compound of formula (B-I) with malonic acid and ammonium acetate to obtain a compound of formula (B-II) is carried out in an organic solvent.

In some embodiments, exemplary examples of suitable organic solvents that can be used in the present disclosure to react a compound of formula (B-I) with malonic acid and ammonium acetate to obtain a compound of formula (B-II) include, but are not limited to, methanol, ethanol, isopropanol and water.

In some embodiments, a compound of formula (B-I) is reacted with malonic acid and ammonium acetate at about 50° C. to about 130° C. to obtain a compound of formula (B-II).

In some embodiments, exemplary examples of suitable esterifying agents that can be used to prepare a compound of formula (B-III) with a compound of formula (B-II) include, but are not limited to, thionyl chloride, oxalyl chloride, HCl gas and acetyl chloride.

In some embodiments, reacting a compound of formula (B-II) with an alcohol compound to obtain a compound of formula (B-III) is carried out in an organic solvent.

In some embodiments, exemplary examples of suitable organic solvents that can be used in the present disclosure to react a compound of formula (B-II) with an alcohol compound to obtain a compound of formula (B-III) include, but are not limited to, alcohols, tetrahydrofuran, dichloromethane, ethyl acetate and methyl tert-butyl ether.

In some embodiments, exemplary examples of suitable alcohols that can be used in the present disclosure to react a compound of formula (B-II) with an alcohol compound to obtain a compound of formula (B-III) include, but are not limited to, methanol, ethanol and isopropanol.

In some embodiments, a compound of formula (B-II) is reacted with an alcohol compound at about −20° C. to about 30° C. to obtain a compound of formula (B-III).

In some embodiments, a catalyst is added to react a compound of formula (B-IV) with a compound of formula (B-III) to obtain a compound of formula (II).

In some embodiments, exemplary examples of suitable catalysts that can be used in the present disclosure to react a compound of formula (B-IV) with a compound of formula (B-III) to obtain a compound of formula (II) include, but are not limited to, sodium acetate, potassium acetate, sodium carbonate and potassium carbonate.

In some embodiments, reacting a compound of formula (B-IV) with a compound of formula (B-III) to obtain a compound of formula (II) is carried out in an organic solvent.

In some embodiments, exemplary examples of suitable organic solvents that can be used in the present disclosure to react a compound of formula (B-IV) with a compound of formula (B-III) to obtain a compound of formula (II) include, but are not limited to, acetic acid, formic acid, dimethylformamide and dimethylacetamide.

In some embodiments, a compound of formula (B-IV) is reacted with a compound of formula (B-III) at about 50° C. to about 180° C. to obtain a compound of formula (II).

Hereinafter, the present disclosure is explained in detail through the following examples in order to better understand various aspects and advantages of the present disclosure. However, it should be understood that the following examples are non-limiting and are only used to illustrate some embodiments of the present application.

EXAMPLES

Abbreviations:
DMF: N, N-Dimethylformamide
DCM: Dichloromethane
THF: Tetrahydrofuran
PE: Petroleum Ether
EA: Ethyl Acetate
AcOH: Acetic Acid
DMAP: 4-Dimethylaminopyridine
CDCl$_3$: Deuterated Chloroform
HPLC: High Performance Liquid Chromatography
TLC: Thin Layer Chromatography Example 1 methyl 3-(4-acetamido-1,3-dioxoisoindolin-2-yl)-3-(3-ethoxy-4-methoxyphenyl)propionate To a reaction flask were added 3-nitrophthalic acid (10.0 g), palladium on carbon (1.0 g, Pd content: 10%) and tetrahydrofuran (200 mL). The air was replaced with a hydrogen balloon for three times. The mixture was stirred at room temperature for 16 hours. The reaction was monitored to complete with high performance liquid chromatography. The reaction solution was filtered. The filtrate was concentrated under reduced pressure with a water pump to obtain a crude product. The crude product was pulped with dichloromethane and purified to obtain a yellow solid, i.e. 3-aminophthalic acid (4.0 g) (HPLC purity: 81.88%). Yield: 47%. MS (m/e): 182.24 (M+H$^+$).

To a reaction flask were added 3-aminophthalic acid (1.0 g) and acetic anhydride (2.5 mL). The mixture was heated to 105° C. to react for 2 hours. TLC showed that the reaction was completed. The reaction solution was cooled to the room temperature and filtered under reduced pressure. The filter cake was collected. The filter cake was pulped with ether and purified. The resultant mixture was filtered under reduced pressure. The filter cake was collected to give a yellow solid, i.e. N-(1,3-dioxo-1,3-dihydroisobenzofuran-4-yl)acetamide (0.67 g) (HPLC purity: 98.94%). Yield: 59%.

To a reaction flask were added 3-ethoxy-4-methoxybenzaldehyde (200 g), ammonium acetate (171 g) and malonic acid (150 g). Ethanol (1235 mL) and water (65 mL) were added into the mixture. The resultant mixture was heated to reflux (with an internal temperature of 80° C.) under stirring. The resultant mixture was stirred at reflux temperature for 16 hours to precipitate a large amount of solids. The reaction was monitored to complete with HPLC. The reaction solution was filtered under reduced pressure to collect filter cake. The filter cake was pulped with ethyl acetate and purified. The slurry was filtered to collect filter cake. The filter cake was dried in a vacuum oven (40° C.) to give a white solid, i.e. 3-amino-3-(3-ethoxy-4-methoxyphenyl)propionic acid (168 g) (HPLC purity: 80.48%). Yield: 65.5%. MS (m/e): 240.12 (M+H$^+$).

To a reaction flask were added 3-amino-3-(3-ethoxy-4-methoxyphenyl)propionic acid (83 g) and methanol (581 mL). The mixture was cooled to 0° C. Thionyl chloride (53.65 g) was slowly dropwise added with stirring. After the dropwise addition was completed, the mixture was slowly warmed to the room temperature and stirred overnight. The reaction was monitored to complete with HPLC. To the reaction solution was added methyl tert-butyl ether (2.9 L). The mixture was stirred at the room temperature overnight. A large amount of the precipitated solids was filtered under reduced pressure. The filter cake was collected and dried in a vacuum oven (45° C.) to give a white solid, i.e. methyl 3-amino-3-(3-ethoxy-4-methoxyphenyl)propionate hydrochloride (86 g) (HPLC purity: 99.36%). Yield: 87%. MS (m/e): 254.13 (M+H$^+$).

To a reaction flask were added methyl 3-amino-3-(3-ethoxy-4-methoxyphenyl)propionate hydrochloride (50.73 g), N-(1,3-dioxo-1,3-dihydroisobenzofuran-4-yl)acetamide (30 g), sodium acetate (24 g) and AcOH (300 mL). The reaction flask was placed in an oil bath and heated to 140° C. The mixture was stirred to react for 6 hours. The reaction was monitored to complete with HPLC. The reaction solution was successively concentrated under reduced pressure with a water pump to obtain a crude product. DCM and water were added to the crude product. The crud product was dissolved and extracted. The organic phase was collected and washed twice with saturated salt water. The organic phase was dried over anhydrous sodium sulfate and concentrated under reduced pressure with a water pump. The resultant crude product was purified with silica gel column chromatography (the eluent was petroleum ether:ethyl acetate=15:1 to 1:1) to give the title compound (41.3 g) (HPLC purity: 99.24%). Yield: 64.1%.

$^1$HNMR (CDCl$_3$, 400 MHz) δ 9.519 (bs, 1H), 8.750-8.729 (d, 1H), 7.651-7.612 (dd, 1H), 7.476-7.456 (dd, 1H), 7.081-7.054 (m, 2H), 6.832-6.810 (d, 1H), 5.734-5.695 (q, 1H), 4.130-4.078 (q, 2H), 3.840 (s, 3H), 3.812-3.745 (q, 1H), 3.648 (s, 3H), 3.217-3.162 (q, 1H), 2.258 (s, 3H), 1.475-1.440 (t, 3H). MS (m/e): 441.16 (M+H$^+$).

Example 2 methyl 3-(4-amino-1,3-dioxoisoindolin-2-yl)-3-(3-ethoxy-4-methoxyphenyl)propionate Methyl 3-(3-ethoxy-4-methoxyphenyl)-3-(4-nitro-1,3-dioxoisoindolin-2-yl)propionate (16.2 g, HPLC purity: 95.15%) was prepared with methyl 3-amino-3-(3-ethoxy-4-methoxyphenyl)propionate hydrochloride and 3-nitrophthalic anhydride in accordance with the preparation process in Example 1. Yield: 75%. MS (m/e): 429.12 (M+H$^+$).

To a reaction flask were added methyl 3-(3-ethoxy-4-methoxyphenyl)-3-(4-nitro-1,3-dioxoisoindolin-2-yl)propionate (6.0 g), palladium on carbon (3.0 g, palladium content: 10%) and tetrahydrofuran (200 mL). The air was replaced with a hydrogen balloon for three times. The mixture was stirred at room temperature for 16 hours. The TLC showed that the reaction was completed. The reaction solution was filtered. The filtrate was concentrated under reduced pressure with a water pump to give a crude product. The crude product was purified with silica gel column chromatography (eluent: PE:EA=3:1) to give the title compound as a yellow solid (3.87 g, HPLC purity: 96.49%). Yield: 74.1%. MS (m/e): 399.15 (M+H$^+$).

Example 3 methyl 3-(4-acetamido-1,3-dioxoisoindolin-2-yl)-3-(3,4-dimethoxyphenyl)propionate To a reaction flask were added 3-hydroxy-4-methoxybenzaldehyde (5.0 g) and potassium carbonate (4.56 g). The mixture was dissolved with DMF. Iodomethane (3.1 mL) was added in the mixture. The reaction flask was transferred to an oil bath and the mixture was stirred at 65° C. for 15 hours. HPLC showed that the reaction was completed. The reaction solution was diluted in ethyl acetate. The resultant mixture was washed with saturated salt water and extracted. The organic phase was collected, dried over anhydrous magnesium sulfate and concentrated to dryness with a water pump at 40° C. to give a crude product. The crude product was purified with silica gel column chromatography (eluent: PE:EA=8:1) to give a colorless oily product, i.e. (3,4-dimethoxybenzaldehyde) (4.95 g, HPLC purity: 99.94%). Yield: 90%.

3-amino-3-(3,4-dimethoxyphenyl)propionic acid (4.28 g, HPLC purity: 98.54%) was prepared with 3,4-dimethoxybenzaldehyde (4.9 g) in accordance with the preparation process in Example 1. Yield: 79%. MS (m/e): 226.10 (M+H$^+$).

Methyl 3-amino-3-(3,4-dimethyl oxyphenyl)propionate hydrochloride (4.4 g, HPLC purity: 99.89%) was prepared with 3-amino-3-(3,4-dimethoxyphenyl)propionic acid (4.28 g) in accordance with the preparation process in Example 1. Yield: 96.7%. MS (m/e): 240.12 (M+H$^+$).

The title compound (0.68 g, HPLC purity: 96.49%) was prepared with methyl 3-amino-3-(3,4-dimethoxyphenyl)propionate hydrochloride (1.16 g) and N-(1,3-dioxo-1,3-dihydroisobenzofuran-4-yl)acetamide (1.0 g) in accordance with the preparation process in Example 1. Yield: 32.6%. MS (m/e): 427.14 (M+H$^+$).

Example 4 methyl 3-(4-acetamido-1,3-dioxoisoindolin-2-yl)-3-(3,4-diethoxyphenyl)propionate An oily compound product of (3,4-diethoxybenzaldehyde) (3.48 g, HPLC purity: 98.99%) was prepared with 3-ethoxy-4-hydroxybenzaldehyde (3.0 g) and ethyl iodide in accordance with the preparation process in Example 3. Yield: 99.3%.

3-amino-3-(3,4-diethoxyphenyl)propionic acid (4.0 g, HPLC purity: 97.68%) was prepared with 3,4-diethoxybenzaldehyde (3.48 g) in accordance with the preparation process in Example 3. Yield: 88.1% MS (m/e): 254.13 (M+H$^+$).

Methyl 3-amino-3-(3,4-diethoxyphenyl)propionate hydrochloride (2.9 g, HPLC purity: 99.26%) was prepared with 3-amino-3-(3,4-diethoxyphenyl)propionic acid (4.0 g) in accordance with the preparation process in Example 1. Yield: 60.9%. MS (m/e): 268.15 (M+H$^+$).

The title compound (0.38 g, HPLC purity: 98.79%) was prepared with methyl 3-amino-3-(3,4-diethoxyphenyl)propionate hydrochloride (1.48 g) and N-(1,3-dioxo-1,3-dihydroisobenzofuran-4-yl)acetamide (1.0 g) in accordance with the preparation process in Example 1. Yield: 17.2%. MS (m/e): 455.17 (M+H⁺).

Example 5

3-(4-acetamido-1,3-dioxoisoindolin-2-yl)-3-(3-ethoxy-4-methoxyphenyl)propionic acid The title compound (2.73 g), HPLC purity: 98.81%) was prepared with 3-amino-3-(3-ethoxy-4-methoxyphenyl)propionic acid (2.1 g) and N-(1,3-dioxo-1,3-dihydroisobenzofuran-4-yl)acetamide (2.05 g). Yield: 76.7%. MS (m/e): 425.14 (M-H⁻).

Example 6 ethyl 3-(4-acetamido-1,3-dioxoisoindolin-2-yl)-3-(3-ethoxy-4-methoxyphenyl)propionate To a reaction flask were added 3-(4-acetylamino-1,3-dioxoisoindolin-2-yl)-3-(3-ethoxy-4-methoxyphenyl)propionic acid (0.3 g), 6-chloro-1-hydroxybenzotriazole (0.18 g) and 1-(3-dimethylaminopropyl)-3-ethylcarbodiimide hydrochloride (0.2 g). DCM (4 mL) was added into the mixture. After the resultant mixture was completely dissolved at room temperature, ethanol (0.25 mL) was added. The mixture was stirred at room temperature overnight. HPLC showed that the reaction was completed. Water was added to quench the reaction. The reaction solution was concentrated under reduced pressure with a water pump. The resultant crude product was purified with silica gel column chromatography (eluent was DCM:EA=30:1 to 20:1) to give the pale yellow title compound (0.17 g, HPLC purity: 99.65%). Yield: 54.4%. MS (m/e): 477.28 (M+Na⁺).

Example 7 methyl (R)-3-(4-amino-1,3-dioxoisoindolin-2-yl)-3-(3-ethoxy-4-methoxyphenyl)propionate Methyl 3-amino-3-(3-ethoxy-4-methoxyphenyl)propionate hydrochloride (5.0 g) was dissolved in water (100 mL). pH was adjusted to 9 with saturated aqueous solution of sodium carbonate. The aqueous phase was extracted with DCM (50 mL×4). The organic phases were combined, washed once with saturated aqueous solution of sodium chloride (40 mL), dried over anhydrous sodium sulfate and filtered The filtrate was concentrated under reduced pressure with a water pump to give an oily product, i.e. methyl 3-amino-3-(3-ethoxy-4-methoxyphenyl)propionate (4.4 g, which was directly used in the next reaction). Yield: 100%.

To a reaction flask were added methyl 3-amino-3-(3-ethoxy-4-methoxyphenyl)propionate (14.0 g) and N-(tert-butoxycarbonyl)-L-leucine monohydrate (7.15 g). Methyl tert-butyl ether (490 mL) was added into the mixture. The resultant mixture was heated to 35° C. and stirred for 1 hour. The resultant mixture was slowly cooled to the room temperature and stirred overnight to precipitate a large amount of white solids. The reaction solution was filtered under reduced pressure. The filter cake was washed once with methyl tert-butyl ether (30 L). The filter cake was collected and dried in the air to give a white solid product, i.e. methyl (R)-3-amino-3-(3-ethoxy-4-methoxyphenyl)propionate N-(tert-butoxycarbonyl)-L-leucine salt (11 g, optical purity: 98.64%). Yield: 41.1%.

Methyl (R)-3-amino-3-(3-ethoxy-4-methoxyphenyl)propionate N-(tert-butoxycarbonyl)-L-leucine salt (12.1 g) was dissolved in water (100 mL). pH was adjusted to 9 with saturated aqueous solution of sodium carbonate. The aqueous phase was extracted with ethyl acetate (50 mL×4). The organic phases were combined and washed once with saturated aqueous solution of sodium chloride (60 mL), dried over anhydrous sodium sulfate and filtered. The filtrate was concentrated under reduced pressure with a water pump (35° C.) to obtain an oily product, i.e. methyl (R)-3-amino-3-(3-ethoxy-4-methoxyphenyl)propionate (5.62 g, optical rotation was measured $[\alpha]_D^{20}$=-14.5° (C=0.02, EtOH), which was directly used in the next reaction). Yield: 100%.

Methyl (R)-3-(3-ethoxy-4-methoxyphenyl)-3-(4-nitro-1,3-dioxoisoindoline-2-yl)propionate (5.28 g, HPLC purity: 98.62%) was prepared with methyl (R)-3-amino-3-(3-ethoxy-4-methoxyphenyl)propionate (4.9 g) and 3-nitrophthalic anhydride (4.48 g) in accordance with the preparation process in Example 1. Yield: 63.7%. MS (m/e): 429.12 (M+H⁺).

The title compound (3.2 g, HPLC purity: 97.26%, optical purity: 99.05%) was prepared with methyl (R)-3-(3-ethoxy-4-methoxyphenyl)-3-(4-nitro-1,3-dioxoisoindoline-2-yl) propionate (5.06 g) in accordance with the preparation process in Example 2. The optical rotation was measure $[\alpha]_D^{20}$=+12.55° (C=0.02, acetonitrile). Yield: 69%. MS (m/e): 399.15 (M+H⁺).

Example 8 methyl (S)-3-(4-amino-1,3-dioxoisoindolin-2-yl)-3-(3-ethoxy-4-methoxyphenyl)propionate Methyl (S)-3-amino-3-(3-ethoxy-4-methoxyphenyl)propionate N-(tert-butoxycarbonyl)-D-leucine salt (10 g, HPLC purity: 98.83%, optical purity: 99.15%) was prepared with methyl 3-amino-3-(3-ethoxy-4-methoxyphenyl)propionate (14.0 g) and N-(tert-butoxycarbonyl)-D-leucine monohydrate (7.15 g) in accordance with the preparation process in Example 7. Yield: 37.3%.

An oily product, i.e. methyl (S)-3-amino-3-(3-ethoxy-4-methoxyphenyl)propionate (5.3 g, optical rotation was measured $[\alpha]_D^{20}$=+14.1° (C=0.02, ethanol), which was directly used in the next reaction) was prepared with methyl (S)-3-amino-3-(3-ethoxy-4-methoxyphenyl)propionate N-(tert-butoxycarbonyl)-D-leucine salt (10 g) in accordance with the preparation process in Example 7.

Methyl (S)-3-(3-ethoxy-4-methoxyphenyl)-3-(4-nitro-1,3-dioxoisoindoline-2-yl)propionate (3.84 g, HPLC purity: 98.13%) was prepared with methyl (S)-3-amino-3-(3-ethoxy-4-methoxyphenyl)propionate (3.92 g) and 3-nitrophthalic anhydride (3.1 g) in accordance with the preparation process in Example 1. Yield: 58%. MS (m/e): 429.12 (M+H⁺).

The title compound (1.92 g, HPLC purity: 99.32%, optical purity: 99.25%; the optical rotation was measured $[\alpha]_D^{20}$=-11.93° (C=0.02, acetonitrile) was prepared with methyl (R)-3-(3-ethoxy-4-methoxyphenyl)-3-(4-nitro-1,3-dioxoisoindoline-2-yl)propionate (2.63 g) in accordance with the preparation process in Example 2. Yield: 48%. MS (m/e): 399.15 (M+H⁺).

Example 9 methyl (R)-3-(4-acetamido-1,3-dioxoisoindolin-2-yl)-3-(3-ethoxy-4-methoxyphenyl)propionate The title compound (12.0 g, HPLC purity: 99.40%, optical purity: 99.60%) was prepared with methyl (R)-3-amino- 3-(3-ethoxy-4-methoxyphenyl)propionate (10.44 g) and N-(1,3-dioxo-1,3-dihydroisobenzofuran-4-yl)acetamide (8.5 g) in accordance with the preparation process in Example 1. The optical rotation was measured $[\alpha]_D^{20}$=+11.2° (C=0.02, acetonitrile). Yield: 66.1%.

$^1$HNMR(CDCl$_3$, 400 MHz) δ 9.519 (bs, 1H), 8.750-8.729 (d, 1H), 7.651-7.612 (dd, 1H), 7.476-7.456 (dd, 1H), 7.081-7.054 (m, 2H), 6.832-6.810 (d, 1H), 5.734-5.695 (q, 1H), 4.130-4.078 (q, 2H), 3.840 (s, 3H), 3.812-3.745 (q, 1H), 3.648 (s, 3H), 3.217-3.162 (q, 1H), 2.258 (s, 3H), 1.475-1.440 (t, 3H). MS (m/e): 441.16 (M+H$^+$).

Example 10 methyl (S)-3-(4-acetamido-1,3-dioxoisoindolin-2-yl)-3-(3-ethoxy-4-methoxyphenyl)propionate The title compound (6.6 g, HPLC purity: 98.83%, optical purity: 99.73%) was prepared with methyl (S)-3-amino-3-(3-ethoxy-4-methoxyphenyl)propionate and N-(1,3-dioxo-1,3-dihydroisobenzofuran-4-yl)acetamide (4.1 g) in accordance with the preparation process in Example 1. The optical rotation was measured $[\alpha]_D^{20}$=−11.6° (C=0.02, ACN). Yield: 76.1%.

$^1$HNMR (CDCl$_3$, 400 MHz) δ 9.519 (bs, 1H), 8.750-8.729 (d, 1H), 7.651-7.612 (dd, 1H), 7.476-7.456 (dd, 1H), 7.081-7.054 (m, 2H), 6.832-6.810 (d, 1H), 5.734-5.695 (q, 1H), 4.130-4.078 (q, 2H), 3.840 (s, 3H), 3.812-3.745 (q, 1H), 3.648 (s, 3H), 3.217-3.162 (q, 1H), 2.258 (s, 3H), 1.475-1.440 (t, 3H). MS (m/e): 441.16 (M+H$^+$).

Example 11 propyl 3-(4-acetamido-1,3-dioxoisoindolin-2-yl)-3-(3-ethoxy-4-methoxyphenyl)propionate The title compound (0.12 g, HPLC purity: 99.32%) was prepared with 3-(4-acetamido-1,3-dioxoisoindolin-2-yl)-3-(3-ethoxy-4-methoxyphenyl)propionic acid (0.3 g) and n-propanol in accordance with the preparation process in Example 6. Yield: 36%. MS (m/e): 491.17 (M+Na$^+$).

Example 12 isopropyl 3-(4-acetamido-1,3-dioxoisoindolin-2-yl)-3-(3-ethoxy-4-methoxyphenyl)propionate The title compound (0.14 g, HPLC purity: 98.93%) was prepared with 3-(4-acetamido-1,3-dioxoisoindolin-2-yl)-3-(3-ethoxy-4-methoxyphenyl)propionic acid (0.3 g) and isopropanol in accordance with the preparation process in Example 6. Yield: 42%. MS (m/e): 491.16 (M+Na$^+$).

Example 13 butyl 3-(4-acetamido-1,3-dioxoisoindolin-2-yl)-3-(3-ethoxy-4-methoxyphenyl)propionate The title compound (0.22 g, HPLC purity: 99.46%) was prepared with 3-(4-acetamido-1,3-dioxoisoindolin-2-yl)-3-(3-ethoxy-4-methoxyphenyl)propionic acid (0.3 g) and n-butanol in accordance with the preparation process in Example 6. Yield: 61%. MS (m/e): 505.20 (M+Na$^+$).

Example 14 methyl 3-(4-(2-chloroacetamino)-1,3-dioxoisoindolin-2-yl)-3-(3-ethoxy-4-methoxyphenyl)propionate To a reaction flask were added methyl 3-(4-amino-1,3-dioxoisoindolin-2-yl)-3-(3-ethoxy-4-methoxyphenyl)propionate (700 mg), chloroacetyl chloride (218 mg), potassium carbonate (486 mg) and DCM (12 mL). The mixture was stirred at the room temperature overnight. HPLC showed that the reaction was completed. Water (30 mL) and DCM (50 mL) were added to the reaction solution. The mixture was extracted. The aqueous phase was back extracted with DCM (2×50 mL). DCM was combined. DCM was washed with saturated aqueous solution of NaCl, extracted, dried over anhydrous MgSO$_4$, filtered and concentrated to dryness to give a crude product, i.e. methyl 3-(4-(2-chloroacetamido)-1,3-dioxoisoindolin-2-yl)-3-(3-ethoxy-4-methoxyphenyl)propionate. The crude product was purified with silica gel column chromatography (eluent: PE:EA=10:1 to 4:1) to give a pure product of the title compound (220 mg, HPLC purity: 99.78%). Yield: 26%. MS (m/e): 497.19 (M+Na$^+$).

Example 15 methyl 3-(4-(2-(dimethylamino)acetamido)-1,3-dioxoisoindolin-2-yl)-3-(3-ethoxy-4-methoxy phenyl)propionate To a reaction flask were added methyl 3-(4-(2-chloroacetamido)-1,3-dioxoisoindolin-2-yl)-3-(3-ethoxy-4-methoxyphenyl)propionate (200 mg), dimethylamine hydrochloride (52 mg), potassium carbonate (116 mg) and acetone (10 mL). The mixture was stirred at the room temperature for 50 hours. HPLC showed that the reaction was completed. Water (40 mL) and EA (40 mL) were added to the reaction solution and the mixture was extracted. The aqueous phase was back extracted with EA (30 mL). The organic phases were combined, washed with saturated aqueous solution of NaCl, extracted, dried over anhydrous MgSO$_4$, filtered and concentrated to dryness to give a crude product, i.e. methyl 3-(4-(2-(dimethylamino)acetamido)-1,3-dioxoisoindolin-2-yl)-3-(3-ethoxy-4-methoxy phenyl)propionate. The crude product was purified with silica gel column chromatography (eluent: DCM:MeOH=200:1) to give a pure product of the title compound (100 mg, HPLC purity: 96.44%). Yield: 49%. MS (m/e): 484.27 (M+H$^+$).

Example 16 methyl 3-(4-(dimethylamino)-1,3-dioxoisoindolin-2-yl)-3-(3-ethoxy-4-methoxyphenyl)propionate To a reaction flask were added methyl 3-(4-amino-1,3-dioxoisoindolin-2-yl)-3-(3-ethoxy-4-methoxyphenyl)propionate (500 mg), an aqueous solution of formaldehyde (9 mL), Pd/C (50 mg, Pd content: 10%) and methanol (20 mL). The air was replaced with a hydrogen balloon three times. The reaction solution was stirred at the room temperature for 100 hours. TLC showed that the reaction was completed. The reaction solution was filtered. The filtrate was concentrated under reduced pressure with a water pump to give a crude product, i.e. methyl 3-(4-(dimethylamino)-1,3-dioxoisoindolin-2-yl)-3-(3-ethoxy-4-methoxyphenyl)propionate. The crude product was purified with silica gel column chromatography (eluent: PE:EA=4:1) to give a pure product of the title compound (176 mg, HPLC purity: 96.67%). Yield: 32.9%. MS (m/e): 427.18 (M+H$^+$).

Example 17 methyl 3-(4-(2-hydroxyacetamido)-1,3-dioxoisoindolin-2-yl)-3-(3-ethoxy-4-methoxyphenyl) propionate To a reaction flask were added 2-(benzyloxy)acetic acid (318 mg) and DCM (10 mL). Sulfoxide chloride (0.27 mL) and then DMF (1 mL) were added in the mixture with stirring at the room temperature. The resultant mixture was stirred at the room temperature for 18 hours. The reaction solution was concentrated with a water pump and an oil pump under reduced pressure to obtain 2-(benzyloxy)acetyl chloride (347 mg) as an oily product, which was directly used in the next reaction.

To a reaction flask were added methyl 2-(benzyloxy)acetyl chloride (347 mg), 3-(4-amino-1,3-dioxoisoindolin-2-yl)-3-(3-ethoxy-4-methoxyphenyl)propionate (500 mg), potassium carbonate (191 mg) and DCM (10 mL). The mixture was stirred at the room temperature for 18 hours. HPLC showed that the reaction was completed. Water (40 mL) and DCM (100 mL) were added to the reaction solution. The mixture was extracted. The aqueous phase was back extracted with DCM (2×30 mL). DCM were combined. The combined DMC was washed with saturated aqueous solution of NaCl, extracted, dried over anhydrous MgSO$_4$, filtered and concentrated to dryness to give a crude product. The crude product was purified with silica gel column chromatography (eluent: PE:EA=4:1) to give methyl 3-(4-(2-(benzyloxy)acetamido)-1,3-dioxoisoindoline-2-yl)-3-(3-ethoxy-4-methoxyphenyl)propionate (234 mg, HPLC purity: 95.88%). Yield: 34.2%. MS (m/e): 569.21 (M+Na$^+$).

To a reaction flask were added methyl 3-(4-(2-(benzyloxy)acetamido)-1,3-dioxoisoindolin-2-yl)-3-(3-ethoxy-4-methoxybenz ene)propionate (234 mg), Pd/C (24 mg, Pd content: 10%), methanol (17 mL) and EA (7 mL). The air was replaced with a hydrogen balloon three times. The mixture was stirred at the room temperature to react for 40 hours. HPLC showed that the reaction was completed. The reaction solution was filtered. The filtrate was concentrated under reduced pressure with a water pump to give a crude product, i.e. methyl 3-(4-(2-hydroxyacetamido)-1,3-dioxoisoindolin-2-yl)-3-(3-ethoxy-4-methoxyphenyl) propionate. The crude product was purified with silica gel column chromatography (eluent: PE:EA=2:1) to give the title compound (89 mg, HPLC purity: 98.70%). Yield: 45.6%. MS (m/e): 479.17 (M+Na$^+$).

Example 18 methyl 3-(4-acetamido-1,3-dioxoisoindolin-2-yl)-3-(3-ethoxy-4-isopropoxyphenyl)propionate 3-ethoxy-4-isopropoxybenzaldehyde (2.8 g, HPLC purity: 98.56%) was prepared with 3-ethoxy-4-hydroxybenzaldehyde (3.0 g) and bromoisopropane in accordance with the preparation process in Example 3. Yield: 76%.

3-amino-3-(3-ethoxy-4-isopropoxyphenyl)propionic acid (2.7 g) (HPLC purity: 99.43%) was prepared with 3-ethoxy-4-isopropoxybenzaldehyde (2.8 g) in accordance with the preparation process in Example 1. Yield: 74%. MS (m/e): 268.15 (M+H$^+$).

Methyl 3-amino-3-(3-ethoxy-4-isopropoxyphenyl)propionate hydrochloride (2.4 g, HPLC purity: 98.69%) was prepared with 3-amino-3-(3-ethoxy-4-isopropoxyphenyl)propanoic acid (2.7 g) in accordance with the preparation process in Example 1. Yield: 75%. MS (m/e): 282.16 (M+H$^+$).

The title compound (237 mg, HPLC purity: 97.30%) was prepared with methyl 3-amino-3-(3-ethoxy-4-isopropoxyphenyl)propionate hydrochloride (1.5 g) and N-(1,3-dioxo-1,3-dihydroisobenzofuran-4-yl)acetamide (1.0 g) in accordance with the preparation process in Example 1. Yield: 10.4%. MS (m/e): 491.20 (M+Na$^+$).

Example 19 methyl 3-(4-fluoro-1,3-dioxoisoindolin-2-yl)-3-(3-ethoxy-4-methoxyphenyl)propionate The title compound (546 mg, HPLC purity: 99.85%) was prepared with 3-fluorophthalic anhydride (275 mg) and methyl 3-amino-3-(3-ethoxy-4-methoxyphenyl)propionate hydrochloride (526 Mg) in accordance with the preparation process in Example 1. Yield: 82%. MS (m/e): 424.16 (M+Na$^+$).

Example 20 methyl 3-(4-acetamido-1,3-dioxoisoindolin-2-yl)-3-(3-ethoxy-4-cyclopentyloxyphenyl)propionate 3-ethoxy-4-cyclopentylbenzaldehyde (4.2 g, HPLC purity: 96.97%) was prepared with 3-ethoxy-4-hydroxybenzaldehyde (3.0 g) and bromocyclopentane in accordance with the preparation process in Example 3. Yield: 99%.

3-amino-3-(3-ethoxy-4-cyclopentoxyphenyl)propionic acid (2.78 g, HPLC purity: 99.60%) was prepared with 3-ethoxy-4-cyclopentoxybenzaldehyde (4.2 g) in accordance with the preparation process in Example 1. Yield: 52.9%. MS (m/e): 294.16 (M+H$^+$).

methyl 3-amino-3-(3-ethoxy-4-cyclopentyloxyphenyl)propionate hydrochloride (3.25 g, HPLC purity: 99.60%) was prepared with 3-amino-3-(3-ethoxy-4-cyclopentyloxyphenyl)propanoic acid (2.78 g) in accordance with the preparation process in Example 1. Yield: 100%. MS (m/e): 308.18 (M+H$^+$).

The title compound (606 mg, PLC purity: 94.97%) was prepared with methyl 3-amino-3-(3-ethoxy-4-cyclopentyloxyphenyl)propionate hydrochloride (1.8 g) and N-(1,3-dioxo-1,3-dihydroisobenzofuran-4-yl)acetamide (1.0 g) in accordance with the preparation process in Example 1. Yield: 25.1%. MS (m/e): 517.23 (M+Na$^+$).

Example 21 methyl 3-(4-methyl-1,3-dioxoisoindolin-2-yl)-3-(3-ethoxy-4-methoxyphenyl)propionate The title compound (609 mg, HPLC purity: 99.58%) was prepared with 3-methylphthalic anhydride (330 mg) and methyl 3-amino-3-(3-ethoxy-4-methoxyphenyl)propionate hydrochloride (648 mg) in accordance with the preparation process in Example 1. Yield: 75%. MS (m/e): 420.16 (M+Na$^+$).

Example 22 methyl 3-(5-fluoro-1,3-dioxoisoindolin-2-yl)-3-(3-ethoxy-4-methoxyphenyl)propionate The title compound (350 mg, HPLC purity: 98.02%) was prepared with 4-fluorophthalic anhydride (271 mg) and methyl 3-amino-3-(3-ethoxy-4-methoxyphenyl)propionate hydrochloric (526 mg) in accordance with the preparation process in Example 1. Yield: 53%. MS (m/e): 424.14 (M+Na$^+$).

Example 23 methyl 3-(4,7-dichloro-1,3-dioxoisoindolin-2-yl)-3-(3-ethoxy-4-methoxyphenyl)propionate The title compound (100 mg, HPLC purity: 99.20%) was prepared with 3,6-dichlorophthalic anhydride (500 mg) and methyl 3-amino-3-(3-ethoxy-4-methoxyphenyl)propionate hydrochloride (666 mg) in accordance with the preparation process in Example 1. Yield: 7.2%.
$^1$HNMR (CDCl$_3$, 400 MHz) δ 7.530-7.527 (d, 2H), 7.123-7.092 (m, 2H), 6.825-6.804 (d, 1H), 5.767-5.728 (q, 1H), 4.133-4.081 (q, 2H), 3.840 (s, 3H), 3.816-3.774 (q, 1H), 3.651 (s, 3H), 3.237-3.181 (q, 1H), 1.478-1.443 (t, 3H). MS (m/e): 474.12 (M+Na$^+$).

Example 24 methyl 3-(4-(N-methylacetamido)-1,3-dioxoisoindolin-2-yl)-3-(3-ethoxy-4-methoxyphenyl)propionate To a reaction flask were added methyl 3-(4-acetylamino-1,3-dioxoisoindolin-2-yl)-3-(3-ethoxy-4-methoxyphenyl)propionate (505 mg), iodomethane (177 mg) and potassium carbonate (314 mg). DMF (5 mL) was added in the mixture. The resultant mixture was stirred at the room temperature for 100 hours. HPLC showed that the reaction was completed. Water (30 mL) and DCM (200 mL) were added to the reaction solution. The solution was extracted. The organic phase was collected and concentrated under reduced pressure to give a crude product. The resultant crude product was purified with silica gel column chromatography (eluent: PE:EA=20:1 to 1:1) to give the title compound (410 mg, HPLC purity: 98.12%). Yield: 79.5%. MS (m/e): 477.25 (M+Na$^+$).

Example 25 methyl 3-(5-acetamido-1,3-dioxoisoindolin-2-yl)-3-(3-ethoxy-4-methoxyphenyl)propionate To a reaction flask were added 4-Nitrophthalic acid (1.5 g) and acetic anhydride (15 mL). The mixture was stirred at 125° C. for 2 hours. The reaction solution was concentrated in turn with a water pump and an oil pump under reduced pressure to obtain 4-nitrophthalic anhydride (1.4 g), which was directly used in the next reaction.

Methyl 3-(3-ethoxy-4-methoxyphenyl)-3-(5-nitro-1,3-dioxoisoindolin-2-yl)propionate (2.2 g, HPLC purity: 97.65%) was prepared with 4-nitrophthalic anhydride (1.4 g) and methyl 3-amino-3-(3-ethoxy-4-methoxyphenyl)propionate hydrochloride (1.58 g) in accordance with the preparation process in Example 1. Yield: 94%. MS (m/e): 429.12 (M+H$^+$).

Methyl 3-(3-ethoxy-4-methoxyphenyl)-3-(5-amino-1,3-dioxoisoindoline-2-yl)propionate (500 mg, HPLC purity: 98.25%) was prepared with methyl 3-(3-ethoxy-4-methoxyphenyl)-3-(5-nitro-1,3-dioxoisoindoline-2-yl)propionate (678 mg) in accordance with the preparation process in Example 2. Yield: 79.2%. MS (m/e): 421.25 (M+Na$^+$).

To a reaction flask were added methyl 3-(3-ethoxy-4-methoxyphenyl)-3-(5-amino-1,3-dioxoisoindolin-2-yl)propionate (250 mg), acetic anhydride (83 mg), triethylamine (190 mg), DMAP (8 mg) and DCM (2.5 mL). The mixture was stirred at the room temperature overnight. HPLC showed that the reaction was completed. A drop of water was added to the reaction solution to quench the reaction. The reaction solution was concentrated in turn with a water pump under reduced pressure to give a crude product. The crude product was purified with silica gel column chromatography (eluent: PE:EA=1:1) to give the title compound (170 mg, HPLC purity: 98.39%). Yield: 61.6%. MS (m/e): 463.22 (M+Na$^+$).

Example 26 methyl 3-(4-acetamido-1,3-dioxoisoindolin-2-yl)-3-(3-(benzyloxy)-4-methoxyphenyl)propionate The title compound (806 mg, HPLC purity: 99.46%) was prepared with 3-hydroxy-4-methoxybenzaldehyde (5.0 g) by replacing iodomethane with bromobenzyl in accordance with the preparation process in Example 3. MS (m/e): 525.14 (M+Na$^+$).

Example 27 methyl 3-(4-(N-methyl-tert-butoxycarbonylamino)-1,3-dioxoisoindolin-2-yl)-3-(3-ethoxy-4-methoxyphenyl)propionate To a reaction flask were added methyl 3-(4-amino-1,3-dioxoisoindolin-2-yl)-3-(3-ethoxy-4-methoxyphenyl)propionate (500 mg), Boc$_2$O (958 mg) and DMAP (31 mg). THF (15 mL) was added in the mixture. The reaction solution was stirred at the room temperature overnight. TLC showed that the raw material reaction was completed. The reaction solution was concentrated under reduced pressure with a water pump to give a crude product. The crude product was purified with silica gel column chromatography (eluent: PE:EA=15:1 to 5:1) to give methyl 3-(4-(di-tert-butoxycarbonylamino)-1,3-dioxoisoindoline-2-yl)-3-(3-ethoxy-4-methoxyphenyl)propionate (634 mg, HPLC purity: 98.28%). Yield: 84.4%. MS (m/e): 599.25 (M+H$^+$).

Methyl 3-(4-(di-tert-butoxycarbonylamino)-1,3-dioxoisoindolin-2-yl)-3-(3-ethoxy-4-methoxy phenyl)propionate (634 mg) was dissolved in DCM (200 mL). Trifluoroacetic acid (1 mL) was added in the mixture. The reaction solution was stirred at the room temperature for 15 minutes. TLC showed that the reaction was completed. Saturated NaHCO$_3$ (30 mL) was added to the reaction solution to quench the reaction and the mixture was stirred for 10 minutes. The solution was extracted with separatory funnel. The organic phase was dried over anhydrous MgSO$_4$ and filtered. The filtrate was collected and concentrated under reduced pressure in turn with a water pump and an oil pump to give a crude product. The crude product was purified with silica gel column chromatography (eluent: PE:EA=15:1 to 5:1) to give methyl 3-(4-(tert-butoxycarbonylamino)-1,3-dioxoisoindoline-2-yl)-3-(3-ethoxy-4-methoxyphenyl)propionate (354 mg, HPLC purity: 99.41%). Yield: 67%.

To a reaction flask were added methyl 3-(4-(tert-butoxycarbonylamino)-1,3-dioxoisoindolin-2-yl)-3-(3-ethoxy-4-methoxyphenyl)propionate (300 mg), methyl iodide (171 mg) and potassium carbonate (250 mg). DMF (6 mL) was added in the mixture. The mixture was stirred overnight at the room temperature. HPLC showed that the reaction was completed. The reaction solution was diluted with EA (250 mL). Firstly, the organic phase was washed with water (40 mL). The organic phase was then washed with saturated aqueous solution of NaCl (30 mL×4). The organic phase was dried over anhydrous MgSO$_4$, filtered. The filtrate was collected and concentrated under reduced pressure in turn with a water pump and an oil pump to obtain the title compound (201 mg, HPLC purity 95.54%). Yield: 65.3%. MS (m/e): 513.22 (M+H$^+$).

Example 28 methyl 3-(4-(methylamino)-1,3-dioxoisoindolin-2-yl)-3-(3-ethoxy-4-methoxyphenyl)propionate Methyl 3-(4-(N-methyl tert-butoxycarbonylamino)-1,3-dioxoisoindolin-2-yl)-3-(3-ethoxy-4-methoxy phenyl)propionate (201 mg) was dissolved in DCM (2 mL). Trifluoroacetic acid (2 mL) was added in the mixture. The reaction solution was stirred at the room temperature for 2 hours. TLC showed that the reaction was completed. The reaction solution was concentrated under reduced pressure with a water pump to give a crude product. The crude product was purified with silica gel column chromatography (eluent: PE:EA=10:1 to 5:1) to give the title compound (120 mg, HPLC purity: 99.95%). Yield: 74%. MS (m/e): 435.14 (M+Na$^+$).

Example 29 methyl 3-(4-acetamido-1,3-dioxoisoindolin-2-yl)-3-(3-propoxy-4-methoxyphenyl)propionate The title compound (886 mg, HPLC purity 98.496%) was prepared with 3-hydroxy-4-methoxybenzaldehyde (5.0 g) and n-bromopropane in accordance with the preparation process in Example 3; MS (m/e): 477.14 (M+Na$^+$).

Example 30 methyl 3-(4-acetamido-1,3-dioxoisoindolin-2-yl)-3-(3-cyclopentyloxy-4-methoxyphenyl)propionate The title compound (1.086 g, HPLC purity: 98.51%) was prepared with 3-hydroxy-4-methoxybenzaldehyde (5.0 g) and bromocyclopentanthe in accordance with the preparation process in Example 3.
$^1$HNMR (CDCl$_3$, 400 MHz) δ 9.537 (bs, 1H), 8.751-8.730 (d, 1H), 7.655-7.616 (t, 1H), 7.483-7.464 (d, 1H), 7.089-7.084 (d, 1H), 7.054-7.028 (q, 1H), 6.818-6.797 (d, 1H), 5.732-5.693 (q, 1H), 4.794-4.764 (m, 1H), 3.813 (s, 3H), 3.824-3.756 (q, 1H), 3.651 (s, 3H), 3.210-3.155 (q, 1H), 2.261 (s, 3H), 1.979-1.799 (m, 6H), 1.616-1.593 (m, 2H). MS (m/e): 503.17 (M+Na$^+$).

Example 31 methyl 3-(4-acetamido-1,3-dioxoisoindolin-2-yl)-3-(3-ethoxy-4-propoxyphenyl)propionate The title compound (227 mg, HPLC purity: 96.34%) was prepared with 3-ethoxy-4-hydroxybenzaldehyde) (3.0 g) and n-bromopropane in accordance with the preparation process in Example 3.

$^1$HNMR (CDCl$_3$, 400 MHz) δ 9.529 (bs, 1H), 8.750-8.729 (d, 1H), 7.652-7.613 (t, 1H), 7.476-7.457 (d, 1H), 7.065-7.031 (m, 2H), 6.831-6.810 (d, 1H), 5.725-5.686 (q, 1H), 4.111-4.058 (q, 2H), 3.952-3.919 (t, 2H), 3.823-3.755 (q, 1H), 3.647 (s, 3H), 3.202-3.147 (q, 1H), 2.261 (s, 3H), 1.846-1.793 (m, 2H), 1.447-1.412 (t, 3H), 1.029-0.992 (t, 3H). MS (m/e): 491.21 (M+Na$^+$).

Example 32 methyl 3-(4-hydroxy-1,3-dioxoisoindolin-2-yl)-3-(3-ethoxy-4-methoxyphenyl)propionate The title compound (340 mg, HPLC purity: 97.97%) was prepared with 3-hydroxyphthalic anhydride (300 mg) and methyl 3-amino-3-(3-ethoxy-4-methoxyphenyl)propionate hydrochloride (580 mg) in accordance with the preparation process in Example 1. Yield: 46%. MS (m/e): 422.16 (M+Na$^+$).

Example 33 methyl 3-(4-acetoxy-1,3-dioxoisoindolin-2-yl)-3-(3-ethoxy-4-methoxyphenyl)propionate To a reaction flask were added methyl 3-(4-hydroxy-1,3-dioxoisoindolin-2-yl)-3-(3-ethoxy-4-methoxyphenyl)propionate (300 mg), acetyl chloride (177 mg), triethylamine (228 mg) and DCM (5 mL). The mixture was stirred at the room temperature overnight. HPLC showed that the reaction was completed. 1 N aqueous solution of hydrochloric acid (30 mL) and DCM (100 mL) were added to the reaction solution. The mixture was extracted. The organic phase was washed with saturated aqueous solution of NaCl, extracted, dried over anhydrous magnesium sulfate, filtered, and concentrated to dryness to give a crude product. The crude product was purified with silica gel column chromatography (eluent: PE:EA=10:1 to 2:1) to give the title compound (179 mg, HPLC purity: 97.95%). Yield: 53.9%. MS (m/e): 464.14 (M+Na$^+$).

Example 34 methyl 3-(4-amino-7-hydroxy-1,3-dioxoisoindolin-2-yl)-3-(3-ethoxy-4-methoxyphenyl)propionate To a reaction flask were added 3-tert-butoxycarbonylamino-6-hydroxyphthalate (2.0 g), methyl 3-amino-3-(3-ethoxy-4-methoxyphenyl)propionate hydrochloride (3.56 g) and pyridine (40 mL). The flask was placed in an oil bath and heated to 100° C. The mixture was stirred for 38 hours. The reaction solution was cooled to the room temperature and concentrated under reduced pressure with a water pump to obtain a crude product. The crude product was purified with silica gel column chromatography (eluent: PE:EA=5:1) to give methyl 3-(4-(tert-butoxycarbonylamino)-7-hydroxy-1,3-dioxoisoindoline-2-yl)-3-(3-ethoxy-4-methoxyphenyl) propionate (2.149 g, HPLC purity 99.22%). Yield 67.9%. MS (m/e): 515.20 (M+H$^+$).

Methyl 3-(3-ethoxy-4-methoxyphenyl)-3-(4-(tert-butoxycarbonylamino)-7-hydroxy-1,3-dioxo isoindoline-2-yl)propionate (2.148 g) was dissolved in dichloromethane (50 mL). Trifluoroacetic acid (6 mL) was added in the mixture. The reaction solution was stirred at the room temperature for 6 hours. TLC showed that the reaction was completed. The reaction solution was concentrated with a water pump under reduced pressure to obtain a crude product. The crude product was pulped with PE/DCM=1:1 (10 mL) and purified to give the title compound (1.28 g, HPLC purity: 99.36%). Yield: 74%. MS (m/e): 437.21 (M+Na$^+$).

Example 35 methyl 3-(4-amino-5-hydroxy-1,3-dioxoisoindolin-2-yl)-3-(3-ethoxy-4-methoxyphenyl)propionate To a reaction flask were added 4-hydroxyphthalic acid dimethyl (125 g) and concentrated H$_2$SO$_4$ (600 mL). The mixture was cooled to 0° C. with stirring. Fuming HNO$_3$ (39.44 g) was slowly dropwise added to the mixture. The temperature of the mixture was controlled at less than 5° C. The dropwise addition was completed in about 1 hour. The ice bath was removed and the temperature was raised to the room temperature. The reaction solution was stirred for 22 hours. HPLC showed that the reaction was completed. The reaction solution was slowly poured into ice water (1.4 kg) to quench the reaction. The aqueous phase was extracted by adding EA (600 mL×5). The organic phases were combined, dried over anhydrous MgSO$_4$ (25 g) and filtered. The filtrate was collected and concentrated under reduced pressure in turn with a water pump and an oil pump to give a crude product, i.e. 4-hydroxy-3-nitrophthalate dimethyl (169 g, HPLC purity: 36.54%), which was directly used in the next reaction. MS (m/e): 254.07 (M–H$^-$).

To a reaction flask were added 4-hydroxy-3-nitrophthalate dimethyl (164 g), benzyl bromide (135.9 g), potassium carbonate (400 g) and acetone (1730 L). The reaction flask was placed in an oil bath and heated to 70° C. The mixture was stirred for 23 hours. TLC showed that the reaction was completed. The mixture was cooled to the room temperature. The reaction solution was filtered under reduced pressure. The filter cake was washed with DCM (2000 mL). The filtrate was collected. The filtrate was concentrated under reduced pressure. DCM (2000 mL) and saturated aqueous solution of NaCl (1000 mL) were added to the concentrate. The resultant mixture was extracted. The organic phase was dried over anhydrous MgSO$_4$ (100 g), filtered and concentrated under reduced pressure with a water pump to give a crude yellow solid. The crude product was purified by recrystallizing with EA to give a white solid product, i.e. 4-benzyloxy-3-dimethyl nitrophthalate (40 g, HPLC purity: 96.96%). Yield: 18.1%. MS (m/e): 346.14 (M+H$^+$).

To a reaction flask were added 4-benzyloxy-3-nitrophthalate dimethyl ester (1.335 g) and EtOH (14 mL). The pre-prepared aqueous solution of NaOH (1.089 g NaOH in 7 mL water) was also added to the reaction flask. The flask was placed in an oil bath and heated to 70° C. The mixture was stirred for 7 hours. TLC showed that the reaction was completed. The reaction system was cooled to the room temperature. The reaction solution was concentrated under reduced pressure with a water pump until most of EtOH was removed. At room temperature, 4 mol/L aqueous solution of HCl was added to the concentrate to acidify until pH=2. A large amount of white solids were precipitated. The mixture was filtered under reduced pressure. The filter cake was collected and dried under reduced pressure with an oil pump to give a white solid product, i.e. 4-benzyloxy-3-nitrophthalic acid (1.089 g, HPLC purity: 99.72%). Yield: 88.8%. MS (m/e): 316.15 (M–H$^-$).

To a reaction flask were added 4-benzyloxy-3-nitrophthalic acid (1.089 g) and acetic anhydride (11 mL). The flask was placed in an oil bath and heated to 140° C. The mixture was stirred for 6 hours. The reaction solution was cooled to the room temperature and concentrated under reduced pressure with a water pump to obtain 1.02 g of crude product, i.e. 4-benzyloxy-3-nitrophthalic anhydride, which was directly used in the next reaction.

Methyl 3-(4-nitro-5-benzyloxy-1,3-dioxoisoindolin-2-yl)-3-(3-Ethoxy-4-methoxyphenyl)propionate (1.48 g, HPLC purity: 97.92%) was prepared with 4-benzyloxy-3-nitrophthalic anhydride (1.02 g) and methyl 3-amino-3-(3-ethoxy-4-methoxyphenyl)propionate hydrochloride (1.09 g) in accordance with the preparation process in Example 1. Yield: 78.1%. MS (m/e): 557.21 (M+Na$^+$).

The title compound (950 mg, HPLC purity: 98.45%) was prepared with methyl 3-(4-nitro-5-benzyloxy-1,3-dioxoisoindolin-2-yl)-3-(3-ethoxy-4-methoxyphenyl)propionate (1.48 g) in accordance with the preparation process in Example 2. Yield: 82.8%. MS (m/e): 437.10 (M+Na$^+$).

Example 36 methyl 3-(4-acetamido-1,3-dioxoisoindolin-2-yl)-3-(3-hydroxy-4-methoxyphenyl)propionate To a reaction flask were added methyl 3-(4-acetylamino-1,3-dioxoisoindolin-2-yl)-3-(3-(benzyloxy)-4-methoxyphenyl)propionate (200 mg), Pd/C (57 mg, Pd content: 10%) and THF (10 mL). The air was replaced with a hydrogen balloon three times. The mixture was stirred at the room temperature for 16 hours. TLC showed that the reaction was completed. The reaction solution was filtered. The filtrate was concentrated under reduced pressure with a water pump to give a crude product. The crude product was purified with silica gel column chromatography (eluent: PE:EA=5:1 to 1:1) to give the title compound (116 mg, HPLC purity: 99.81%). Yield: 70.7%. MS (m/e): 435.13 (M+Na$^+$).

Example 37 methyl 3-(4-acetamido-1,3-dioxoisoindolin-2-yl)-3-(3-ethoxy-4-(benzyloxy)phenyl)propionate The title compound (881 mg, HPLC purity: 97.54%) was prepared with 3-ethoxy-4-hydroxybenzaldehyde (3.0 g) by replacing iodomethane with bromobenzyl in accordance with the preparation process in Example 3. MS (m/e): 539.21 (M+Na$^+$).

Example 38 methyl 3-(4-acetamido-1,3-dioxoisoindolin-2-yl)-3-(3-ethoxy-4-hydroxyphenyl)propionate The title compound (600 mg, HPLC purity: 97.25%) was prepared with methyl 3-(4-acetamido-1,3-dioxoisoindolin-2-yl)-3-(3-ethoxy-4-(benzyloxy)phenyl)propionate (765 mg) in accordance with the preparation process in Example 36. Yield: 95%. MS (m/e): 449.18 (M+Na$^+$).

Example 39 methyl 3-(4-acetamido-1,3-dioxoisoindolin-2-yl)-3-(3-methoxy-4-(benzyloxy)phenyl)propionate The title compound (1.615 g, HPLC purity: 96.81%) was prepared with 3-methoxy-4-hydroxybenzaldehyde (3.0 g) by replacing iodomethane with bromobenzyl in accordance with the preparation process in Example 3. MS (m/e): 525.18 (M+Na$^+$).

Example 40 methyl 3-(4-acetamido-1,3-dioxoisoindolin-2-yl)-3-(3-methoxy-4-hydroxyphenyl)propionate The title compound (856 mg, HPLC purity: 98.37%) was prepared with methyl 3-(4-acetamido-1,3-dioxoisoindolin-2-yl)-3-(3-methoxy-4-(benzyloxy)phenyl)propionate (1.468 g) in accordance with the preparation process in Example 36. MS (m/e): 435.15 (M+Na$^+$).

Example 41 methyl 3-(4-acetamido-1,3-dioxoisoindolin-2-yl)-3-phenylpropionate

The title compound (1.46 g, HPLC purity: 98.71%) was prepared with benzaldehyde (3.0 g) in accordance with the preparation process in Example 1. MS (m/e): 389.13 (M+Na$^+$).

Example 42 methyl 3-(4-acetamido-1,3-dioxoisoindolin-2-yl)-3-(3-chlorophenyl)propionate

The title compound (263 mg, HPLC purity: 98.54%) was prepared with 3-chlorobenzaldehyde (500 mg) in accordance with the preparation process in Example 1. MS (m/e): 423.14 (M+Na$^+$).

Example 43 methyl 3-(4-acetamido-1,3-dioxoisoindolin-2-yl)-3-(4-ethoxypheny)propionate

The title compound (0.86 g, HPLC purity: 97.83%) was prepared with 4-ethoxybenzaldehyde (1.9 g) in accordance with the preparation process in Example 1. MS (m/e): 411.15 (M+H$^+$).

Example 44 methyl 3-(4-Acetamido-1,3-dioxoisoindolin-2-yl)-3-(4-chlorophenyl)propionate

The title compound (260 mg, HPLC purity: 98.78%) was prepared with 4-chlorobenzaldehyde (500 mg) in accordance with the preparation process in Example 1. MS (m/e): 423.14 (M+Na$^+$).

Example 45 methyl 3-(4-(tert-butyloxycarbonylamino)-1,3-dioxoisoindolin-2-yl)-3-(3-ethoxy-4-methoxy phenyl)propionate To a reaction flask were added methyl 3-(4-amino-1,3-dioxoisoindolin-2-yl)-3-(3-ethoxy-4-methoxyphenyl)propionate (500 mg), Boc$_2$O (958 mg) and DMAP (31 mg). THF (15 mL) was added in the mixture. The resultant mixture was stirred at the room temperature overnight. TLC showed that the raw material reaction was completed. The reaction solution was concentrated under reduced pressure with a water pump to give a crude product. The crude product was purified with silica gel column chromatography (eluent: PE:EA=15:1 to 5:1) to give methyl 3-(4-(di-tert-butoxycarbonylamino)-1,3-dioxoisoindoline-2-yl)-3-(3-ethoxy-4-methoxyphenyl)propionate (634 mg, HPLC purity: 98.28%). Yield: 84.4%. MS (m/e): 599.25 (M+H$^+$).

Methyl 3-(4-(di-tert-butoxycarbonylamino)-1,3-dioxoisoindolin-2-yl)-3-(3-ethoxy-4-methoxy phenyl)propionate (634 mg) was dissolved in DCM (200 mL). Trifluoroacetic acid (1 mL) was added in the mixture. The reaction solution was stirred at the room temperature for 15 minutes. TLC showed that the reaction was completed. Saturated NaHCO$_3$ (30 mL) was added to the reaction solution to quench the reaction. The reaction solution was stirred for 10 minutes. The reaction solution was extracted with separatory funnel. The organic phase was dried over anhydrous MgSO$_4$ and filtered. The filtrate was collected and concentrated under reduced pressure in turn with a water pump and an oil pump to give a crude product. The crude product was purified with silica gel column chromatography (eluent: PE:EA=15:1 to 5:1) to give the title compound (354 mg, HPLC purity: 99.41%). Yield: 67%. MS (m/e): 499.20 (M+H$^+$).

Example 46 methyl 3-(4-acetamido-1,3-dioxoisoindolin-2-yl)-3-(3-isopropoxy-4-methoxyphenyl)propionate The title compound (403 mg, HPLC purity: 96.38%) was prepared with 3-hydroxy-4-methoxybenzaldehyde (5.0 g) and isopropyl bromide in accordance with the preparation process in Example 3. MS (m/e): 477.15 (M+Na$^+$).

Example 47 methyl 3-(4-acetamido-1,3-dioxoisoindolin-2-yl)-3-(4-(difluoromethoxy)-3-ethoxyphenyl)propionate The title compound (158 mg, HPLC purity: 95.36%) was prepared with 3-ethoxy-4-hydroxybenzaldehyde (5.0 g) and difluoroiodomethane in accordance with the preparation process in Example 3. MS (m/e): 477.14 (M+H$^+$).

Example 48 methyl 3-(4-acetamido-1,3-dioxoisoindolin-2-yl)-3-(3-ethoxy-4-(trifluoromethoxy)phenyl)propionate The title compound (105 mg, HPLC purity: 95.18%) was prepared with 3-ethoxy-4-hydroxybenzaldehyde (5.0 g) and trifluoroiodomethane in accordance with the preparation process in Example 3. MS (m/e): 495.13 (M+H$^+$).

Example 49 methyl 3-(4-acetamido-1,3-dioxoisoindolin-2-yl)-3-(3-(difluoromethoxy)-4-methoxyphenyl))propionate The title compound (109 mg, HPLC purity: 96.37%) was prepared with 3-hydroxy-4-methoxybenzaldehyde (5.0 g) and difluoroiodomethane in accordance with the preparation process in Example 3. MS (m/e): 463.12 (M+H$^+$).

Example 50 methyl 3-(4-acetamido-1,3-dioxoisoindolin-2-yl)-3-
(4-methoxy-3-(trifluoromethoxy)phenyl)propionate The title compound (116 mg, HPLC purity: 96.11%) was prepared with 3-hydroxy-4-methoxybenzaldehyde (5.0 g) and trifluoroiodomethane in accordance with the preparation process in Example 3. MS (m/e): 481.11 (M+H$^+$).

Example 51 ethyl (R)-3-(4-acetamido-1,3-dioxoisoindolin-2-yl)-
3-(3-ethoxy-4-methoxyphenyl)propionate To a reaction flask was added methyl (R)-3-amino-3-(3-ethoxy-4-methoxyphenyl)propionate hydrochloride (3.0 g). Tetrahydrofuran (30 mL) was added to dissolve methyl (R)-3-amino-3-(3-ethoxy-4-methoxyphenyl)propionate hydrochloride. The prepared aqueous solution of sodium hydroxide (2.5 g sodium hydroxide, 30 mL water) was added in the mixture at the room temperature. The resultant mixture was stirred at room temperature for 3 hours. TLC showed that the hydrolysis reaction was completed. The reaction solution was cooled to 0° C. and adjusted to pH=1-2 with concentrated hydrochloric acid (12 N, 5.25 mL). The reaction solution was concentrated under reduced pressure. The concentrate was co-boiled with acetonitrile (25 mL) to remove water twice to give a crude product, i.e. (R)-3-amino-3-(3-ethoxy-4-methoxyphenyl)propionate hydrochloride (6.5 g, HPLC purity: 98.66%), which was directly used in the next reaction. Yield: 100%.

Ethyl (R)-3-amino-3-(3-ethoxy-4-methoxyphenyl)propionate hydrochloride was prepared with ethyl (R)-3-amino-3-(3-ethoxy-4-methoxyphenyl)propionate hydrochloride (6.5 g) and ethanol (25 mL) in accordance with the preparation process in Example 1. A white solid product was obtained (3.15 g, HPLC purity: 94.51%, which was directly used in the next reaction).

The title compound (2.227 g, HPLC purity: 97.75%, optical purity: 100%) was prepared with ethyl (R)-3-amino-3-(3-ethoxy-4-methoxyphenyl)propionate hydrochloride (3.15 g) and N-(1,3-dioxo-1,3-dihydroisobenzofuran-4-yl)acetamide (1.8 g) in accordance with the preparation process in Example 1. Yield: 56.7%. MS (m/e): 477.18 (M+Na$^+$).

Example 52 ethyl (S)-3-(4-acetamido-1,3-dioxoisoindolin-2-yl)-
3-(3-ethoxy-4-methoxyphenyl)propionate The title compound (1.62 g, HPLC purity: 94.39%) was prepared with methyl (S)-3-amino-3-(3-ethoxy-4-methoxyphenyl)propionate hydrochloride (3.0 g) in accordance with the preparation process in Example 51. MS (m/e): 477.20 (M+Na$^+$).

Example 53 methyl (R)-3-(4-acetamido-1,3-dioxoisoindolin-2-yl)-3-(3-isopropoxy-4-methoxyphenyl)propionate The title compound (1.86 g, HPLC purity: 96.96%, optical purity: 99.03%) was prepared with methyl 3-amino-3-(3-isopropoxy-4-methoxyphenyl)propionate hydrochloride (6.0 g) in accordance with the preparation process in Example 7. MS (m/e): 477.18 (M+Na$^+$).

Example 54 methyl (S)-3-(4-acetamido-1,3-dioxoisoindolin-2-yl)-3-(3-isopropoxy-4-methoxyphenyl)propionate The title compound (1.62 g, HPLC purity: 96.44%, optical purity: 97.82%) was prepared with methyl 3-amino-3-(3-isopropoxy-4-methoxyphenyl)propionate hydrochloride (6.0 g) in accordance with the preparation process in Example 8. MS (m/e): 477.18 (M+Na$^+$).

Example 55 methyl 3-(4-acetamido-1,3-dioxoisoindolin-2-yl)-3-(benzo[d][1,3]dioxol-5-yl)propionate The title compound (207 mg, HPLC purity: 96.32%) was prepared with benzo[d][1,3]dioxole-5-carbaldehyde (prepared according to the method reported in RSC Advances, 2015, 5 (91), 74425-74437) (450 mg) in accordance with the preparation process in Example 1. MS (m/e): 411.14 (M+H$^+$).

Example 56 methyl 3-(4-acetamido-1,3-dioxoisoindolin-2-yl)-3-(2,3-dihydrobenzo[b][1,4]dioxin-6-yl)propionate The title compound (235 mg, HPLC purity: 97.58%) was prepared with 2,3-dihydrobenzo[b][1,4]dioxin-6-carbaldehyde (prepared according to the method reported in Journal of Medicine, Chemistry, 2007, 50 (17), 4122-4134) (492 mg) in accordance with the preparation process in Example 1. MS (m/e): 425.18 (M+H$^+$).

BIOLOGICAL EXAMPLES

Biological Example 1

Efficacy Evaluation Test of DNCB-Induced Atopic Dermatitis in Balb/c Mice Model 1.1 Test Method 1.1.1 Grouping 60 healthy male SPF Balb/c mice, each of which the body weight was 19-21 g, were randomly divided into 6 groups by body weight. There were 10 mice in each group.

TABLE 1

Grouped Table

| Groups | Administration Dose mg/mouse | Administration Concentration mg/mL | Applying Volume on Two Sides of Ear μL | Solvent | DNCB Concentration mg/mL | Applying Volume of Inducer on Two Sides of Ear μL | Number of Animals n | Administration Frequencies and Administration Days |
|---|---|---|---|---|---|---|---|---|
| Blank Control Group | — | — | 20 | Acetone | — | — | 10 | BID × 10 |
| Model Control Group | — | — | 20 | | First time: 10 Second time to the end of the test: 4 | 20 | 10 | BID × 10 |
| Example 10 | 1 | 50 | 20 | | | | 10 | BID × 10 |
| Example 1 | 1 | 50 | 20 | | | | 10 | BID × 10 |
| Example 3 | 1 | 50 | 20 | | | | 10 | BID × 10 |
| Example 11 | 1 | 50 | 20 | | | | 10 | BID × 10 |

Note:
DNCB is dinitrochlorobenzene;
BID means administration twice per day.

1.1.2 Shave

Before the test, the hair around the right ear of the mouse was removed to reduce the interference in the drug adhesion to the hair.

1.1.3 Modeling and Administration

The start of the test was recorded as Day 1. The administration and induction regimens of each group were shown in FIG. 1. The specific time for measuring ear thickness was slightly adjusted based on FIG. 1. After the end of the 18th day of the test, blood was taken from each animal to detect the concentration of immunoglobulin (IgE) in the serum (in accordance with the kit instructions). Both ears of the animal were cut off. Ear pieces were cut by an 8 mm punch at the fixed position of the ears and weighed. Differences in the swelling degrees of two ears were calculated.

1.2 Evaluation Indexes and Statistical Method

The changes in mouse ear thickness and the ear weights of the same area and the IgE concentrations in the serum among different groups on the 18th day were analyzed and compared statistically with One-Way Anova in SPSS 17, respectively. The G test method was used to delete outliers. $p<0.05$ indicated there were statistical differences.

Ear swelling degree (mg)=right ear weight (mg)−left ear weight (mg);

Ear thickness change (mm)=right ear thickness (mm)−left ear thickness (mm);

Inhibitory rate of ear swelling degree (%)=1−(ear swelling degree of drug administration group−ear swelling degree of blank control group)/(ear swelling degree of model control group−ear swelling degree of blank control group)×100%;

Inhibitory rate of ear thickness change (%)=1−(ear thickness change of drug administration group−ear thickness change of blank control group)/(ear thickness change of model control group−ear thickness change of blank control group)×100%;

Inhibitory rate of IgE (%)=1−(IgE concentration in administration group−IgE concentration in blank control group)/(IgE concentration in model control group−IgE concentration in blank control group)×100%.

1.3 Test Results

TABLE 2

Weight Changes of Animals in Each Group, Unit: g, Mean ± S.D.

| Groups | Day 1 | Day 10 | Day 17 | Day 18 |
|---|---|---|---|---|
| Blank Control Group | 21.1 ± 0.9 | 22.3 ± 0.9 | 23.0 ± 0.7 | 23.9 ± 0.7 |
| Model control group | 20.8 ± 0.7 | 21.9 ± 1.1 | 22.1 ± 1.1 | 22.3 ± 1.3 |
| Example 10 | 20.6 ± 0.8 | 22.3 ± 1.1 | 21.8 ± 1.3 | 22.4 ± 1.3 |
| Example 1 | 21.0 ± 0.8 | 22.4 ± 0.8 | 21.9 ± 1.1 | 22.0 ± 1.3 |
| Example 3 | 20.6 ± 0.8 | 22.3 ± 1.4 | 22.1 ± 1.8 | 21.7 ± 1.8 |
| Example 11 | 20.3 ± 1.3 | 21.6 ± 1.1 | 21.2 ± 1.2 | 21.1 ± 1.3 |

TABLE 3

Ear Thickness Change in Each Group, Unit: mm, Mean ± S.D.

| Groups | Day 1 | Day 10 | Day 17 | Day 18 |
|---|---|---|---|---|
| Blank Control Group | 0.21 ± 0.01 | 0.23 ± 0.02 | 0.22 ± 0.02 | 0.21 ± 0.01 |
| Model control group | 0.21 ± 0.01 | 0.50 ± 0.22 | 0.74 ± 0.22 | 0.77 ± 0.12 |
| Example 10 | 0.21 ± 0.01 | 0.35 ± 0.07 | 0.46 ± 0.10 | 0.44 ± 0.07 |
| Example 1 | 0.22 ± 0.02 | 0.47 ± 0.02 | 0.60 ± 0.08 | 0.64 ± 0.07 |
| Example 3 | 0.21 ± 0.01 | 0.38 ± 0.10 | 0.58 ± 0.09 | 0.58 ± 0.10 |
| Example 11 | 0.22 ± 0.01 | 0.33 ± 0.09 | 0.35 ± 0.04 | 0.48 ± 0.06 |

TABLE 4

Comparison of Animal Ear Indexes of Each Group

| Groups | Ear Thickness mm | Inhibitory Rate of Ear Thickness % | Ear Swelling Degree | Inhibitory Rate of Ear Swelling Degree % | IgE Concentration ng/mL | Inhibitory Rate of IgE Concentration % |
|---|---|---|---|---|---|---|
| Blank control group | 0.21 ± 0.01 | — | −0.1 ± 1.4 | — | 1359.6 ± 573.3 | — |
| Model control group | 0.77 ± 0.12 *** | — | 25.3 ± 5.2 *** | — | 8442.3 ± 5395.1 * | — |
| Example 10 | 0.44 ± 0.07 ### | 58.8 | 13.7 ± 2.9 ## | 45.7 | 4366.7 ± 1933.9 | 57.5 |
| Example 1 | 0.64 ± 0.07 | 22.5 | 19.9 ± 5.1 | 21.3 | 6631.4 ± 1431.1 | 25.6 |
| Example 3 | 0.58 ± 0.10 # | 34.0 | 15.7 ± 4.5 # | 37.8 | 6526.5 ± 2171.9 | 27.0 |
| Example 11 | 0.48 ± 0.06 ### | 51.5 | 12.8 ± 4.9 # | 49.2 | 5854.5 ± 2631.7 | 36.5 |

Note:
Compared with the blank control group,
* $P < 0.05$,
*** $P < 0.001$;
Compared with the model control group,
$P < 0.05$,
$P < 0.01$,
$P < 0.001$;

Biological Example 2

Efficacy Evaluation Test of DNCB-Induced Atopic Dermatitis in Balb/c Mice Model 2.1 Test Method
2.1.1 Grouping
70 healthy male SPF Balb/c mice, each of which the weight was 19-21 g, were randomly divided into 7 groups by body weight. There were 10 mice in each group.

2.1.2 Shave
Before the test, the hair around the right ear of the mouse was removed to reduce the interference in the drug adhesion to the hair.

Figure 2:
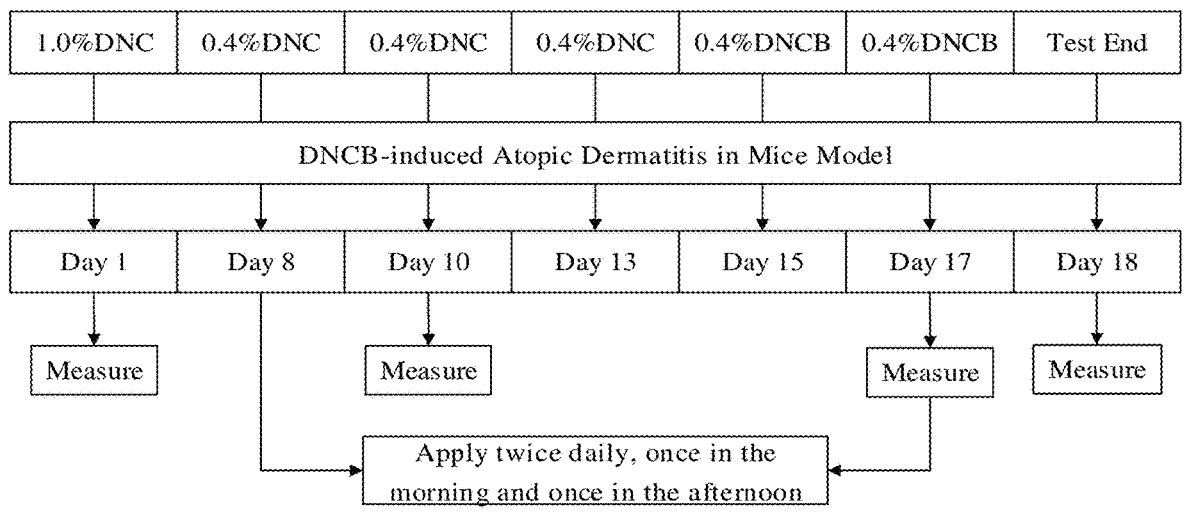
FIG. 2 shows a method of induction on and administration to model animals in Biological Example 2 of the present disclosure.

2.1.3 Modeling and Administration
The start of the test was recorded as Day 1. The administration and induction regimens of each group were shown in FIG. 2. After the end of the 18th day of the test, blood was taken from each animal to detect the concentration of immunoglobulin (IgE) in the serum (in accordance with the

TABLE 5

Grouped Table

| Group | Administration Dose mg/mouse | Administration Concentration mg/mL | Applying Volume on Two Sides of Ear μL | Solvent | DNCB Concentration mg/mL | Applying Volume of Inducer on Two Sides of Ear μL | Number of Animals n | Administration Frequencies and Administration Days |
|---|---|---|---|---|---|---|---|---|
| Blank Control Group | — | — | 20 | Acetone | — | — | 10 | BID × 10 |
| Model control group | — | — | 20 | | First time: 10 | 20 | 10 | BID × 10 |
| Example 46 | 1 | 50 | 20 | | Second time to the end of the test: 4 | | 10 | BID × 10 |
| Example 51 | 1 | 50 | 20 | | | | 10 | BID × 10 |
| Example 52 | 1 | 50 | 20 | | | | 10 | BID × 10 |
| Example 6 | 1 | 50 | 20 | | | | 10 | BID × 10 |
| Example 54 | 1 | 50 | 20 | | | | 10 | BID × 10 | kit instructions). Both ears of the animal were cut off. Ear pieces were cut by an 8 mm punch at the fixed position of the ears and weighed. Differences in the swelling degrees of two ears were calculated.

2.2 Evaluation Indexes and Statistical Method

The IgE concentrations in the serum of different groups on the 18th day were analyzed and compared statistically with One-Way Anova in SPSS 17, respectively. The G test method was used to delete outliers. $p<0.05$ indicated there were statistical differences.

Ear swelling degree (mg)=right ear weight (mg)−left ear weight (mg);

Inhibitory rate of ear swelling degree (%)=1−(ear swelling degree of drug administration group−ear swelling degree of blank control group)/(ear swelling degree of model control group−ear swelling degree of blank control group)×100%;

Inhibitory rate of IgE (%)=1−(IgE concentration in administration group−IgE concentration in blank control group)/(IgE concentration in model control group−IgE concentration in blank control group)×100%.

2.3 Experimental Results

TABLE 6

Weight Changes of Animals in Each Group

| Groups | Time | | | |
|---|---|---|---|---|
| | Day 1 | Day 10 | Day 17 | Day 18 |
| Blank Control Group | 22.0 ± 0.8 | 22.7 ± 1.0 | 24.3 ± 1.4 | 24.5 ± 1.4 |
| Model control group | 21.8 ± 0.4 | 22.4 ± 0.7 | 23.0 ± 0.9 | 22.8 ± 0.8 |
| Example 46 | 21.6 ± 0.7 | 22.6 ± 0.6 | 23.0 ± 0.7 | 23.1 ± 0.7 |
| Example 51 | 21.8 ± 0.7 | 22.8 ± 1.2 | 23.1 ± 1.1 | 22.9 ± 1.3 |
| Example 52 | 21.8 ± 0.5 | 22.6 ± 0.9 | 24.3 ± 5.6 | 24.2 ± 6.0 |
| Example 6 | 21.4 ± 0.7 | 22.8 ± 1.4 | 23.3 ± 1.4 | 22.7 ± 1.5 |
| Example 54 | 21.6 ± 0.6 | 22.6 ± 0.8 | 23.3 ± 1.2 | 23.1 ± 1.2 |

Unit: g,
Mean ± S.D.

TABLE 7

Comparison of Animal Ear Indexes of Each Group

| Groups/ Indexes | Ear Swelling Degree mg | Inhibitory Rate of Ear Swelling % | IgE Concentration ng/mL | Inhibitory Rate of IgE Concentration % |
|---|---|---|---|---|
| Blank Control Group | 1.0 ± 1.2 | — | 740.7 ± 349.6 | — |
| Model control group | 28.6 ± 8.1*** | — | 8376.3 ± 3411.6** | — |
| Example 46 | 18.6 ± 3.9# | 36.2 | 4429.8 ± 1713.9 | 51.7 |
| Example 51 | 21.7 ± 4.5 | 25.0 | 6599.5 ± 2996.0 | 23.3 |
| Example 52 | 12.0 ± 5.4 | 60.1 | 4141.5 ± 2315.0 | 55.5 |
| Example 6 | 17.1 ± 4.0## | 41.7 | 5871.9 ± 2973.8 | 32.8 |
| Example 54 | 16.7 ± 3.0# | 43.1 | 4873.7 ± 1356.2 | 45.9 |

Note:
Compared with the blank control group, $P < 0.01$, *$P < 0.001$;
Compared with the model control group, #$P < 0.05$, ##$P < 0.01$.

Biological Example 3

Efficacy Evaluation Test of DNCB-Induced Atopic Dermatitis in Balb/c Mice Model 3.1 Test Method 3.1.1 Grouping 30 healthy male SPF Balb/c mice, each of which the weight was 19-21 g, were randomly divided into 3 groups by body weight. There were 10 mice in each group.

TABLE 8

Grouped Table

| Groups | Administration Dose mg/mouse | Administration Concentration mg/mL | Applying Volume on Two Sides of Ear μL | Solvent | DNCB Concentration mg/mL | Applying Volume of Inducer on Two Sides of Ear μL | Number of Animals n | Administration Frequencies and Administration Days |
|---|---|---|---|---|---|---|---|---|
| Blank Control Group | — | — | 20 | Acetone | — | — | 10 | BID × 11 |
| Model control group | — | — | 20 | | First time: 10 | 20 | 10 | BID × 11 |
| Example 10 | 0.1 | 5 | 20 | | Second time to the end of the experiment: 4 | | 10 | BID × 11 |

3.1.2 Shave

Before the test, the hair around the right ear of the mouse was removed to reduce the interference in the drug adhesion to the hair.

3.1.3 Modeling and Administration

Figure 3:
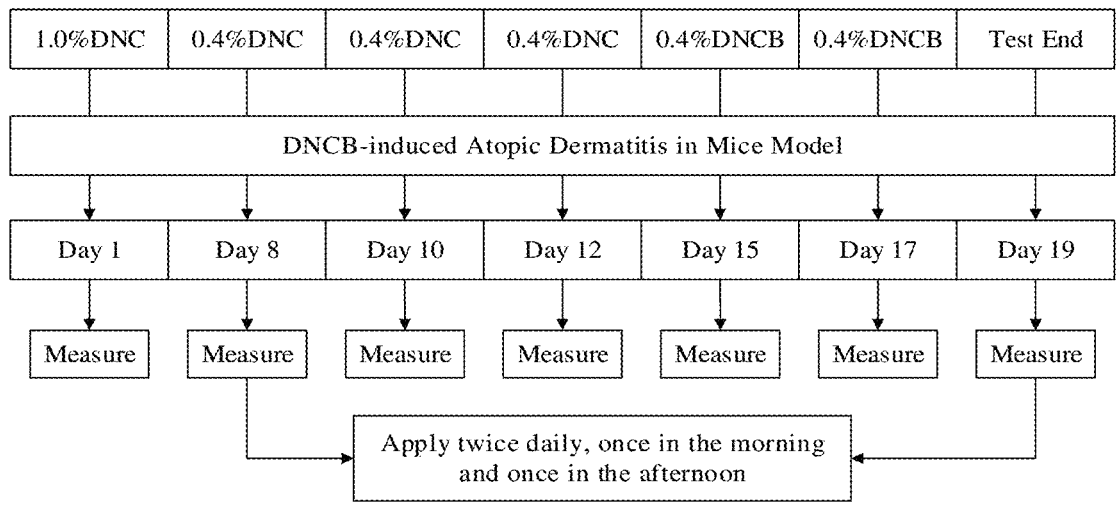
FIG. 3 shows a method of induction on and administration to model animals in Biological Example 3 of the present disclosure.

The start of the test was recorded as Day 1. The administration and induction regimens of each group were shown in FIG. 3. The specific time for measuring ear thickness and body weight was slightly adjusted based on FIG. 3. After the end of the Day 19 of the test, blood was taken from each animal to detect the concentration of immunoglobulin (IgE) in the serum (in accordance with the kit instructions). Both ears of the animal were cut off. Ear pieces were cut by an 8 mm punch at the fixed position of the ears and weighed. Differences in the swelling degree of two ears were calculated.

3.2 Evaluation Indexes and Statistical Method

The changes in mouse ear thickness and the ear weights of the same area and the IgE concentrations in the serum of different groups on the 19th day were analyzed and compared statistically with One-Way Anova in SPSS 17, respectively. The G test method was used to delete outliers. $p<0.05$ indicated there were statistical differences.

Ear swelling degree (mg)=right ear weight (mg)−left ear weight (mg);

Ear thickness change (mm)=right ear thickness (mm)−left ear thickness (mm);

Inhibitory rate of ear swelling degree (%)=1−(ear swelling degree of drug administration group−ear swelling degree of blank control group)/(ear swelling degree of model control group−ear swelling degree of blank control group)×100%;

Inhibitory rate of ear thickness change (%)=1−(ear thickness change of drug administration group−ear thickness change of blank control group)/(ear thickness change of model control group−ear thickness change of blank control group)×100%;

Inhibitory rate of IgE (%)=1−(IgE concentration in administration group−IgE concentration in blank control group)/(IgE concentration in model control group−IgE concentration in blank control group)×100%.

3.3 Test Results

TABLE 9

Weight Changes of Animals in Each Group, Unit: g, Mean ± S.D.

| Groups | Day 1 | Day 8 | Day 12 | Day 14 | Day 16 | Day 19 |
| --- | --- | --- | --- | --- | --- | --- |
| Blank Control Group | 20.4 ± 0.7 | 21.5 ± 1.0 | 22.0 ± 1.2 | 22.1 ± 1.3 | 22.3 ± 1.3 | 22.8 ± 1.3 |
| Model control group | 20.2 ± 0.7 | 21.7 ± 0.7 | 22.1 ± 0.8 | 22.0 ± 0.8 | 21.9 ± 0.7 | 22.7 ± 0.6 |
| Example 10 | 20.5 ± 0.7 | 21.8 ± 0.9 | 21.9 ± 0.8 | 22.2 ± 0.8 | 22.0 ± 0.8 | 22.3 ± 0.9 |

TABLE 10

Ear Thickness Change in Each Group, Unit: mm, Mean ± S.D.

| Groups | Day 1 | Day 10 | Day 17 | Day 19 |
| --- | --- | --- | --- | --- |
| Blank Control Group | 0.24 ± 0.01 | 0.25 ± 0.01 | 0.25 ± 0.01 | 0.27 ± 0.02 |
| Model control group | 0.26 ± 0.01 | 0.54 ± 0.12 | 0.76 ± 0.16 | 0.77 ± 0.14 |
| Example 10 | 0.26 ± 0.01 | 0.52 ± 0.11 | 0.65 ± 0.09 | 0.63 ± 0.05 |

TABLE 11

Comparison of Animal Ear Indexes in Each Group

| Groups/Indexes | Ear Thickness mm | Inhibitory Rate of Ear Thickness % | Ear Swelling Degree mg | Inhibitory Rate of Ear Swelling % | IgE Concentration ng/mL | Inhibitory Rate of IgE Concentration % |
| --- | --- | --- | --- | --- | --- | --- |
| Blank Control Group | 0.27 ± 0.02 | — | −0.3 ± 0.5 | — | 1288.6 ± 881.6 | — |
| Model control group | 0.77 ± 0.14 *** | — | 12.7 ± 4.1 *** | — | 7339 ± 3261.8* | — |
| Example 10 | 0.63 ± 0.05 | 27.1 | 7.7 ± 1.8 | 38.5 | 5543.4 ± 2139.3 | 29.7 |

Note:
Compared with the blank control group,
** $P < 0.01$,
*** $P < 0.001$.

Biological Example 4

Tests of Inhibition of Phorbol Ester (TPA)-Induced Ear Swelling in Mice 4.1 Test Method 4.1.1 Grouping 40 male ICR mice were selected and divided into 5 groups. There were 8 mice in each group.

TABLE 12

Grouping Modeling Information Table

| Groups | Inducer Concentration (µg/mL) | Inducer Volume (µL) | Solvent | Induction Route | Animal Number (n) |
| --- | --- | --- | --- | --- | --- |
| Blank Control Group | — | 20 | Mixed Solution of Acetone and DMSO | Topically Applying | 8 |
| Model control group | 125 | 20 | Mixed Solution of Acetone and DMSO | Topically Applying | 8 |
| Example 1 | 125 | 20 | Mixed Solution of Acetone and DMSO | Topically Applying | 8 |

TABLE 12-continued

Grouping Modeling Information Table

| Groups | Inducer Concentration (μg/mL) | Inducer Volume (μL) | Solvent | Induction Route | Animal Number (n) |
|---|---|---|---|---|---|
| Example 10 | 125 | 20 | Mixed Solution of Acetone and DMSO | Topically Applying | 8 |
| Example 9 | 125 | 20 | Mixed Solution of Acetone and DMSO | Topically Applying | 8 |

Note:
a. Process for preparing 125 μg/mL TPA: 40 μL of 2 mg/mL TPA mother solution (dissolved in DMSO) and 600 μL of acetone were mixed homogeneously. It was prepared when needed to use.
b. The mixing ratio of acetone and DMSO was 15: 1 (v/v).

4.1.2 Shave

Before the test, the animals were grouped and the hair around the right ear of the mice was removed.

4.1.3 Modeling and Administration

20 μL of respective drug was applied to the animals in each test group (a blank solvent was applied to the model control group). Modeling and induction were carried out after 1 h 10 min. Except for the blank group, 20 μL of TPA at a concentration of 125 μg/mL were applied to the right ears of the animals for induction. After induction for 10 minutes, 20 μL of respective drug was applied to the right ears of the animals in each test group (a blank solvent was applied to the model control group).

TABLE 13

Grouping and Administration Information Table

| Groups | Administration Concentration (mg/mL) | Administration Volume (μL) | Solvent | Administration Frequency | Animal Number (n) |
|---|---|---|---|---|---|
| Blank Control Group | — | 40 | Acetone | 2 | 8 |
| Model control group | — | 40 | Acetone | 2 | 8 |
| Example 1 | 30 | 40 | Acetone | 2 | 8 |
| Example 10 | 30 | 40 | Acetone | 2 | 8 |
| Example 9 | 30 | 40 | Acetone | 2 | 8 |

Note:
The administration volume of 40 μL refers to a total of 40 μL in 2 administrations.

4.1.4 Observation of Results

After modeling for 5 hours, ear pieces of both sides on the same location of animals in each group were taken with a punch and weighed to calculate the ear swelling degree, ear swelling rate and inhibitory rate.

4.2 Evaluation Indexes and Statistical Method

The ear swelling degree and ear swelling rate after modeling and administration for 5 hours were analyzed and tested with One-Way ANOVA multiple-group test index in SPSS17.0. $P<0.05$ indicated there were statistical differences.

Ear swelling degree (mg)=right ear weight (mg)−left ear weight (mg);

Ear swelling rate (%)=(right ear weight−left ear weight)/left ear weight×100%;

Inhibitory rate of ear swelling degree (%)=1−(ear swelling degree of drug administration group−ear swelling degree of blank control group)/(ear swelling degree of model control group−ear swelling degree of blank control group)×100%.

4.3 Test Results

TABLE 14

Inhibitory Rate and Other Indexes of Mice in Each Group

| Groups/Indexes | Inhibitory Rate of Ear Swelling Degree % |
|---|---|
| Blank Control Group | — |
| Model control group | — |
| Example 10 | 71.7 |
| Example 9 | 54.5 |
| Example 1 | 60.1 |

Biological Example 5

Test of Inhibition of Phorbol Ester (TPA)-Induced Ear Swelling in Mice 5.1 Test Method 5.1.1 Grouping 72 male ICR mice were selected and divided into 9 groups. There were 8 mice in each group.

TABLE 15

Grouping and Modeling Information Table

| Groups | Inducer Concentration (μg/mL) | Inducer Volume (μL) | Solvent | Route | Animals Numbers (n) |
|---|---|---|---|---|---|
| Blank Control Group | — | 20 | Mixed Solution of Acetone and DMSO | Topically Applying | 8 |
| Model control group | 125 | 20 | Mixed Solution of Acetone and DMSO | Topically Applying | 8 |
| Example 6 | 125 | 20 | Mixed Solution of Acetone and DMSO | Topically Applying | 8 |
| Example 3 | 125 | 20 | Mixed Solution of Acetone and DMSO | Topically Applying | 8 |
| Example 4 | 125 | 20 | Mixed Solution of Acetone and DMSO | Topically Applying | 8 |
| Example 12 | 125 | 20 | Mixed Solution of Acetone and DMSO | Topically Applying | 8 |
| Example 24 | 125 | 20 | Mixed Solution of Acetone and DMSO | Topically Applying | 8 |
| Example 25 | 125 | 20 | Mixed Solution of Acetone and DMSO | Topically Applying | 8 |
| Example 11 | 125 | 20 | Mixed Solution of Acetone and DMSO | Topically Applying | 8 |

Note:
a. Process for preparing 125 μg/mL TPA: 40 μL of 2 mg/mL TPA mother solution (dissolved in DMSO) and 600 μL of acetone were mixed homogeneously. It was prepared when needed to use.
b. The mixing ratio of acetone and DMSO was 15: 1 (v/v).

5.1.2 Shave

Before the test, the animals were grouped and the hair around the right ear of the mice was removed.

5.1.3 Modeling and Administration

20 μL of respective drug was applied to the animals in each test group (a blank solvent was applied to the model control group). Modeling and induction were carried out after 1 h 10 min. Except for the blank group, 20 μL of TPA at a concentration of 125 μg/mL were applied to the right ears of the animals for induction. After induction for 10 minutes, 20 μL of respective drug were applied to the right ears of the animals in each test group (a blank solvent was applied to the model control group).

TABLE 16

Grouping and Administration Information of Different Groups

| Groups | Administration Concentration (mg/mL) | Administration Volume (μL) | Administration Dose (mg/mouse) | Solvent | Administration Frequency (n) | Animal Number |
|---|---|---|---|---|---|---|
| Blank Control Group | — | 40 | — | Acetone | 2 | 8 |
| Model control group | — | 40 | 2 | Acetone | 2 | 8 |
| Example 6 | 50 | 40 | 2 | Acetone | 2 | 8 |
| Example 3 | 50 | 40 | 2 | Acetone | 2 | 8 |
| Example 4 | 50 | 40 | 2 | Acetone | 2 | 8 |
| Example 12 | 50 | 40 | 2 | Acetone | 2 | 8 |
| Example 24 | 50 | 40 | 2 | Acetone | 2 | 8 |
| Example 25 | 50 | 40 | 2 | Acetone | 2 | 8 |
| Example 11 | 50 | 40 | 2 | Acetone | 2 | 8 |

Note:
The administration volume of 40 μL refers to a total of 40 μL in 2 administrations.

5.1.4 Observation of Results

After modeling for 5 hours, ear pieces of both sides on the same location of animals in each group were taken with a punch and weighed to calculate the ear swelling degree, ear swelling rate and inhibitory rate.

5.2 Evaluation Indexes and Statistical Method

The ear swelling degree and ear swelling rate after modeling and administration for 5 hours were analyzed and tested with One-Way ANOVA multiple-group test index in SPSS17.0. $P<0.05$ indicated there were statistical differences.

Ear swelling degree (mg)=right ear weight (mg)−left ear weight (mg);

Ear swelling rate (%)=(right ear weight−left ear weight)/left ear weight×100%;

Inhibitory rate of ear swelling degree (%)=1−(ear swelling degree of drug administration group−ear swelling degree of blank control group)/(ear swelling degree of model control group−ear swelling degree of blank control group)×100%.

5.3 Test Results

TABLE 17

Inhibitory Rate and Other Indexes of Mice in Each Group:

| Groups | Ear Swelling Degree mg | Ear Swelling Rate % | Inhibitory Rate of Ear Swelling Degree % |
|---|---|---|---|
| Example 6 | 5.1 ± 1.6### | 36.4 ± 11.9### | 87.3 |
| Example 3 | 6.0 ± 2.5### | 42.1 ± 19.3### | 83.7 |
| Example 4 | 4.8 ± 2.1### | 34.3 ± 18.2### | 88.8 |

TABLE 17-continued

Inhibitory Rate and Other Indexes of Mice in Each Group:

| Groups | Ear Swelling Degree mg | Ear Swelling Rate % | Inhibitory Rate of Ear Swelling Degree % |
|---|---|---|---|
| Example 12 | 5.8 ± 2.3### | 39.6 ± 14.0### | 84.8 |
| Example 24 | 5.9 ± 1.7### | 43.0 ± 11.8### | 84.2 |
| Example 25 | 8.5 ± 2.7### | 59.1 ± 17.5### | 73.6 |
| Example 11 | 6.5 ± 5.0### | 46.3 ± 35.7### | 81.7 |
| Model control group | 26.6 ± 3.9*** | 197.5 ± 30.0*** | — |
| Blank control group | 2.0 ± 1.5 | 14.7 ± 12.2 | — |

Note:
Compared with the blank control group, ***$P < 0.001$;
Compared with the model control group, ###$P < 0.001$.

Biological Example 6

Test of Inhibition of Phorbol Ester (TPA)-Induced Ear Swelling in Mice 5.1 Test Method 5.1.1 Grouping 72 male ICR mice were selected and divided into 9 groups. There were 8 mice in each group.

TABLE 18

Grouping and Modeling Information Table

| Groups | Inducer Concentration (μg/mL) | Inducer Volume (μL) | Solvent | Inducing Route | Animals Number (n) |
|---|---|---|---|---|---|
| Blank Control Group | — | 20 | Mixed Solution of Acetone and DMSO | Topically Applying | 8 |
| Model Control Group | 125 | 20 | Mixed Solution of Acetone and DMSO | Topically Applying | 8 |
| Example 29 | 125 | 20 | Mixed Solution of Acetone and DMSO | Topically Applying | 8 |
| Example 30 | 125 | 20 | Mixed Solution of Acetone and DMSO | Topically Applying | 8 |
| Example 46 | 125 | 20 | Mixed Solution of Acetone and DMSO | Topically Applying | 8 |
| Example 18 | 125 | 20 | Mixed Solution of Acetone and DMSO | Topically Applying | 8 |
| Example 31 | 125 | 20 | Mixed Solution of Acetone and DMSO | Topically Applying | 8 |
| Example 20 | 125 | 20 | Mixed Solution of Acetone and DMSO | Topically Applying | 8 |
| Example 32 | 125 | 20 | Mixed Solution of Acetone and DMSO | Topically Applying | 8 |

Note:
a. Process for preparing 125 μg/mL TPA: 40 μL of 2 mg/mL TPA mother solution (dissolved in DMSO) and 600 μL of acetone were mixed. It was prepared when needed to use.
b. The mixing ratio of acetone and DMSO was 15:1 (v/v).

5.1.2 Shave

Before the test, the animals were grouped and the hair around the right ear of the mice was removed.

5.1.3 Modeling and Administration

20 μL of respective drug was applied to the animals in each test group (a blank solvent was applied to the model control group). Modeling and induction were carried out after 1 h 10 min. Except for the blank group, 20 μL of TPA at a concentration of 125 μg/mL were applied to the right ears of the animals for induction. After induction for 10 minutes, 20 μL of respective drug were applied to the right ears of the animals in each test group (a blank solvent was applied to the model control group).

TABLE 19

Grouping and Administration Information of Different Groups

| Groups | Administration Concentration (mg/mL) | Administration Volume (μL) | Administration Dose (mg/mouse) | Solvent | Administration Frequency | Animal Number (n) |
|---|---|---|---|---|---|---|
| Blank Control Group | — | 40 | — | Acetone | 2 | 8 |
| Model Control Group | — | 40 | 2 | Acetone | 2 | 8 |
| Example 29 | 50 | 40 | 2 | Acetone | 2 | 8 |
| Example 30 | 50 | 40 | 2 | Acetone | 2 | 8 |
| Example 46 | 50 | 40 | 2 | Acetone | 2 | 8 |
| Example 18 | 50 | 40 | 2 | Acetone | 2 | 8 |
| Example 31 | 50 | 40 | 2 | Acetone | 2 | 8 |
| Example 20 | 50 | 40 | 2 | Acetone | 2 | 8 |
| Example 32 | 50 | 40 | 2 | Acetone | 2 | 8 |

Note:
The administration volume of 40 μL refers to a total of 40 μL in 2 administrations.

5.1.4 Observation of Results

After modeling for 5 hours, ear pieces of both sides at the same location of animals in each group were taken with a punch and weighed to calculate the ear swelling degree, ear swelling rate and inhibitory rate.

5.2 Evaluation Indexes and Statistical Method

The ear swelling degree and ear swelling rate after modeling and administration for 5 hours were analyzed and tested with One-Way ANOVA multiple-group test index in SPSS17.0. $P<0.05$ indicated that there were statistical differences.

Ear swelling degree (mg)=right ear weight (mg)−left ear weight (mg);

Ear swelling rate (%)=(right ear weight−left ear weight)/left ear weight×100%;

Inhibitory rate of ear swelling degree (%)=1−(swelling degree of drug administration group−swelling degree of blank control group)/(swelling degree of model control group−swelling degree of blank control group)×100%.

5.3 Test Results

TABLE 20

Inhibitory Rate and Other Indexes of Mice in Each Group:

| Groups | Ear Swelling Degree mg | Ear Swelling Rate % | Inhibitory Rate of Ear Swelling Degree % |
|---|---|---|---|
| Example 29 | 6.5 ± 4.6### | 46.8 ± 33.9### | 81.5 |
| Example 46 | 6.4 ± 5.3### | 44.9 ± 35.5### | 82.0 |
| Example 30 | 12.0 ± 3.5### | 85.0 ± 27.4### | 60.8 |
| Example 18 | 4.8 ± 1.9### | 33.9 ± 14.0### | 88.1 |
| Example 31 | 4.9 ± 2.0### | 34.3 ± 14.9### | 87.6 |
| Example 20 | 8.8 ± 2.8### | 63.9 ± 19.3### | 73.0 |
| Example 32 | 13.4 ± 4.0### | 93.3 ± 28.1### | 55.6 |
| Model Control Group | 28.1 ± 4.2*** | 208.9 ± 44.2*** | — |
| Blank Control Group | 1.6 ± 1.8 | 12.0 ± 13.4 | — |

Note:
Compared with the blank control group, ***$P < 0.001$;
Compared with the model control group, ###$P < 0.001$.

Biological Example 7

Subacute Toxicity Test of Continuous Gavage in Mice for 22 Days 7.1 Test Method
7.1.1 Grouping 96 healthy SD rats of SPF grade were randomly divided into 8 groups according to the gender segment, in which 48 mice were male and 48 mice were female. There were 6 mice per gender per group, which were solvent control group and administration groups of respective compounds. There were 12 mice in each group, in which 6 mice were male and 6 mice were female.

TABLE 21

Grouped Table

| Drug | Gender | Administration Dose (mg/Kg) | Administration Volume (mL/Kg) | Drug Concentration (mg/mL) |
|---|---|---|---|---|
| Solvent Control Group | ♂ | 300 | 10 | 30 |
| | ♀ | 300 | 10 | 30 |
| Example 10 | ♂ | 300 | 10 | 30 |
| | ♀ | 300 | 10 | 30 |
| Example 9 | ♂ | 300 | 10 | 30 |
| | ♀ | 300 | 10 | 30 |
| Example 1 | ♂ | 300 | 10 | 30 |
| | ♀ | 300 | 10 | 30 |
| Example 3 | ♂ | 300 | 10 | 30 |
| | ♀ | 300 | 10 | 30 |
| Example 4 | ♂ | 300 | 10 | 30 |
| | ♀ | 300 | 10 | 30 |
| Example 11 | ♂ | 300 | 10 | 30 |
| | ♀ | 300 | 10 | 30 |
| Example 29 | ♂ | 300 | 10 | 30 |
| | ♀ | 300 | 10 | 30 |

Note:
♂ represents male;
♀ represents female.

7.1.2 Administration

Oral administration by gavage was carried out once a day for 22 consecutive days. 300 mg/Kg of the corresponding compound were administered to each group and an equal volume of sodium carboxymethylcellulose (CMC-Na) was administered to the solvent control group. Continuous administration was carried out for 22 days. Whether the behavior and state of the rats were normal and whether there was poisoning phenomenon after administration were observed daily. The animal response was recorded. After continuous administration for 22 days, 3 animals/gender/group were sacrificed. The mice were dissected and generally observed. The organ indexes were collected. After drug withdrawal for one week, the remaining 3 animals/gender/group were sacrificed. The mice were generally observed and the organ indexes were collected.

7.1.3 Observation Indexes

Body weight, appearance, breath, behavior, reflex and defecation 7.2 Test Results
7.2.1 Clinical Observation No obvious abnormalities of the body weight, appearance, breath, behavior, reflex and defecation of the animals were observed during the test.

7.2.2 Body Weight

Figure 4:
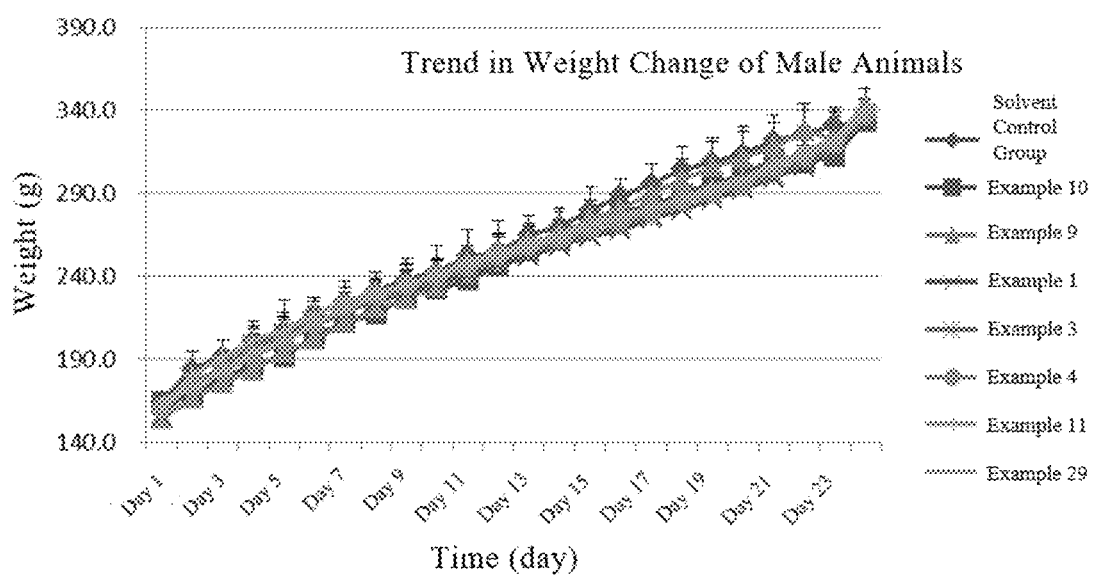
FIG. 4 shows a trend in weight change of male animals in each experimental group of Biological Example 7 of the present disclosure.
Figure 5:
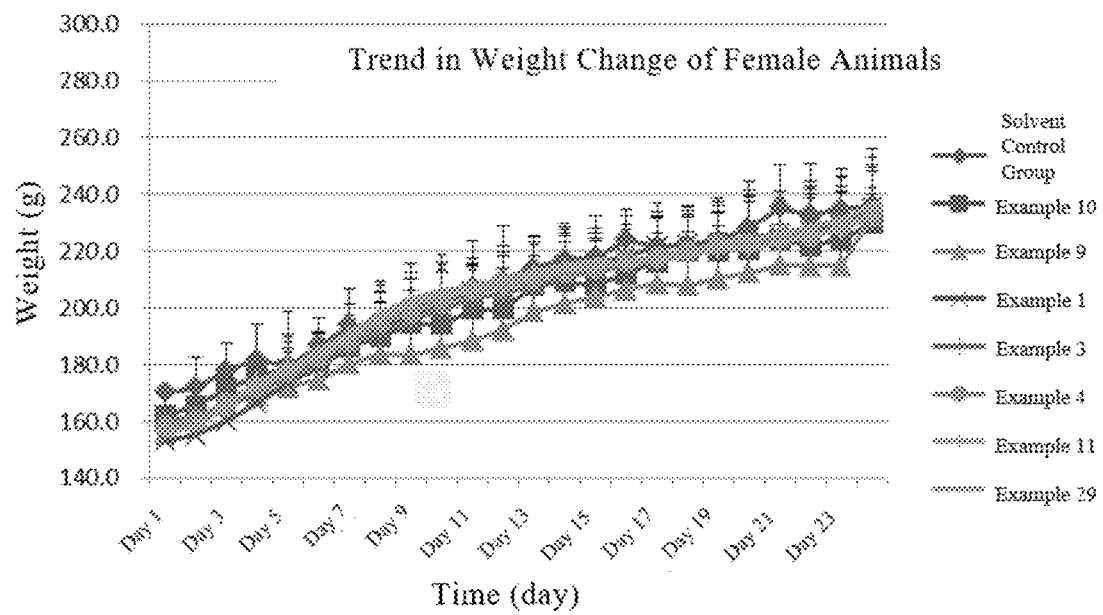
FIG. 5 shows a trend in weight change of female animals in each experimental group of Biological Example 7 of the present disclosure.

No obvious abnormality of the body weight of the animals was observed during the test. The trend of body weight change was shown in FIG. 4 and FIG. 5.

7.2.3 General Anatomical Observation

Animals in each group were dissected and generally observed at the end of the administration and at the end of the recovery period. No obvious abnormalities related to the compounds were observed in each organ.

7.2.4 Organ Indexes

No obvious abnormalities were observed in the animal organ indexes.

7.3 Test Conclusion

The above compounds were administered to SD rats by repeated gavage once a day for 22 consecutive days. No obvious drug-related toxicity was observed.

Biological Example 8

Subacute Toxicity Test of Continuous Gavage in Rats for 22 Days 8.1 Test Method
8.1.1 Grouping 84 healthy SD rats of SPF grade were randomly divided into 7 groups according to the gender segment, in which 42 mice were male and 42 mice were female. There were 6 mice per gender per group, which were solvent control group and administration groups of respective compounds. There were 12 mice in each group, in which 6 mice were male and 6 mice were female.

TABLE 22

Grouped Table

| Drug | Gender | Administration Dose (mg/Kg) | Administration Volume (mL/Kg) | Drug Concentration (mg/mL) |
|---|---|---|---|---|
| Solvent Control Group | ♂ | 300 | 10 | 30 |
| | ♀ | 300 | 10 | 30 |
| Example 6 | ♂ | 300 | 10 | 30 |
| | ♀ | 300 | 10 | 30 |
| Example 51 | ♂ | 300 | 10 | 30 |
| | ♀ | 300 | 10 | 30 |
| Example 52 | ♂ | 300 | 10 | 30 |
| | ♀ | 300 | 10 | 30 |
| Example 46 | ♂ | 300 | 10 | 30 |
| | ♀ | 300 | 10 | 30 |
| Example 53 | ♂ | 300 | 10 | 30 |
| | ♀ | 300 | 10 | 30 |
| Example 54 | ♂ | 300 | 10 | 30 |
| | ♀ | 300 | 10 | 30 |

Note:
♂ represents male;
♀ represents female.

8.1.2 Administration

Oral administration by gavage was carried out once a day for 22 consecutive days. 300 mg/Kg of the corresponding compound were administered to each administration group and an equal volume of CMC-Na was administered to the solvent control group. Continuous administration was carried out for 22 days. Whether the behavior and state of the rats were normal and whether there was poisoning phenomenon after administration were observed daily. The animal response was recorded. After continuous administration for 22 days, 3 animals/gender/group were sacrificed. The mice were dissected and generally observed. The organ indexes were collected. After drug withdrawal for one week, the remaining 3 animals/gender/group were sacrificed. The mice were generally observed and the organ indexes were collected.

8.1.3 Observation Indexes

Body weight, appearance, breath, behavior, reflex and defecation 8.2 Test Results 8.2.1 Clinical Observation No obvious abnormalities of the body weight, appearance, breath, behavior, reflex and defecation of the animals were observed during the test.

8.2.2 Body Weight

Figure 6:
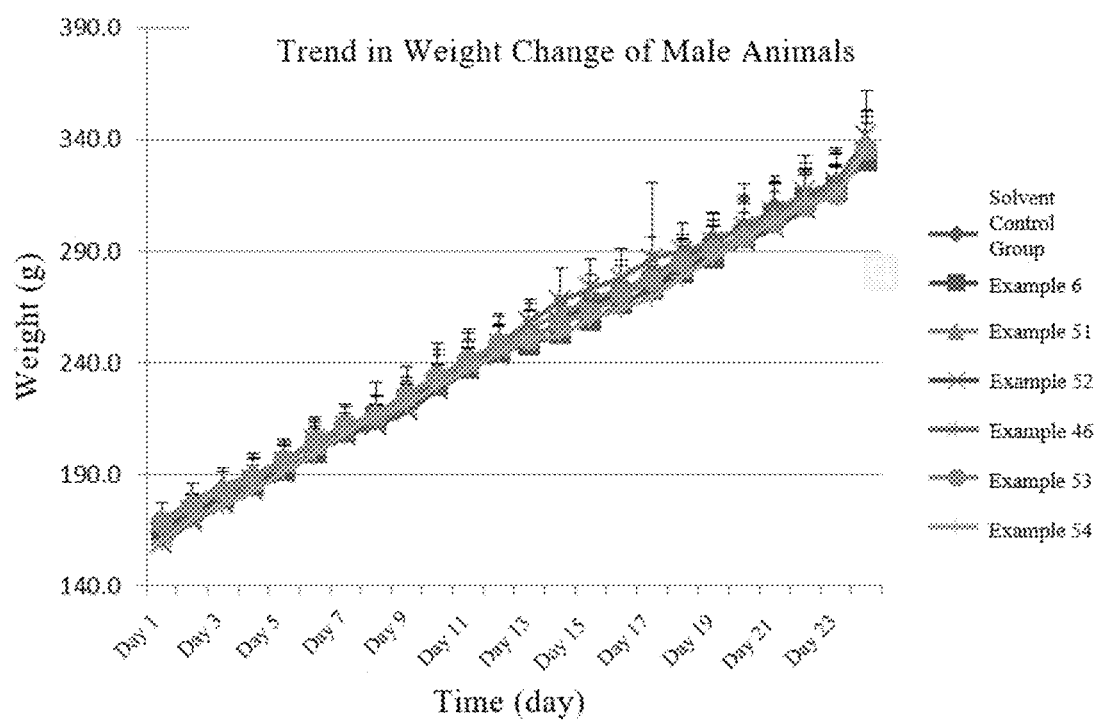
FIG. 6 shows a trend in weight change of male animals in each experimental group of Biological Example 8 of the present disclosure.
Figure 7:
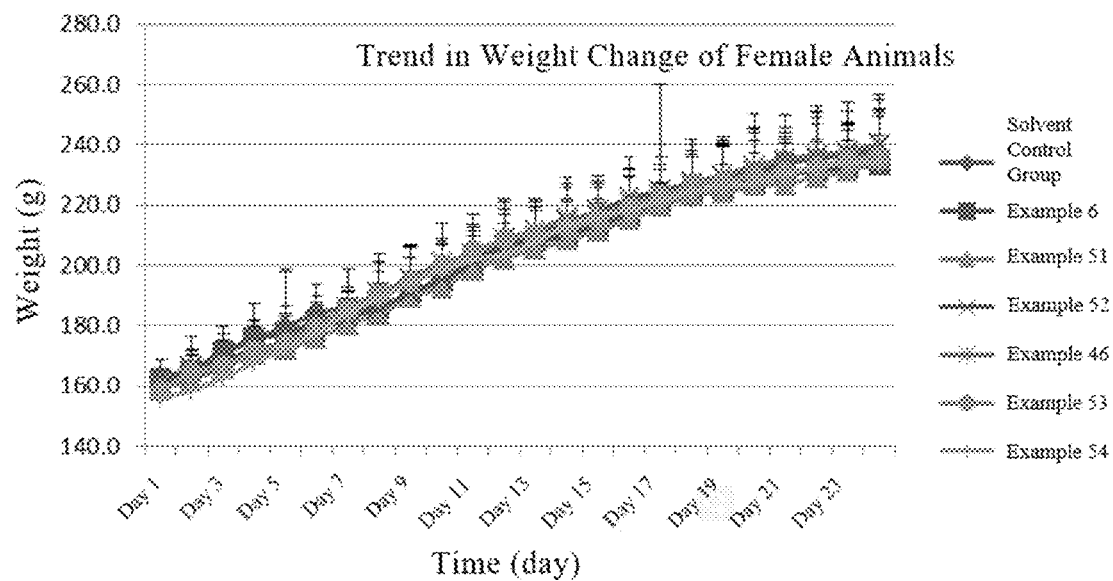
FIG. 7 shows a trend in weight change of female animals in each experimental group of Biological Example 8 of the present disclosure.

No obvious abnormality of the body weight of the animals was observed during the test. The trend of body weight change was shown in FIG. 6 and FIG. 7.

8.2.3 General Anatomical Observation

Animals in each group were dissected and generally observed at the end of the administration and at the end of the recovery period. No obvious abnormalities related to the compounds were observed in each organ.

8.2.4 Organ Indexes

No obvious abnormalities were observed in the animal organ indexes.

8.3 Test Conclusion

The above compounds were administered to SD rats by repeated gavage once a day for 22 consecutive days. No obvious drug-related toxicity was observed.

Biological Example 9

Acute Toxicity Test of Single Gavage in Mice 9.1 Test Method 9.1.1 Grouping 30 healthy ICR mice of SPF grade were randomly divided into 5 groups according to the gender segment, in which 15 mice were male and 15 mice were female. There were 3 mice/gender/group. There were 6 mice in each group, in which 3 mice were male and 3 mice were female.

TABLE 23

Grouped Table

| Groups | Administration (mg/Kg) | Concentration mg/mL | Administration Volume mL/Kg | Gender ♂/ mouse | Gender ♀/ mouse |
|---|---|---|---|---|---|
| Example 11 | 2000 | 200 | 10 | 3 | 3 |
| Example 31 | | | | 3 | 3 |
| Example 52 | | | | 3 | 3 |
| Example 54 | | | | 3 | 3 |
| Example 4 | | | | 3 | 3 |

Note:
♂ represents male;
♀ represents female.

9.1.2 Administration

Single administration by gavage was carried out. The symptoms and responses of all the animals were observed after the administration and were recorded faithfully. The test was observed continuously for 15 days. The symptoms of the animals were recorded. After the test, the tissues and organs of all the animals were weighed, observed and recorded. The specimens were kept.

9.1.3 Observation Indexes

Body weight, appearance, breath, behavior, reflex and defecation.

9.2 Test Results 9.2.1 Clinical Observation

TABLE 24

| Drug | Test Results |
|---|---|
| Example 11 | No obvious abnormalities of appearance, breath, behavior, reflex and defecation of the animals were observed during the test. Dissection and general observation were carried out at the end of the test. No obvious abnormalities related to the compounds were observed in each organ. No obvious abnormalities of organ indexes were observed. |
| Example 31 | No obvious abnormalities of appearance, breath, behavior, reflex and defecation of the animals were observed during the test. Dissection and general observation were carried out at the end of the test. No obvious abnormalities related to the compounds were observed in each organ. No obvious abnormalities of organ indexes were observed. |
| Example 52 | No obvious abnormalities in female animals were observed until the end of the test. No abnormalities of gross anatomy and organ indexes were observed. 1 male animal died in the second day of the test. It was resulted from esophageal rupture due to excessive drug viscosity. No obvious abnormalities of other animals were observed until the end of the experiment. No abnormalities of gross anatomy and organ indexes were observed. |
| Example 4 | After administration, no abnormalities of female animals were observed. The male animals had reduced activity and recovered after half an hour. No death or abnormality of animals was observed until the end of the test. |
| Example 54 | The main symptom after administration was reduced activity. No death or abnormality of animals was observed until the end of the test. |

9.2.2 Body Weight

Figure 8:
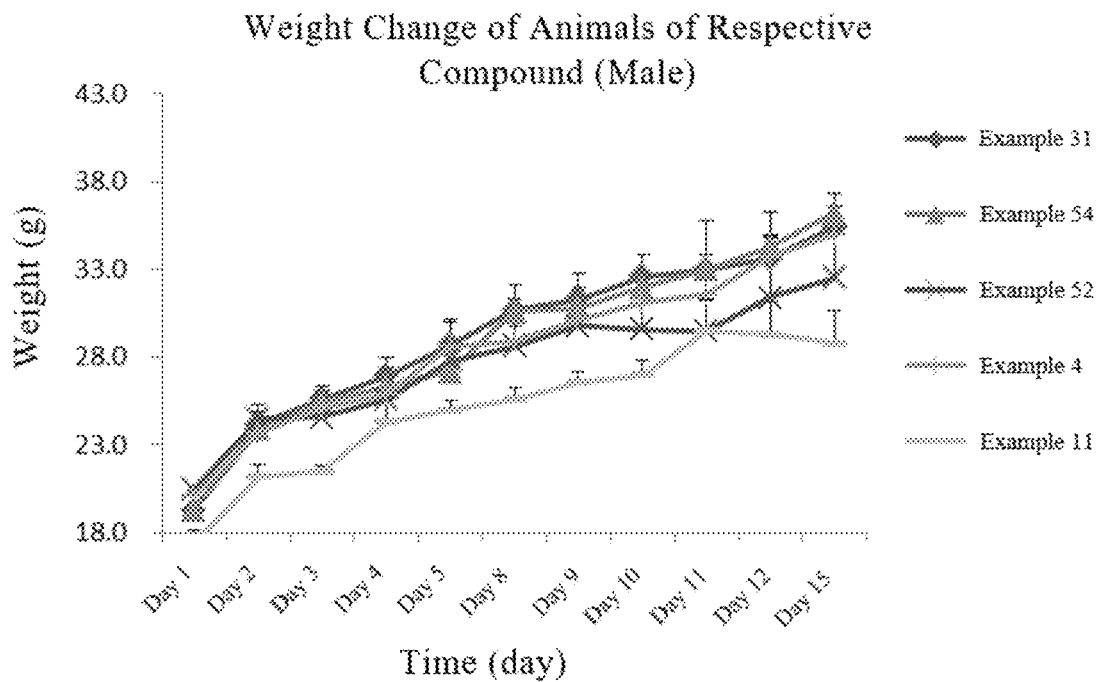
FIG. 8 shows a trend in weight change of male animals in each experimental group of Biological Example 9 of the present disclosure.
Figure 9:
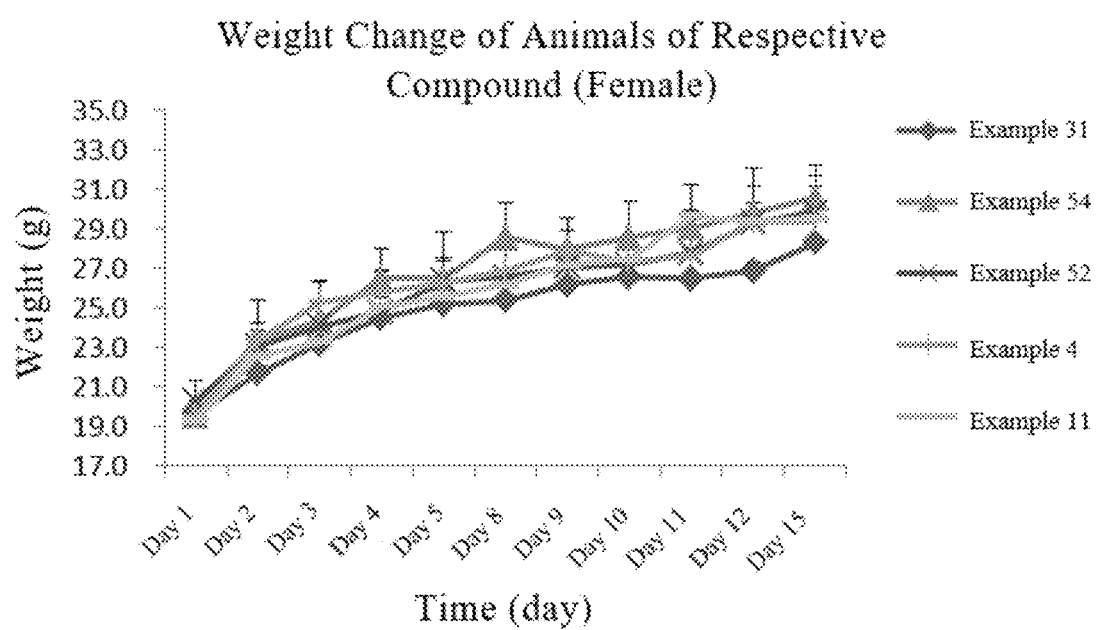
FIG. 9 shows a trend in weight change of female animals in each experimental group of Biological Example 9 of the present disclosure.

No obvious abnormalities of the body weight of the animals were observed during the test. The trend of body weight change was shown in FIG. 8 and FIG. 9.

9.2.3 General Anatomical Observation

Animals in each group were dissected and generally observed at the end of the administration and at the end of the recovery period. No obvious abnormalities related to the compounds were observed in each organ. 9.2.4 Organ Indexes No obvious abnormalities were observed in the animal organ indexes.

9.3 Test Conclusion

The above compounds were administered to ICR mice at a single administration of 2000 mg/Kg by gavage. No obvious drug-related toxicity was observed.

In the present disclosure, relational terms such as "first" and "second" are used only to distinguish one entity or operation from another entity or operation, and do not necessarily require or imply any actual relationship or order.

It can be understood from above description that although specific embodiments of the present disclosure have been described for illustrative purposes, various modifications or improvements can be made by one skilled in the art without departing from the spirit and scope of the present disclosure. Such variations or modifications should fall within the scope of the claims appended to this disclosure.

What is claimed is:

1. A compound of formula (II),

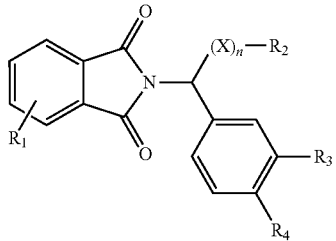

formula (II)

or a stereoisomer or pharmaceutically acceptable salt thereof, wherein
- $R_1$ represents one or more identical or different substituents selected from the group consisting of optionally substituted hydrocarbylcarbonylamino, optionally substituted hydrocarbylcarbonyloxy and optionally substituted hydrocarbyloxycarbonylamino;
- $R_2$ is hydrocarbyloxycarbonyl;
- $R_3$ is selected from the group consisting of hydrogen, halogen, hydroxy, optionally substituted hydrocarbyloxy, optionally substituted arylhydrocarbyloxy and optionally substituted cyclohydrocarbyloxy;
- $R_4$ is selected from the group consisting of hydrogen, halogen, hydroxy, optionally substituted hydrocarbyloxy, optionally substituted arylhydrocarbyloxy and optionally substituted cyclohydrocarbyloxy; and
- X is —$CR_5R_6$—, wherein
  - $R_5$ is selected from the group consisting of hydrogen, halogen, optionally substituted hydrocarbyl, optionally substituted cyclohydrocarbyl, optionally substituted aryl and optionally substituted heteroaryl, $R_6$ is selected from the group consisting of hydrogen, halogen, optionally substituted hydrocarbyl, optionally substituted cyclohydrocarbyl, optionally substituted aryl and optionally substituted heteroaryl, and n is 0, 1, 2, 3 or 4; or
  - $R_5$ and $R_6$ together with the carbon atom to which they are attached form an optionally substituted cyclohydrocarbyl, and n is 1.

2. The compound of claim 1, wherein $R_2$ is $C_1$-$C_6$alkyloxycarbonyl.

3. The compound of claim 1, wherein $R_3$ is selected from the group consisting of hydrogen, halogen, hydroxy, optionally substituted alkyloxy, optionally substituted arylalkyloxy and optionally substituted cycloalkyloxy.

4. The compound of claim 1, wherein $R_4$ is selected from the group consisting of hydrogen, halogen, hydroxy, optionally substituted alkyloxy, optionally substituted arylalkyloxy and optionally substituted cycloalkyloxy.

5. The compound of claim 1, wherein $R_1$ represents one or more identical or different substituents selected from the group consisting of optionally substituted $C_1$-$C_6$alkylcarbonylamino, optionally substituted $C_1$-$C_6$alkylcarbonyloxy and optionally substituted $C_1$-$C_6$alkyloxycarbonylamino.

6. The compound of claim 1, wherein $R_2$ is selected from the group consisting of methoxycarbonyl, ethoxycarbonyl, propoxycarbonyl, butoxycarbonyl, and isopropoxycarbonyl, $R_5$ is selected from the group consisting of hydrogen, halogen and $C_1$-$C_4$hydrocarbyl, $R_6$ is selected from the group consisting of hydrogen, halogen and $C_1$-$C_4$hydrocarbyl and n is 1 or 2.

7. The compound of claim 1, wherein $R_3$ is selected from the group consisting of hydrogen, halogen, hydroxy, optionally substituted methoxy, optionally substituted ethoxy, optionally substituted propoxy, optionally substituted isopropoxy, optionally substituted benzyloxy and optionally substituted cyclopentyloxy.

8. The compound of claim 1, wherein $R_4$ is selected from the group consisting of hydrogen, halogen, hydroxy, optionally substituted methoxy, optionally substituted ethoxy, optionally substituted propoxy, optionally substituted isopropoxy, optionally substituted benzyloxy and optionally substituted cyclopentyloxy.

9. The compound of claim 1, wherein $R_1$ represents one or more identical or different substituents selected from the group consisting of optionally substituted acetamido, optionally substituted acetoxy and optionally substituted tert-butoxycarbonylamino.

10. The compound of claim 1, wherein $R_1$ represents one or more substituents selected from the group consisting of $C_1$-$C_6$alkylcarbonylamino, $C_1$-$C_6$alkylcarbonyloxy, $C_1$-$C_6$alkyloxycarbonylamino, $C_1$-$C_6$alkylcarbonylamino substituted with amino substituted with $C_1$-$C_6$alkyl and $C_1$-$C_6$alkylcarbonylamino substituted with N-$C_1$-$C_6$alkyl.

11. The compound of claim 1, wherein $R_2$ is $C_1$-$C_6$alkyloxycarbonyl, $R_5$ is hydrogen, $R_6$ is hydrogen and n is 1.

12. The compound of claim 1, wherein $R_3$ is selected from the group consisting of hydrogen, hydroxy, halogen, $C_1$-$C_8$alkyloxy, $C_5$-$C_{12}$aryloxy and $C_5$-$C_{12}$cyclohydrocarbyloxy.

13. The compound of claim 1, wherein $R_4$ is selected from the group consisting of hydrogen, hydroxy, halogen, $C_1$-$C_8$alkyloxy, $C_5$-$C_{12}$aryloxy and $C_5$-$C_{12}$cyclohydrocarbyloxy.

14. The compound of claim 1, wherein $R_1$ represents one or more identical or different substituents selected from the group consisting of acetamido, 2-chloroacetamido, 2-hydroxyacetamido, N-methylacetamido, 2-(dimethylamino)acetamido, acetoxy, tert-butoxycarbonylamino and N-methyl-tert-butoxycarbonylamino.

15. The compound of claim 1, wherein $R_3$ is selected from the group consisting of hydrogen, chloro, hydroxy, methoxy, difluoromethoxy, trifluoromethoxy, ethoxy, propoxy, isopropoxy, benzyloxy and cyclopentyloxy.

16. The compound of claim 1, wherein $R_4$ is selected from the group consisting of hydrogen, chloro, hydroxy, methoxy, difluoromethoxy, trifluoromethoxy, ethoxy, propoxy, isopropoxy, benzyloxy and cyclopentyloxy.

17. The compound of claim 1, wherein $R_2$ is selected from the group consisting of methoxycarbonyl, ethoxycarbonyl, propoxycarbonyl, isopropoxycarbonyl and butoxycarbonyl, $R_5$ is hydrogen, $R_6$ is hydrogen and n is 1.

18. The compound of claim 1, wherein:
- $R_1$ is acetamido;
- $R_2$ is selected from the group consisting of methoxycarbonyl, ethoxycarbonyl and propoxycarbonyl;
- $R_3$ is selected from the group consisting of methoxy and ethoxy;
- $R_4$ is selected from the group consisting of methoxy and ethoxy;
- $R_5$ is hydrogen;
- $R_6$ is hydrogen; and
- n is 1.

19. A compound, selected from the group consisting of:
methyl 3-(4-acetamido-1,3-dioxoisoindolin-2-yl)-3-(3-ethoxy-4-methoxyphenyl)propionate;
methyl 3-(4-acetamido-1,3-dioxoisoindolin-2-yl)-3-(3,4-dimethoxyphenyl)propionate;
methyl 3-(4-acetamido-1,3-dioxoisoindolin-2-yl)-3-(3,4-diethoxyphenyl)propionate;
ethyl 3-(4-acetamido-1,3-dioxoisoindolin-2-yl)-3-(3-ethoxy-4-methoxyphenyl)propionate;
methyl (R)-3-(4-acetamido-1,3-dioxoisoindolin-2-yl)-3-(3-ethoxy-4-methoxyphenyl)propionate;
methyl (S)-3-(4-acetamido-1,3-dioxoisoindolin-2-yl)-3-(3-ethoxy-4-methoxyphenyl)propionate;
propyl 3-(4-acetamido-1,3-dioxoisoindolin-2-yl)-3-(3-ethoxy-4-methoxyphenyl)propionate;
isopropyl 3-(4-acetamido-1,3-dioxoisoindolin-2-yl)-3-(3-ethoxy-4-methoxyphenyl)propionate;
butyl 3-(4-acetamido-1,3-dioxoisoindolin-2-yl)-3-(3-ethoxy-4-methoxyphenyl)propionate;
methyl 3-(4-(2-chloroacetamino)-1,3-dioxoisoindolin-2-yl)-3-(3-ethoxy-4-methoxyphenyl)propionate;
methyl 3-(4-(2-(dimethylamino)acetamido)-1,3-dioxoisoindolin-2-yl)-3-(3-ethoxy-4-methoxyphenyl)propionate;
methyl 3-(4-(2-hydroxyacetamido)-1,3-dioxoisoindolin-2-yl)-3-(3-ethoxy-4-methoxyphenyl)propionate;
methyl 3-(4-acetamido-1,3-dioxoisoindolin-2-yl)-3-(3-ethoxy-4-isopropoxyphenyl)propionate;
methyl 3-(4-fluoro-1,3-dioxoisoindolin-2-yl)-3-(3-ethoxy-4-methoxyphenyl)propionate;
methyl 3-(4-acetamido-1,3-dioxoisoindolin-2-yl)-3-(3-ethoxy-4-cyclopentyloxyphenyl)propionate;
methyl 3-(4-methyl-1,3-dioxoisoindolin-2-yl)-3-(3-ethoxy-4-methoxyphenyl)propionate;
methyl 3-(5-fluoro-1,3-dioxoisoindolin-2-yl)-3-(3-ethoxy-4-methoxyphenyl)propionate;
methyl 3-(4,7-dichloro-1,3-dioxoisoindolin-2-yl)-3-(3-ethoxy-4-methoxyphenyl)propionate;
methyl 3-(4-(N-methylacetamido)-1,3-dioxoisoindolin-2-yl)-3-(3-ethoxy-4-methoxyphenyl)propionate;
methyl 3-(5-acetamido-1,3-dioxoisoindolin-2-yl)-3-(3-ethoxy-4-methoxyphenyl)propionate;
methyl 3-(4-acetamido-1,3-dioxoisoindolin-2-yl)-3-(3-(benzyloxy)-4-methoxyphenyl)propionate;
methyl 3-(4-(N-methyl-tert-butoxycarbonylamino)-1,3-dioxoisoindolin-2-yl)-3-(3-ethoxy-4-methoxyphenyl)propionate;
methyl 3-(4-acetamido-1,3-dioxoisoindolin-2-yl)-3-(3-propoxy-4-methoxyphenyl)propionate;
methyl 3-(4-acetamido-1,3-dioxoisoindolin-2-yl)-3-(3-cyclopentyloxy-4-methoxyphenyl)propionate;
methyl 3-(4-acetamido-1,3-dioxoisoindolin-2-yl)-3-(3-ethoxy-4-propoxyphenyl)propionate;
methyl 3-(4-hydroxy-1,3-dioxoisoindolin-2-yl)-3-(3-ethoxy-4-methoxyphenyl)propionate;
methyl 3-(4-acetoxy-1,3-dioxoisoindolin-2-yl)-3-(3-ethoxy-4-methoxyphenyl)propionate;
methyl 3-(4-acetamido-1,3-dioxoisoindolin-2-yl)-3-(3-hydroxy-4-methoxyphenyl)propionate;
methyl 3-(4-acetamido-1,3-dioxoisoindolin-2-yl)-3-(3-ethoxy-4-(benzyloxy)phenyl)propionate;
methyl 3-(4-acetamido-1,3-dioxoisoindolin-2-yl)-3-(3-ethoxy-4-hydroxyphenyl)propionate;
methyl 3-(4-acetamido-1,3-dioxoisoindolin-2-yl)-3-(3-methoxy-4-(benzyloxy)phenyl)propionate;
methyl 3-(4-acetamido-1,3-dioxoisoindolin-2-yl)-3-(3-methoxy-4-hydroxyphenyl)propionate;
methyl 3-(4-acetamido-1,3-dioxoisoindolin-2-yl)-3-phenylpropionate;
methyl 3-(4-acetamido-1,3-dioxoisoindolin-2-yl)-3-(3-chlorophenyl)propionate;
methyl 3-(4-acetamido-1,3-dioxoisoindolin-2-yl)-3-(4-ethoxypheny)propionate;
methyl 3-(4-acetamido-1,3-dioxoisoindolin-2-yl)-3-(4-chlorophenyl)propionate;
methyl 3-(4-(tert-butyloxycarbonylamino)-1,3-dioxoisoindolin-2-yl)-3-(3-ethoxy-4-methoxyphenyl)propionate;
methyl 3-(4-acetamido-1,3-dioxoisoindolin-2-yl)-3-(3-isopropoxy-4-methoxyphenyl)propionate;
methyl 3-(4-acetamido-1,3-dioxoisoindolin-2-yl)-3-(4-(difluoromethoxy)-3-ethoxyphenyl)propionate;
methyl 3-(4-acetamido-1,3-dioxoisoindolin-2-yl)-3-(3-ethoxy-4-(trifluoromethoxy)phenyl)propionate;
methyl 3-(4-acetamido-1,3-dioxoisoindolin-2-yl)-3-(3-(difluoromethoxy)-4-methoxyphenyl))propionate;
methyl 3-(4-acetamido-1,3-dioxoisoindolin-2-yl)-3-(4-methoxy-3-(trifluoromethoxy)phenyl)propionate;
ethyl (R)-3-(4-acetamido-1,3-dioxoisoindolin-2-yl)-3-(3-ethoxy-4-methoxyphenyl)propionate;
ethyl (S)-3-(4-acetamido-1,3-dioxoisoindolin-2-yl)-3-(3-ethoxy-4-methoxyphenyl)propionate;
methyl (R)-3-(4-acetamido-1,3-dioxoisoindolin-2-yl)-3-(3-isopropoxy-4-methoxyphenyl)propionate;
methyl (S)-3-(4-acetamido-1,3-dioxoisoindolin-2-yl)-3-(3-isopropoxy-4-methoxyphenyl)propionate;
methyl 3-(4-acetamido-1,3-dioxoisoindolin-2-yl)-3-(benzo[d][1,3]dioxol-5-yl)propionate; and
methyl 3-(4-acetamido-1,3-dioxoisoindolin-2-yl)-3-(2,3-dihydrobenzo[b][1,4]dioxin-6-yl)propionate,
or a stereoisomer or pharmaceutically acceptable salts thereof.

20. A pharmaceutical composition comprising a compound of claim 1 and a pharmaceutically acceptable carrier, diluent or excipient.

21. The pharmaceutical composition of claim 20, formulated as tablet, solution, granule, patch, ointment, gel, capsule, aerosol or suppository for administration via parenteral, transdermal, mucosal, nasal, buccal, sublingual or oral route.

22. A method for treating a disease associated with or mediated by immunoglobulin E (IgE), comprising administering a therapeutically effective amount of a compound of claim 9 to a subject in need thereof, wherein the disease is selected from the group consisting of dermatosis, psoriasis, eczema, atopic dermatitis, urticaria, asthma, asthma-chronic obstructive pulmonary disease (COPD) overlap syndrome (ACOS), allergic rhinitis, seasonal allergic rhinitis, drug-induced interstitial lung disease, bronchopulmonary aspergillosis, leprosy, pemphigoid and parasitic infections.

23. The method of claim 22, wherein the subject is a mammal.

24. A process for preparing a compound of claim 1, comprising:
(1) reacting a compound of formula (B-I) with malonic acid and ammonium acetate to obtain a compound of formula (B-II), formula (B-I)

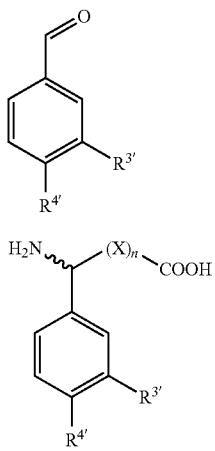

formula (B-II)

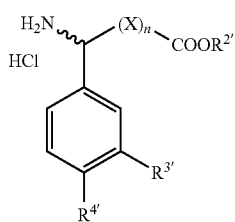

wherein groups represented by $R^{3'}$ and $R^{4'}$ in formula (B-I) and formula (B-II) have the same definitions as $R_3$ and $R_4$ in formula (II), (2) esterifying the compound of formula (B-II) with alcohol to obtain a compound of formula (B-III), formula (B-III)

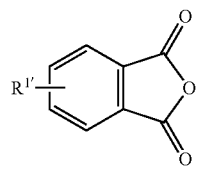

wherein groups represented by $R^{3'}$ and $R^{4'}$ in formula (B-II) and formula (B-III) have the same definitions as $R_3$ and $R_4$ in the formula (II), and $R^{2'}$ is hydrocarbyl; and (3) reacting a compound of formula (B-IV) with the compound of formula (B-III) to obtain the compound of formula (II), formula (B-IV)

wherein groups represented by $R^{1'}$, $R^{3'}$ and $R^{4'}$ in formula (B-III) and formula (B-IV) have the same definitions as $R_1$, $R_3$ and $R_4$ in formula (II), and $R^{2'}$ is hydrocarbyl;

wherein X is —$CR_5R_6$—, wherein $R_5$ is hydrogen, $R_6$ is hydrogen and n is 1.

25. The process of claim 24, wherein the compound of formula (B-I), malonic acid and ammonium acetate react are in a solvent selected from the group consisting of methanol, ethanol, isopropanol, water and a mixture thereof, and at 50° C. to 130° C. to obtain the compound of formula (B-II).

26. The process of claim 24, wherein the compound of formula (B-II) is esterified with alcohol in an organic solvent selected from the group consisting of alcohols, tetrahydrofuran, dichloromethane, ethyl acetate, methyl tert-butyl ether and a mixture thereof to obtain the compound of formula (B-III); and wherein the reaction is carried out at −20° C. to 30° C.

27. The process of claim 24, wherein an esterifying agent is selected from the group consisting of sulfoxide chloride, oxalyl chloride, HCl gas, acetyl chloride and a mixture thereof.

28. The process of claim 24, wherein a catalyst is added during the reaction of the compound of formula (B-IV) with the compound of formula (B-III) to obtain the compound of formula (II), wherein the catalyst is selected from the group consisting of sodium acetate, potassium acetate, sodium carbonate, potassium carbonate and a mixture thereof; and wherein the reaction is carried out at 50° C. to 180° C. in an organic solvent.

29. The method of claim 23, wherein the subject is a human.

* * * * *